US008710198B2

United States Patent
Miyake et al.

(10) Patent No.: US 8,710,198 B2
(45) Date of Patent: *Apr. 29, 2014

(54) CAPRAZENE AS A NOVEL COMPOUND AND DERIVATIVES THEREOF, AND CAPRAZOL AS A NOVEL COMPOUND AND DERIVATIVES THEREOF

(75) Inventors: Toshiaki Miyake, Yokohama (JP); Masayuki Igarashi, Machida (JP); Tetsuo Shitara, Yokohama (JP); Yoshiaki Takahashi, Tokyo (JP); Masa Hamada, Tokyo (JP)

(73) Assignee: Meiji Seika Pharma Co., Ltd., Tokyo-To (JP)

( * ) Notice: Subject to any disclaimer, the term of this patent is extended or adjusted under 35 U.S.C. 154(b) by 551 days.

This patent is subject to a terminal disclaimer.

(21) Appl. No.: 12/345,190

(22) Filed: Dec. 29, 2008

(65) Prior Publication Data

US 2009/0131652 A1    May 21, 2009

Related U.S. Application Data

(62) Division of application No. 10/543,887, filed as application No. PCT/JP2004/000969 on Jan. 30, 2004, now Pat. No. 7,482,439.

(30) Foreign Application Priority Data

Jan. 31, 2003  (JP) .................. 2003-25323

(51) Int. Cl.
  *C07H 19/067*  (2006.01)
  *C07D 403/08*  (2006.01)
  *C07D 403/14*  (2006.01)
  *C07D 243/08*  (2006.01)
  *C07D 405/14*  (2006.01)

(52) U.S. Cl.
  CPC ............ *C07H 19/067* (2013.01); *C07D 403/08* (2013.01); *C07D 403/14* (2013.01); *C07D 405/14* (2013.01)
  USPC ...................... 536/16.8; 536/28.53

(58) Field of Classification Search
  None
  See application file for complete search history.

(56) References Cited

U.S. PATENT DOCUMENTS 6,455,694 B1 *  9/2002  Kimura et al. ................ 540/492
7,482,439 B2 *  1/2009  Miyake et al. ............... 536/16.8

OTHER PUBLICATIONS

Ubukata et al., "The Structure of Liposidomycin B, an inhibitor of Bacterial Peptidoglycan Synthesis" Journal of the American Chemical Society (1988) vol. 110 pp. 4416-4417.*
Ubukata et al., "Structure Elucidation of Liposidomycins, a Class of Complex Lipid Nucleoside Antibiotics" Journal of Organic Chemistry (1992) vol. 57 pp. 6392-6403.*
Grzonka et al., "Empirical Investigation on the Reproducibility of 13C NMR Shift Values" J Chem Inf Comput Sci (1998) vol. 38 pp. 1096-1101.*

* cited by examiner

*Primary Examiner* — Eric S Olson
(74) *Attorney, Agent, or Firm* — B. Aaron Schulman; Stites & Harbison PLLC

(57) ABSTRACT

Caprazene is provided which is the compound represented by the following formula (I)

wherein Me stands for methyl group, and a 5"-N-alkoxycarbonyl or 5"-N-aralkyloxycarbonyl derivative thereof, and wherein said compound has the $^1$H-NMR and $^{13}$C-NMR data as set forth in Table 15.

2 Claims, No Drawings

CAPRAZENE AS A NOVEL COMPOUND AND DERIVATIVES THEREOF, AND CAPRAZOL AS A NOVEL COMPOUND AND DERIVATIVES THEREOF

CROSS-REFERENCE TO RELATED APPLICATIONS

The present application is a divisional of U.S. application Ser. No. 10/543,887, filed Jul. 29, 2005, which is a 371 application based on PCT/JP04/000969, filed Jan. 30, 2004, incorporated herein by reference.

TECHNICAL FIELD

This invention relates to a novel compound, caprazene, which is prepared by acid hydrolysis of antibiotics, caprazamycins A, B, C, D, E, F and/or G in an aqueous solution of an acid, and also this invention relates to a novel compound, caprazol, which is prepared by hydrolysis of caprazamycins in an aqueous solution of an inorganic base. Caprazene and caprazol are compounds represented by the stereo-structural formulae (I) and (IV) shown hereinafter, respectively, and they have no antibacterial activity, but are useful as intermediate compounds usable for the syntheses of a variety of antibacterial amide derivatives or ester derivatives therefrom. They are also useful as enzyme inhibitors having an inhibitory activity against enzyme MraY which takes part in the biosynthesis of the cell walls of bacteria.

This invention also includes a process for the preparation of caprazene and a process for the preparation of caprazol, both of which comprise a hydrolysis of caprazamycins. This invention further relates to a variety of novel caprazene amide derivatives or caprazene ester derivatives and a variety of novel caprazol amide derivatives or caprazol ester derivatives, all of which have antibacterial activities against various bacteria. These antibacterial caprazene derivatives and caprazol derivatives according to this invention are expected to be useful for the therapeutic treatment of tuberculosis and treatment of bacterial infections by atypical acid-fast bacteria, that is *Mycobacterium Avium* Complex (MAC) infection and other bacterial infections.

Further, this invention includes a variety of novel imidazolidinone derivatives (Code name: CP-IM) having the formula (VIII) hereinafter given which may be synthesized from caprazol through several reaction steps and which have an antibacterial activity.

Furthermore, this invention relates to a pharmaceutical composition comprising as the active ingredient a caprazene derivative or a caprazol derivative or an imidazolidinone derivative as mentioned above.

Moreover, this invention includes novel uridine derivative of the formula (IX) hereinafter given which is prepared by treating caprazol with methylamine to effect the ring-opening of the diazepine ring of caprazol and which is usable as an intermediate material for the synthesis of the said imidazolidinone derivative CP-IM.

BACKGROUND ART

In the chemotherapy of bacterial infections, particularly the chemotherapy of infections by acid-fast bacteria, there have already been used, as antibacterial agent, antibiotics such as rifampicin, kanamycin, streptomycin, viomycin, capreomycin, cycloserine, and the like.

A serious problem for the chemotherapy of the bacterial infections is in that bacteria causative of the bacterial infections become drug-resistant. In particular, the appearance of acid-fast bacteria which are resistant to rifampicin, kanamycin, streptomycin, viomycin, capreomycin, cycloserine and the like has brought about a social problem in respect of the chemotherapy of the acid-fast bacterial infections. Thus, there is now a keen request for providing a novel chemotherapeutic agent which is effective against bacterial infections as induced by the acid-fast bacteria resistant to the antibacterial drugs. Strongly requested also is a novel chemotherapeutic drug that is effective against the bacterial infections which are induced by atypical acid-fast bacteria and for which no chemotherapeutic treatment has been established yet.

In order to meet these requisites, therefore, there exists a strong demand to find out or to create novel compounds which have novel chemical structures and can exhibit excellent properties such as high antibacterial activities in a different way from those of the known antibiotics as hitherto utilized. We, the inventors of this invention, have carried out various investigations with the intention of providing novel antibiotics having excellent antibacterial activities which can meet the above-mentioned requisites.

Thus, there have already been proposed antibiotics, caprazamycins A, B, C, E and F which have been produced from *Streptomyces* sp. MK730-62F2 strain (deposited under the depository number of FERM BP-7218 under the Budapest Treaty) and which exhibit high antibacterial activities against acid-fast bacteria [see Pamphlet of PCT International Publication Number WO 01/12643A1 and European patent application first publn. EP 1211259A1].

Caprazamycins A, B, C, E and F are compounds represented by the following general formula (A)

(A)

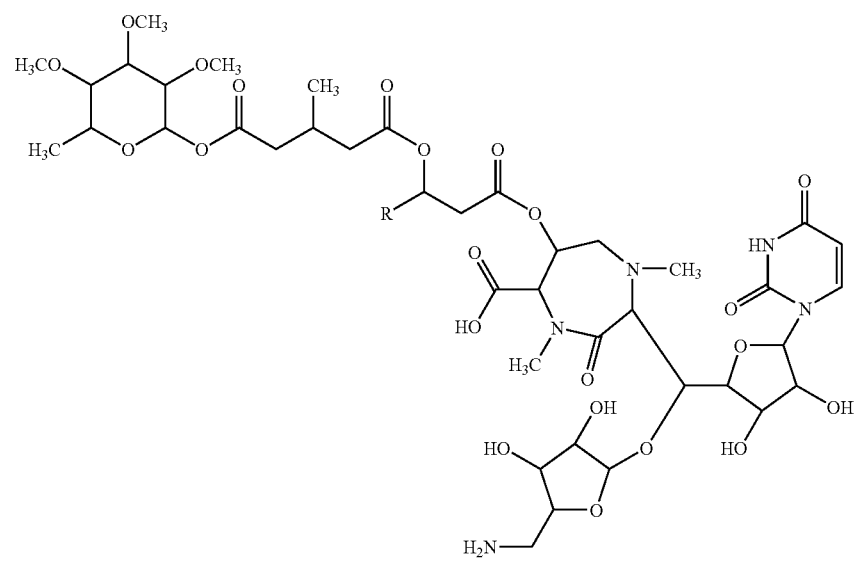

wherein R is tridecyl group for caprazamycin A, 11-methyl-dodecyl group for caprazamycin B, dodecyl group for caprazamycin C, undecyl group for caprazamycin E, and 9-methyl-decyl group for caprazamycin F.

Further, there have also been provided caprazamycins D, G, D1 and G1 which are produced from *Streptomyces* sp. MK730-62F2 strain (FERN BP-7218) (refer to the specification of PCT application No. PCT/JP02/13386 filed on Dec. 20, 2002).

Caprazamycin D and caprazamycin G are the compounds represented by the following general formula (B)

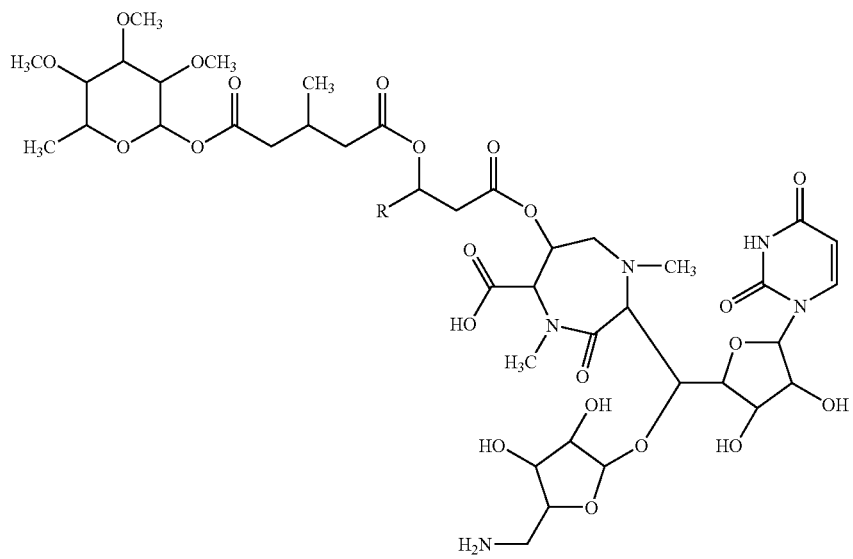

(B)

wherein R is 10-methyl-undecyl group —(CH$_2$)$_9$CH(CH$_3$)$_2$ for caprazamycin D and is 9-methyl-undecyl group —(CH$_2$)$_9$CH(CH$_3$)CH$_2$CH$_3$ for caprazamycin G.

Caprazamycin D1 and caprazamycin G1 are the compounds represented by the following general formula (C)

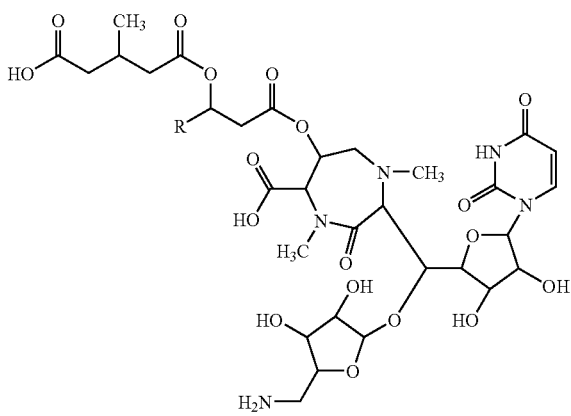

(C)

wherein R is 10-methyl-undecyl group —(CH$_2$)$_9$CH(CH$_3$)$_2$ for caprazamycin D1 and is 9-methyl-undecyl group —(CH$_2$)$_8$CH(CH$_3$)CH$_2$CH$_3$ for caprazamycin G1.

There have also been known liposidomycins A, B and C which are produced from *Streptomyces glyceosporeus* SN-1051M (FERM BP-5800) (refer to Japanese Patent Application First Publication KOKAI Sho-61-282088).

Liposidomycins A, B and C are compounds represented by the following general formula (D)

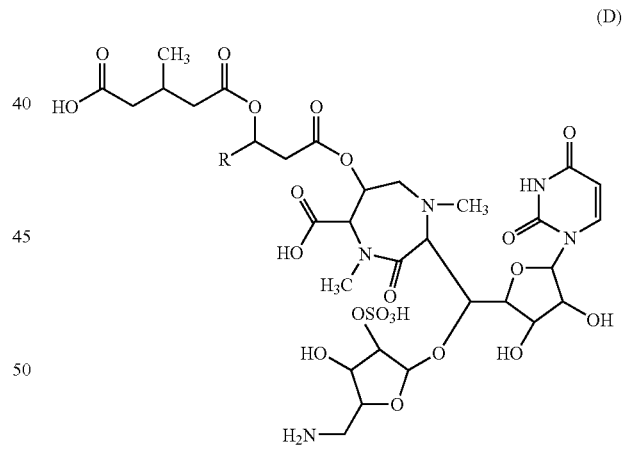

(D)

wherein R is 4,7-tridecadienyl group —(CH$_2$)$_3$—CH=CH—CH$_2$—CH=CH—(CH$_2$)$_4$—CH$_3$ for liposidomycin A, 9-methyl-decyl group —(CH$_2$)$_8$—CH(CH$_3$)$_2$ for liposidomycin B and undecyl group —(CH$_2$)$_{10}$—CH$_3$ for liposidomycin C.

Further, there have been known liposidomycins G, H, K, L, M, N and Z and other liposidomycins' homologues (refer to Pamphlet of PCT International Publication Number WO97/41248 and European Patent Application First Publication, EP 1001035A1).

Also known already are liposidomycins X-(III), Y-(III), Z-(III), C-(III), V-(III), A-(III), G-(III), M-(III), K-(III), and N-(III) (see European Patent Application First Publication EP 1001035A1) and they are compounds represented by the following general formula (E)

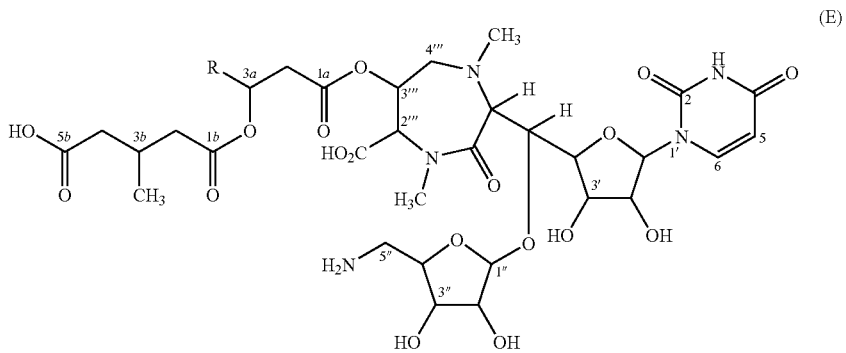

(E)

wherein R is a long chain alkyl group shown in the Pamphlet of WO97/41248 or in Table 1 of the European Patent Application Publication EP1001035A1.

A report has been issued that relates to investigation on elucidation of chemical structures of liposidomycins A, B and C [refer to The Journal of Organic Chemistry, Vol. 57, No. 24, pages 6392-6403 (1992)]. This report describes (see the J.O.C., pages 6397-6399) three compounds, namely, compound 10 (given as anhydrodeacyl-liposidomycin having molecular weight of 557) of the following planar structural formula (F)

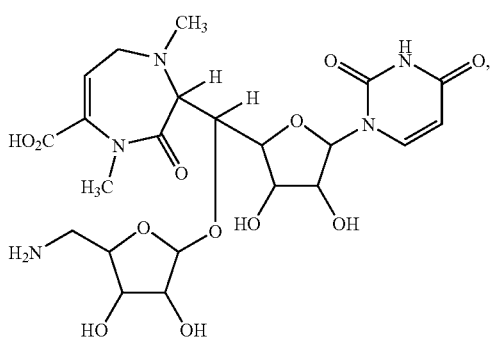

(F)

and Compound II (given as anhydrodeacyl-liposidomycin having molecular weight of 637) of the following planar structural formula (G)

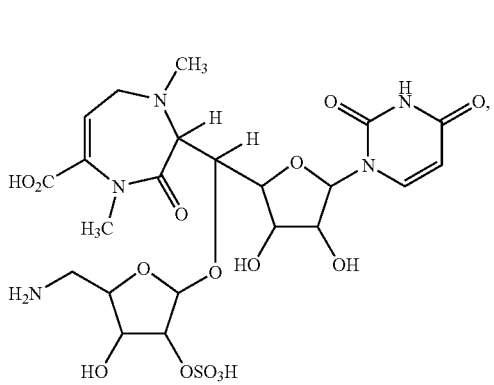

(G)

and Compound 12 of the following planar structural formula (H)

(H)

each of the three compounds having been prepared by an alkaline hydrolysis of a mixture of liposidomycins B and C in a dilute aqueous NaOH solution at 37° C. to produce Compound 10 and Compound II and by a reductive deacylation of a mixture of liposidomycins B and C with $LiBH_4$ to produce Compound 12. The report also shows $^{13}$C-NMR data (Table III) and $^1$H-NMR data (Table IV) of these three compounds, but the stereo-structures of these three compounds are unknown yet until now.

Caprazamycins A to G referred to in the above have one common skeletal structure with each another and have excellent antibacterial activities. However, the antibacterial activities of caprazamycins A, B, C, D, E, F and G are different, among them, depending upon the nature of bacteria. Further, upon the preparation of these caprazamycins by the cultivation of Streptomyces sp. MK730-62F2 strain referred to above as a caprazamycin-producing bacterial strain, followed by the recovery of the caprazamycins from the resulting culture broth, it is usual that a mixture of caprazamycins A to G is first obtained. Thus, it is necessary, in order to separate the caprazamycins A to G from each other, to carry out time-consuming and troublesome operations necessarily comprising the high performance liquid chromatography (HPLC).

Therefore, it has been requested to synthesize certain novel semi-synthesized antibiotics which can have antibacterial activities equivalent or superior to those of caprazamycins A, B and C-G, and which can be prepared in an efficient way by utilizing a mixture comprising two or more of caprazamycins A to G or by utilizing any one of caprazamycins A, B or C, alone. It has also been requested to provide certain novel semi-synthesized antibiotics which comprise the skeletal structure common to caprazamycins A to G.

DISCLOSURE OF THE INVENTION

In order to satisfy the request as above-mentioned, we, the inventors of this invention, have made various investigations. First of all, we have carried out some experiments wherein at least one of caprazamycins A to G, preferably caprazamycin B, is subjected to acid-hydrolysis in an aqueous acid solution, for example, an aqueous acetic acid solution at a concentration of 50-90% by weight, or a dilute aqueous sulfuric acid or hydrogen chloride solution. As a result, we have found that the resulting reaction solution of the acid-hydrolysis of a caprazamycin contains the compound thus produced which is represented by the following formula (I)

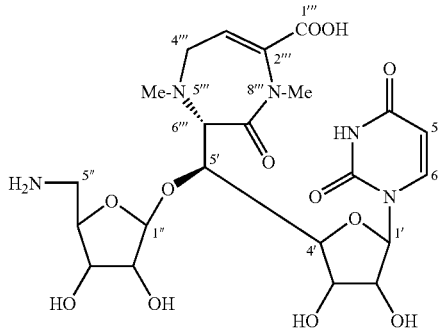

(I)

wherein Me stands for methyl group, and we have succeeded in isolating said compound as a colorless solid. The compound of the formula (I) above has been recognized to comprise in its molecule a 5'-substituted-uridine moiety and a 5-amino-5-deoxy-D-ribose moiety and a 1,4-diazepinone moiety having one double bond.

We have measured physicochemical properties and NMR data of the compound so isolated. Further, the 5"-N-tert-butoxycarbonyl derivative has been prepared from the said compound and then crystallized out. The derivative obtained as the crystals has been analyzed by X-ray powder diffractometry. Thus, the compound now isolated has been decided to have the steric chemical structure shown by the formula (I) above.

Further, taking the physicochemical properties, $^1$H-NMR data and $^{13}$C-NMR data of said compound into consideration collectively, we have decided the said compound to be a novel substance and designated it as caprazene.

By the way, when comparing the $^{13}$C-NMR data (Table III) and $^1$H-NMR data (Table IV) of the Compound 10 of which stereo-structure is unknown yet and which is given by the planar structural formula on pages 6397-6399 and page 6402 of the literature, The Journal of Organic Chemistry, Vol. 57, No. 24 mentioned above with those of caprazene of the formula (I) of this invention, some of the data for the Compound 10 are not necessarily consistent with $^{13}$C-NMR data and $^1$H-NMR data of caprazene of the formula (I) of this invention (refer to Table 15 in Example 1 hereinafter given). This is the reason why we have now finally decided that caprazene produced by us is a novel compound which is different from the Compound 10 in some part of the stereo-structure.

We have further succeeded in synthesizing 5"-amino-protected derivatives of caprazene by introducing, into the free amino group of caprazene of the formula (I) above, an alkoxycarbonyl group, for example, tert-butoxycarbonyl group (usually abbreviated as Boc), or an aralkyloxycarbonyl group, for example, benzyloxycarbonyl group, each of which is conventionally used as an amino-protecting group in sugar chemistry.

According to a first aspect of this invention, therefore, there are provided caprazene which is the compound represented by the following formula (I)

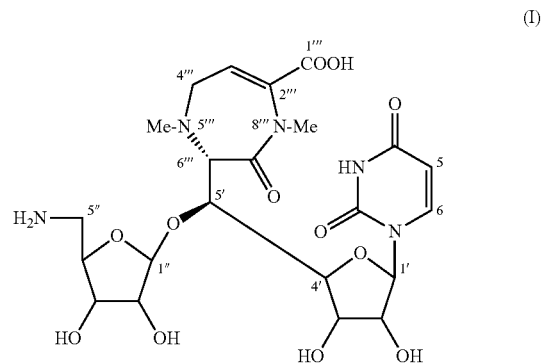

(I)

wherein Me stands for methyl group, and a 5"-N-alkoxycarbonyl or 5"-N-aralkyloxycarbonyl derivative thereof.

Further, according to a second aspect of this invention, there is provided a process for the preparation of caprazene which is the compound represented by the following formula (I)

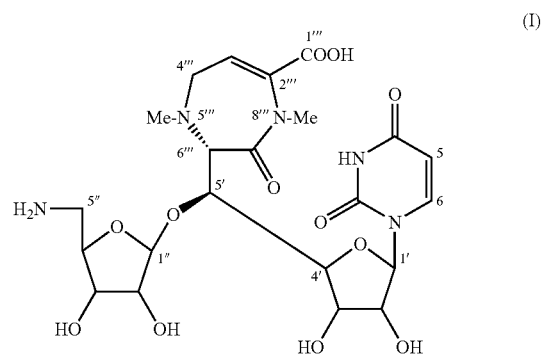

(I)

wherein Me stands for methyl group, the process comprising hydrolyzing caprazamycin A, B, C, D, E, F or G or a mixture of two or more of caprazamycins A to G in an aqueous solution of an acid at room temperature or under heating.

In the process according to the second aspect of this invention, it is preferred that at least one of caprazamycins A to G is hydrolyzed in an aqueous acid solution, for example, in an aqueous acetic acid or an aqueous sulfuric acid or an aqueous hydrogen chloride solution.

The aqueous solution of an acid used for the acid hydrolysis of caprazamycins may be those of an organic acid, for example, acetic acid or n-propionic acid, or those of an inorganic acid, for example, hydrochloric acid or sulfuric acid. It is preferred to use an aqueous acetic acid solution containing acetic acid at a concentration of 50-90% (by weight) or a dilute aqueous hydrochloric acid solution containing hydrogen chloride (HCl) at a concentration of 3% by weight or less. The acid hydrolysis reaction of caprazamycins may be carried out at room temperature, but it may also be effected at an elevated temperature of 40-100° C.

After the finish of the hydrolysis reaction of caprazamycins, the resulting reaction solution is concentrated to give a syrupy concentrate, to which is added acetone to deposit a precipitate, which is then recovered by filtration. The resulting solid is washed with acetone and dried, and thus caprazene of the formula (I) may be recovered as a colorless solid. The solid caprazene may be dissolved in a mixture of water-acetone and then deposited as crystals. The physicochemical properties of caprazene are shown in Example 1 hereinafter given.

We have further proceeded with our investigations. Thus, we have found that caprazene is suspended in a mixture of water-dioxane (2:1) and to the resulting suspension is added triethylamine, so that there may be obtained a homogeneous caprazene solution. We have further found that there can be produced 5"-N-t-butoxycarbonyl caprazene or 5"-N-benzyloxycarbonyl caprazene by reacting caprazene present in the resulting homogeneous solution with di-t-butyl dicarbonate having the following formula (X)

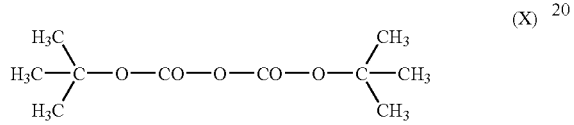
(X)

or N-(benzyloxycarbonyloxy) succinimide to cause t-butoxycarbonylation or benzyloxycarbonylation reaction at the 5-amino group of the 5-amino-5-deoxy-D-ribose moiety of caprazene.

The 5"-N-t-butoxycarbonylcaprazene or 5"-benzyloxycarbonylcaprazene thus formed is suspended in tetrahydrofuran (THF), and to the resulting suspension are then added triethylamine and N,N-bis(2-oxo-3-oxazolidinyl) phosphinic chloride as activator of carboxyl group to give a homogeneous reaction mixture, to which mixture is then added an amine compound of the following general formula (XI)

wherein $R^1$ is a straight chain or a substantially straight chain alkyl group of 5-21 carbon atoms, a straight chain or a substantially straight chain alkenyl group of 5-21 carbon atoms or a cycloalkyl group of 5-12 carbon atoms, or $R^1$ is a phenyl group having a straight chain alkyl group of 1-14 carbon atoms or a straight chain alkoxy group of 1-9 carbon atoms or a cycloalkyl group of 5-12 carbon atoms at the para-position of the phenyl group, so as to bring about an amidation reaction on the 2'''-carboxyl group of the caprazene with the amine compound of the formula (XI), and thus there can be produced a 5"-N-protected-caprazene-1'''-amide derivative represented by the following general formula (IIa)

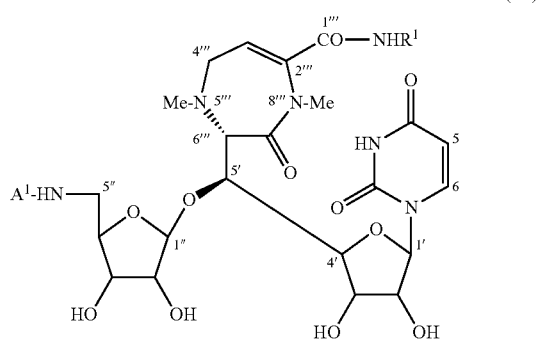

wherein Me stands for methyl group, $R^1$ has the same meaning as $R^1$ in the formula (XI) above and $A^1$ stands for t-butoxycarbonyl group (abbreviated as Boc) or benzyloxycarbonyl group (abbreviated as Z). In addition, it has been found that the protection of 5"-amino group of caprazene of the formula (I) can also be made by using any alkoxycarbonyl group or aralkyloxycarbonyl group conventionally used as the amino-protecting group in sugar chemistry instead of the above-said t-butoxycarbonyl group or benzyloxycarbonyl group.

The elimination of 5"-N-Boc group or 5"-N—Z group from the amide derivative of the formula (IIa) can be made when the 5"-N-protected caprazene-1'''-amide derivative is subjected to conventional method for the elimination of the amino-protecting group in sugar chemistry, for example, to hydrolysis with trifluoroacetic acid in methanol for the elimination of Boc group, or to hydrogenolysis for the elimination of Z group, thereby affording a caprazene-1'''-amide derivative having the following general formula (IIb)

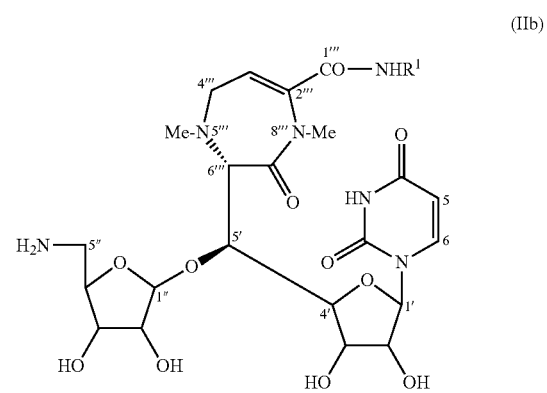

wherein Me and $R^1$ have the same meanings as defined above. The caprazene-1'''-amide derivative of the general formula (IIb), when be reacted with trifluoroacetic acid, hydrochloric acid, sulfuric acid or phosphoric acid, will give the corresponding acid addition salt of the amide derivative of the formula (IIb) which is soluble in water.

We have found that a caprazene-1'''-amide derivative of the general formula (IIb) above and 5"-N-Boc- or 5"-N—Z-protected derivative thereof have antibacterial activities against various bacteria including tubercle *bacillus*.

According to a third aspect of this invention, therefore, there are provided a caprazene-1'''-amide derivative and its 5"-N-alkoxycarbonyl or aralkyloxycarbonyl derivative which are each presented by the following general formula (II)

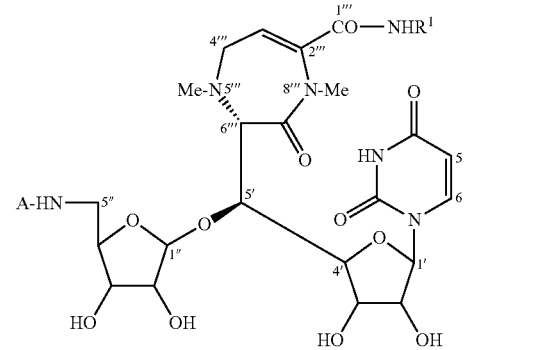

wherein Me is methyl group, $R^1$ is a straight chain or a substantially straight chain alkyl group of 5-21 carbon atoms, a straight chain or a substantially straight chain alkenyl group of 5-21 carbon atoms or a cycloalkyl group of 5-12 carbon atoms, or $R^1$ is a phenyl group having a straight chain alkyl group of 1-14 carbon atoms or a straight chain alkoxy group of 1-9 carbon atoms or a cycloalkyl group of 5-12 carbon atoms at the para-position of the phenyl group, A is hydrogen atom or A is an amino-protecting group including an alkoxycarbonyl group, particularly tert-butoxycarbonyl group, or an aralkyloxycarbonyl group, particularly benzyloxycarbonyl group, or a pharmaceutically acceptable acid addition salt thereof.

The caprazene-1'''-amide derivative of the general formula (II) includes (i) a caprazene-1'''-amide derivative where A is hydrogen atom and $R^1$ is an alkyl group, alkenyl group or cycloalkyl group as defined above, and (ii) a caprazene-1'''-amide derivative where A is hydrogen atom and $R^1$ is a phenyl group having an alkyl group, alkoxy group or cycloalkyl group at the para-position as defined above.

In the caprazene-1'''-amide derivatives of the formula (II), the straight chain alkyl group of 5-21 carbon atoms as $R^1$ may be those exemplified in the following Table 1.

TABLE 1

| Alkyl group | |
|---|---|
| Formula | Name |
| $C_5H_{11}-$ | Pentyl(Amyl) |
| $C_6H_{13}-$ | Hexyl |
| $C_7H_{15}-$ | Heptyl |
| $C_8H_{17}-$ | Octyl |
| $C_9H_{19}-$ | Nonyl |
| $C_{10}H_{21}-$ | Decyl |
| $C_{11}H_{23}-$ | Undecyl |
| $C_{12}H_{25}-$ | Dodecyl |
| $C_{13}H_{27}-$ | Tridecyl |
| $C_{14}H_{29}-$ | Tetradecyl |
| $C_{15}H_{31}-$ | Pentadecyl |
| $C_{16}H_{33}-$ | Hexadecyl |
| $C_{17}H_{35}-$ | Heptadecyl |
| $C_{18}H_{37}-$ | Octadecyl |
| $C_{19}H_{39}-$ | Nonadecyl |
| $C_{20}H_{41}-$ | Icocyl |
| $C_{21}H_{43}-$ | Henicosyl |

Substantially straight chain alkyl group of 5-21 carbon atoms as $R^1$ defined above may be a ($C_5$-$C_{21}$) alkyl group having 1-3 methyl groups, 1-3 ethyl groups or 1-3 n-propyl groups as substituted in the length of the alkyl chain or at the terminal carbon atom of the alkyl chain, which may, for example, include 9-methyl-undecyl group —$(CH_2)_8CH(CH_3)CH_2CH_3$ or 10-methyl-undecyl group —$(CH_2)_9CH(CH_3)_2$.

Straight chain alkenyl group of 5-21 carbon atoms as $R^1$ defined above may be pentenyl group, hexenyl group, heptenyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group or icosenyl group. The double bond of the alkenyl group may be positioned in the length of the alkenyl chain or at the α-carbon atom or ω-carbon atom.

Cycloalkyl group of 5-12 carbon atoms as $R^1$ defined above may be cyclopentyl group, cyclohexyl group, cycloheptyl group, cyclooctyl, group, cyclononyl group, cyclodecyl group, cycloundecyl group or cyclododecyl group. There may be substituted 1-3 methyl groups or 1-3 ethyl groups as the substituents on the cycloalkane ring.

Concrete examples of a phenyl group having an alkyl group, alkoxy group or cycloalkyl group at the para-position defined above for $R^1$ are shown in the column of $R^1$ in the Table 2-2 given hereinafter.

Concrete examples of a caprazene-1'''-amide derivative of the following formula (IIb) which is included within the 5''-N-unprotected-caprazene-1'''-amide derivative of the general formula (II) according to the third aspect of this invention are shown in the following Table 2-1 and Table 2-2 together with their specific rotation data.

TABLE 2-1

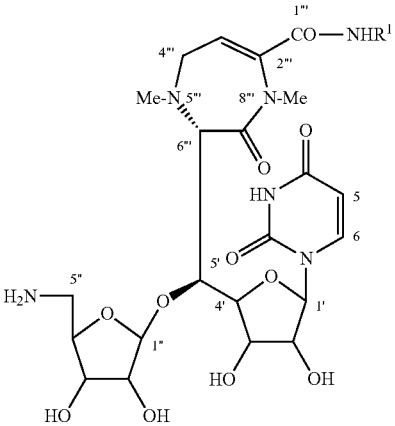

(IIb)

| Compound code name | $R^1$ group in the formula (IIb) | Specific rotation $[\alpha]_D$ (c 0.5, in water) |
|---|---|---|
| Compound II-A | —$(CH_2)_5CH_3$ | $[\alpha]_D^{20}$ +70° |
| Compound II-B | —$(CH_2)_6CH_3$ | $[\alpha]_D^{21}$ +72° |
| Compound II-C | —$(CH_2)_7CH_3$ | $[\alpha]_D^{20}$ +72° |
| Compound II-D | —$(CH_2)_8CH_3$ | $[\alpha]_D^{20}$ +73° |
| Compound II-E | —$(CH_2)_9CH_3$ | $[\alpha]_D^{21}$ +72° |
| Compound II-F | —$(CH_2)_{10}CH_3$ | $[\alpha]_D^{20}$ +73° |
| Compound II-G | —$(CH_2)_{11}CH_3$ | $[\alpha]_D^{21}$ +72° |
| Compound II-H | —$(CH_2)_{12}CH_3$ | $[\alpha]_D^{20}$ +72° |
| Compound II-I | —$(CH_2)_{13}CH_3$ | $[\alpha]_D^{20}$ +68° |
| Compound II-J | —$(CH_2)_{14}CH_3$ | $[\alpha]_D^{21}$ +66° |
| Compound II-K | —$(CH_2)_{15}CH_3$ | $[\alpha]_D^{20}$ +67° |
| Compound II-L | —$(CH_2)_{16}CH_3$ | $[\alpha]_D^{20}$ +67° |
| Compound II-M | —$(CH_2)_{17}CH_3$ | $[\alpha]_D^{20}$ +66° |
| Compound II-N | —$(CH_2)_{18}CH_3$ | $[\alpha]_D^{20}$ +60° |
| Compound II-O | —$(CH_2)_{19}CH_3$ | $[\alpha]_D^{20}$ +60° |
| Compound II-P | —$(CH_2)_{20}CH_3$ | $[\alpha]_D^{20}$ +60° |
| Compound II-Q | Cyclododecyl group | $[\alpha]_D^{20}$ +71° |
| Compound II-R | Oleyl group —$(CH_2)_8CH\!=\!CH(CH_2)_7CH_3$ (cis form) | $[\alpha]_D^{20}$ +64° |

TABLE 2-2

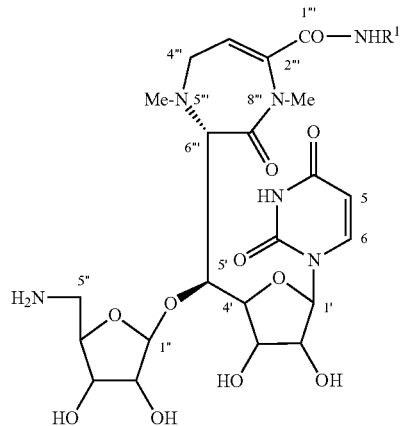

(IIb)

| Compound code name | R¹ group in the formula (IIb) | Specific rotation $[\alpha]_D^{22}$ (c 0.5, in methanol) |
|---|---|---|
| compound II-1 | —C₆H₄—CH₃ (para) | +81° |
| Compound II-2 | —C₆H₄—CH₂CH₃ (para) | +80° |
| Compound II-3 | —C₆H₄—(CH₂)₂CH₃ (para) | +78° |
| Compound II-4 | —C₆H₄—(CH₂)₃CH₃ (para) | +76° |
| Compound II-5 | —C₆H₄—(CH₂)₄CH₃ (para) | +74° |
| Compound II-6 | —C₆H₄—(CH₂)₅CH₃ (para) | +73° |
| Compound II-7 | —C₆H₄—(CH₂)₆CH₃ (para) | +72° |
| Compound II-8 | —C₆H₄—(CH₂)₇CH₃ (para) | +71° |
| Compound II-9 | —C₆H₄—(CH₂)₈CH₃ (para) | +69° |
| Compound II-10 | —C₆H₄—(CH₂)₉CH₃ (para) | +67° |

TABLE 2-2-continued

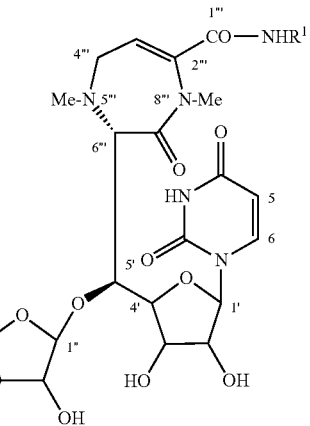

(IIb)

| Compound code name | R¹ group in the formula (IIb) | Specific rotation $[\alpha]_D^{22}$ (c 0.5, in methanol) |
|---|---|---|
| Compound II-11 | —C₆H₄—(CH₂)₁₀CH₃ (para) | +67° |
| Compound II-12 | —C₆H₄—(CH₂)₁₁CH₃ (para) | +66° |
| Compound II-13 | —C₆H₄—(CH₂)₁₂CH₃ (para) | +66° |
| Compound II-14 | —C₆H₄—(CH₂)₁₃CH₃ (para) | +64° |
| Compound II-15 | —C₆H₄—OCH₃ (para) | +80° |
| Compound II-16 | —C₆H₄—OCH₂CH₃ (para) | +80° |
| Compound II-17 | —C₆H₄—O(CH₂)₂CH₃ (para) | +80° |
| Compound II-18 | —C₆H₄—O(CH₂)₃CH₃ (para) | +81° |
| Compound II-19 | —C₆H₄—O(CH₂)₄CH₃ (para) | +77° |
| Compound II-20 | —C₆H₄—O(CH₂)₅CH₃ (para) | +78° |

TABLE 2-2-continued (IIb)

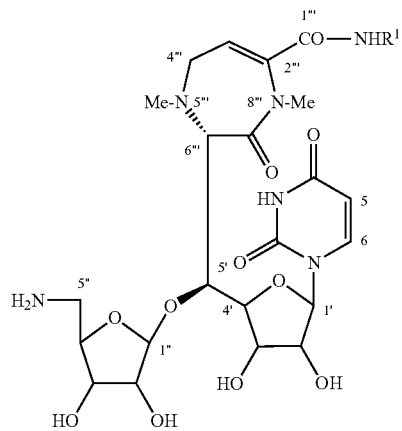

| Compound code name | R¹ group in the formula (IIb) | Specific rotation $[\alpha]_D^{22}$ (c 0.5, in methanol) |
|---|---|---|
| Compound II-21 | —⟨C₆H₄⟩—O(CH₂)₆CH₃ | +76° |
| Compound II-22 | —⟨C₆H₄⟩—O(CH₂)₇CH₃ | +76° |
| Compound II-23 | —⟨C₆H₄⟩—O(CH₂)₈CH₃ | +74° |
| Compound II-24 | —⟨C₆H₄⟩—⟨C₆H₁₁⟩ | +76° |

Concrete examples of a caprazene-1′″-amide derivative of the following formula (IIa) which is included within the 5″-N-protected-caprazene-1′″-amide derivative of the general formula (II) according to the third aspect of this invention are shown in the following Table 3 together with their specific rotation data.

TABLE 3

(IIa)

| Compound code name | R¹ group in the formula (IIa) | Amino-protecting group (A′) in formula (IIa) | Specific rotation $[\alpha]_D^{19}$ (c 0.5, in chloroform) |
|---|---|---|---|
| Compound II-G-N-Boc | —(CH₂)₁₁CH₃ | t-butoxycarbonyl group | +105° |
| Compound II-H-N-Boc | —(CH₂)₁₂CH₃ | t-butoxycarbonyl group | +105° |
| Compound II-I-N-Boc | —(CH₂)₁₃CH₃ | t-butoxycarbonyl group | +103° |
| Compound II-J-N-Boc | —(CH₂)₁₄CH₃ | t-butoxycarbonyl group | +103° |

TEST EXAMPLE 1

Minimum growth inhibitory concentrations (mcg/ml) of caprazene-1′″-amide derivatives of the formula (II) against some of microorganisms were measured on an agar culture medium by a serial dilution method according to the standard method as provided by Japanese Society of Chemotherapy. For the cultivation of *Mycobacterium smegmatis* (one of anti-fast bacteria), however, there was used an agar culture medium with the addition of 1% glycerine (the same applies to in the following tests). The results are shown in the following Table 4-1 and Table 4-2.

TABLE 4-1

| Compound code name of the test compound (see Table 2, Table 3) | Minimum growth inhibitory concentration (mcg/ml) against bacteria | | |
|---|---|---|---|
| | *Staphylococcus aureus* FDA209P | *Micrococcus luteus* FDA16 | *Mycobacterium smegmatis* ATCC607 |
| Compound II-A | >100 | 3.13 | 100 |
| Compound II-B | 25 | 1.56 | 25 |
| Compound II-C | 6.25 | 0.78 | 12.5 |
| Compound II-D | 6.25 | 0.39 | 3.13 |
| Compound II-E | 25 | 0.39 | 0.78 |
| Compound II-F | 1.56 | 0.39 | 0.39 |
| Compound II-G | 3.13 | 0.39 | 0.39 |
| Compound II-H | 3.13 | 0.78 | <0.20 |
| Compound II-I | 3.13 | 0.78 | 0.78 |
| Compound II-J | 1.56 | 0.78 | 1.56 |
| Compound II-K | 3.13 | 0.78 | 3.13 |
| Compound II-L | 1.56 | 1.56 | 3.13 |
| Compound II-M | 6.25 | 0.78 | 3.13 |
| Compound II-N | 6.25 | 0.78 | 50 |
| Compound II-O | 3.13 | 3.13 | 25 |

TABLE 4-1-continued

| Compound code name of the test compound (see Table 2, Table 3) | Minimum growth inhibitory concentration (mcg/ml) against bacteria | | |
|---|---|---|---|
| | Staphylococcus aureus FDA209P | Micrococcus luteus FDA16 | Mycobacterium smegmatis ATCC607 |
| Compound II-P | 6.25 | 3.13 | 50 |
| Compound II-Q | 100 | 0.20 | 3.13 |
| Compound II-R | 1.56 | 1.56 | 1.56 |
| Compound II-G-N-Boc | 50 | 50 | 50 |
| Compound II-H-N-Boc | 25 | 12.5 | 25 |
| Compound II-I-N-Boc | 12.5 | 12.5 | 25 |
| Compound II-J-N-Boc | 12.5 | 12.5 | 25 |

TABLE 4-2

| Compound Code name of the test compound (see Table 2, Table 3) | Minimum growth inhibitory concentration (mcg/ml) against bacteria | | |
|---|---|---|---|
| | Staphylococcus aureus FDA209P | Micrococcus luteus FDA16 | Mycobacterium smegmatis ATCC607 |
| Compound II-1 | >100 | 3.13 | 100 |
| Compound II-2 | 100 | 3.13 | 50 |
| Compound II-3 | 25 | 3.13 | 12.5 |
| Compound II-4 | 12.5 | 0.78 | 6.25 |
| Compound II-5 | 3.13 | 0.2 | 3.13 |
| Compound II-6 | 1.56 | 0.39 | 0.78 |
| Compound II-7 | 1.56 | <0.20 | <0.20 |
| Compound II-8 | 3.13 | 0.39 | 0.78 |
| Compound II-9 | 3.13 | 0.39 | 1.56 |
| Compound II-10 | 3.13 | <0.20 | 3.13 |
| Compound II-11 | 3.13 | 0.39 | 3.13 |
| Compound II-12 | 3.13 | 0.78 | 6.25 |
| Compound II-13 | 3.13 | 1.56 | 12.5 |
| Compound II-14 | 6.25 | 3.13 | 25 |
| Compound II-15 | 100 | 3.13 | 50 |
| Compound II-16 | 50 | 3.13 | 25 |
| Compound II-17 | 25 | 1.56 | 12.5 |
| Compound II-18 | 12.5 | 0.78 | 6.25 |
| Compound II-19 | 6.25 | 0.78 | 3.13 |
| Compound II-20 | 6.25 | 0.39 | 1.56 |
| Compound II-21 | 3.13 | 0.20 | 0.78 |
| Compound II-22 | 3.13 | 0.39 | 0.78 |
| Compound II-23 | 1.56 | 0.39 | 0.78 |
| Compound II-24 | 12.5 | 0.39 | 1.56 |

The process for the preparation of a caprazene-1'''-amide derivative of the formula (II) according to the third aspect of this invention is now explained.

At first, caprazene of the formula (I) is suspended in a mixture of water-dioxane, and to the resulting suspension is added triethylamine to prepare a homogeneous solution of caprazene. To the resulting caprazene solution, is added an alkoxycarbonylating reagent or an aralkyloxycarbonylating reagent which is conventionally used according to the amino-protecting technique well known in the sugar chemistry, and the reaction intended is conducted at room temperature. Thus, there is produced in the resulting reaction solution a 5''-N-alkoxycarbonyl- or 5''-N-aralkyloxycarbonyl-caprazene. The reaction solution is concentrated and the resulting solid residue is washed with ethyl acetate and then dried, and thus there is afforded the desired 5''-N-alkoxycarbonyl- or 5''-N-aralkyloxycarbonyl-caprazene as a solid.

Then, 5''-N-alkoxycarbonyl- or 5''-N-aralkyloxycarbonyl-caprazene is either dissolved in pyridine to give a solution or is suspended in tetrahydrofuran (THF) to give a suspension and triethylamine is added to the suspension. In the said pyridine solution or THF suspension of the 5''-N-protected caprazene, an amine compound $R^1$—$NH_2$ of the formula (XI) above is reacted with the carboxyl group at the 2'''-position of the 5''-N-protected-caprazene according to the usual method for the amidation of carboxylic acid. For the amidation reaction, it is convenient to add to the reaction system N,N-bis-(2-oxo-3-oxazolidinyl)-phosphinic chloride as an activator of the carboxyl group, and then to conduct the reaction at room temperature.

The resulting amidation reaction solution is concentrated, and the resulting syrupy concentrate is extracted with chloroform and then the resulting chloroform extract in the form of a solution is washed with water and then concentrated, thus to give a residue containing the desired 5''-N-protected-caprazene-1'''-amide derivative. The residue is dissolved in chloroform and the resulting solution is purified by subjecting it to a silica-gel column chromatography which is developed with a mixed solvent of chloroform-methanol (10:1). Eluate fractions containing the object product from the silica-gel column are collected and the fractions collected are concentrated to afford a 5''-N-protected-caprazene-1'''-amide derivative of the general formula (II) as a solid.

Further, the elimination of the 5''-N-protecting group from the resulting 5''-N-protected-caprazene-1'''-amide derivative can be achieved by treating the said N-protected derivative in a usual manner for the elimination of amino-protecting group, thereby to produce the 5''-N-unprotected-caprazene-1'''-amide derivative of the general formula (II). In order to eliminate Boc group as the amino-protecting group, it is convenient, as described before, to dissolve the 5''-N-protected-caprazene-1'''-amide derivative in methanol containing 80% trifluoroacetic acid (TFA) and then to stir the resulting solution at room temperature. The resulting reaction solution from the elimination of the amino-protecting group is concentrated to give a syrupy concentrate, to which diethyl ether is added to deposit a precipitate which is then filtered, washed with diethyl ether and dried, thereby to yield the 5''-N-unprotected-caprazene-1'''-amide derivative of the general formula (II) in the form of an addition salt of bis-trifluoroacetic acid as a solid.

We have further made another investigation. Thus, a 5''-N-protected-caprazene as produced in the synthesis of caprazene-1'''-amide derivative of the general formula (II) above is dissolved in pyridine, and in the resultant pyridine solution, an alcohol of the following general formula (XII)

$$R^2\text{—OH} \qquad (XII)$$

wherein $R^2$ is a straight chain or a substantially straight chain alkyl group of 5-21 carbon atoms or a straight chain or a substantially straight chain alkenyl group of 5-21 carbon atoms or an alkynyl group of 5-21 carbon atoms, is reacted with the 5''-N-protected caprazene at room temperature in the presence of N,N-bis(2-oxo-3-oxazolidinyl)phosphinic chloride as added (as activator of carboxyl group). Thus, there occurs the esterification reaction between the 2'''-carboxyl group of the 5''-N-protected caprazene and the alcohol of the formula (XII), to produce a 5''-N-protected caprazene-1'''-ester derivative represented by the following general formula (IIIa)

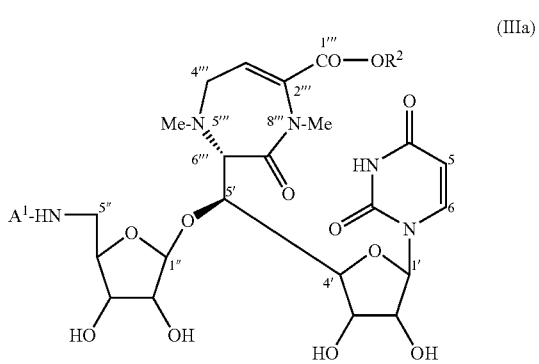

(IIIa)

wherein $R^2$ has the same meaning as defined above and $A^1$ is an amino-protecting group.

The resulting reaction solution containing the 5''-N-protected caprazene-1'''-ester derivative so produced is concentrated and the resulting syrupy concentrate is extracted with chloroform and then the said chloroform solution is washed with water and concentrated. The resulting residue is dissolved in chloroform and the resultant chloroform solution is purified by subjecting it to a silica-gel column chromatography with the development with a mixed solvent of chloroform-methanol (10:1). The eluate fractions containing the desired product from the column are concentrated to give a 5''-N-protected-caprazene-1'''-ester derivative of the formula (IIIa) as a solid. The 5''-N-protected-caprazene-1'''-ester derivative of the formula (IIIa) has been found to have an antibacterial activity against bacteria.

It has further been found that when the 5''-N-protected-caprazene-1'''-ester derivative of the formula (IIIa) is treated in the same manner as described above, for the elimination of the amino-protecting group, the 5''-N-protecting group ($A^1$) can be eliminated, thus to produce a caprazene-1'''-ester derivative represented by the following general formula (IIIb)

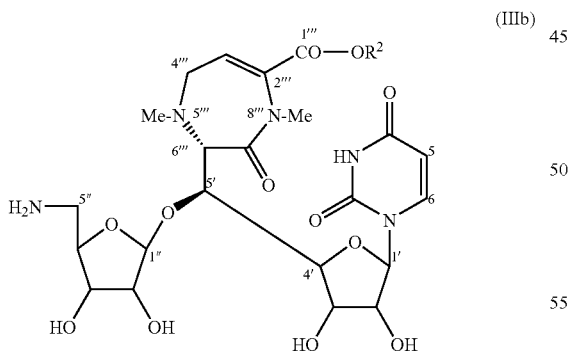

(IIIb)

wherein $R^2$ has the same meaning as defined above. The caprazene-1'''-ester derivative of the formula (IIIb), too, has been found to have an antibacterial activity against bacteria.

According to a fourth aspect of this invention, therefore, there are provided a caprazene-1'''-ester derivative and a 5''-N-alkoxycarbonyl or a 5''-N-aralkyloxycarbonyl derivative thereof which are each represented by the following general formula (III):

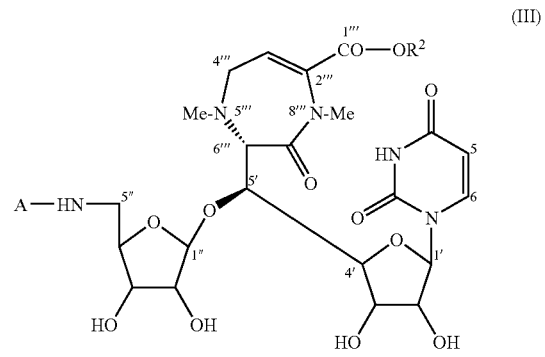

(III)

wherein Me is methyl group, $R^2$ is a straight chain or a substantially straight chain alkyl group of 5-21 carbon atoms or a straight chain or a substantially straight chain alkenyl group of 5-21 carbon atoms or an alkynyl group of 5-21 carbon atoms and A is hydrogen atom or an amino-protecting group which is an alkoxycarbonyl group, particularly tert-butoxycarbonyl group, or an aralkyloxycarbonyl group, particularly benzyloxycarbonyl group, or a pharmaceutically acceptable acid addition salt thereof.

In the 5''-N-unprotected or 5''-N-protected caprazene-1'''-ester derivative having the general formula (III), a straight chain or a substantially straight chain alkyl or alkenyl group of 5-21 carbon atoms for $R^2$ each may be the same as the alkyl or alkenyl group defined for $R^1$ in the caprazene-1'''-amide derivative having the general formula (II), respectively. An alkynyl group of 5-21 carbon atoms for $R^2$ may be pentynyl group, hexynyl group, heptynyl group, octynyl group, nonynyl group, decynyl group and so on.

Concrete examples of the caprazene-1'''-ester derivative of the following formula (IIIb) which are included within the 5''-N-unprotected caprazene-1'''-ester derivative of the general formula (III) according to the fourth aspect of this invention are shown in the following Table 5 together with their compound codes and specific rotation data.

TABLE 5

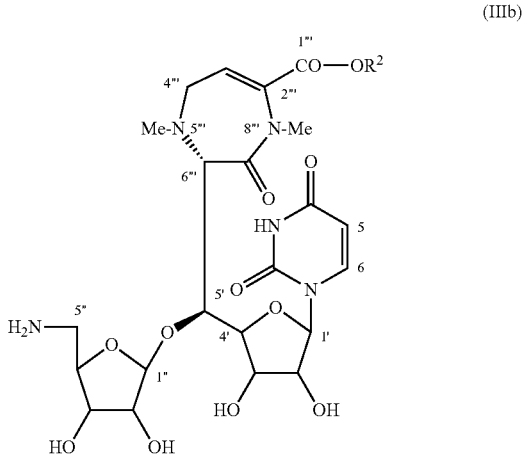

(IIIb)

| Compound code name | $R^2$ group in the formula (IIIb) | Specific rotation $[\alpha]_D^{19}$ (c 0.5, in water) |
|---|---|---|
| Compound III-AA | —(CH$_2$)$_9$CH$_3$ | +46° |
| Compound III-BB | —(CH$_2$)$_{12}$CH$_3$ | +50° |

TABLE 5-continued

| Compound III-CC | —(CH$_2$)$_{17}$CH$_3$ | +44° |
| Compound III-DD | —(CH$_2$)$_{10}$—CH═CH—CH$_2$—CH$_3$ | +42° |
| Compound III-EE | —CH$_2$—CH═CH—(CH$_2$)$_8$—CH$_3$ | +48° |
| Compound III-FF | —(CH$_2$)$_9$—CH═CH$_2$ | +48° |
| Compound III-GG | —(CH$_2$)$_2$C═C—(CH$_2$)$_5$—CH$_3$ | +40° |

TEST EXAMPLE 2

Minimum growth inhibitory concentrations (mcg/ml) of some of the caprazene-1'''-ester derivative of the formula (III) against some of microorganisms were measured on an agar culture medium by a serial dilution method according to the standard method as provided by Japanese Society of Chemotherapy. The results obtained are shown in the following Table 6.

TABLE 6

| Compound code name of the test compound (see Table 5) | Minimum growth inhibitory concentration (mcg/ml) against bacteria | | |
|---|---|---|---|
| | *Staphylococcus aureus* FDA209P | *Micrococcus luteus* FDA16 | *Mycobacterium smegmatis* ATCC607 |
| Compound III-AA | 12.5 | 1.56 | 12.5 |
| Compound III-BB | 3.13 | 3.13 | 12.5 |
| Compound III-CC | 12.5 | 6.25 | >100 |
| Compound III-DD | 6.25 | 1.56 | 25 |
| Compound III-EE | 6.25 | 1.56 | 12.5 |
| Compound III-FF | 25 | 1.56 | 12.5 |
| Compound III-GG | 50 | 6.25 | 25 |

The process for the preparation of a caprazene-1'''-ester derivative of the formula (III) according to the fourth aspect of this invention is now explained.

First of all, as explained in the third aspect of this invention, a 5"-N-alkoxycarbonyl- or 5"-N-aralkyloxycarbonyl-caprazene is prepared. Then, the 5"-N-alkoxycarbonyl- or 5"-N-aralkyloxycarbonyl-caprazene is dissolved in pyridine, and in the resulting pyridine solution, an alcohol compound of the formula (XII) above is reacted with the 2'''-carboxyl group of the 5"-N-protected caprazene according to the usual method for the esterification of carboxylic acids. The esterification reaction is conveniently carried out in the presence of N,N-bis(2-oxo-3-oxazolidinyl)phosphinic chloride as added at room temperature.

The resulting esterification reaction solution is concentrated, and the resulting concentrate is extracted with chloroform and the resulting chloroform extract is washed with water and then concentrated, to give a residue containing the desired 5"-N-protected caprazene-1'''-ester derivative. The residue is dissolved in chloroform and the resulting chloroform solution is purified by subjecting it to a silica-gel column chromatography with the development with a mixed solvent of chloroform-methanol. The eluate fractions containing the desired product from the chromatography are collected and concentrated, thus to yield the desired 5"-N-protected caprazene-1'''-ester derivative of the formula (IIIa) as a solid.

The elimination of the 5"-N-amino-protecting group can be achieved by treating the 5"-N-protected caprazene-1'''-ester derivative by the usual method for the elimination of the amino-protecting group, to produce a 5"-N-unprotected caprazene-1'''-ester derivative of the general formula (IIIb). In case where 5"-N-protecting group is Boc group, it is convenient to eliminate Boc group by dissolving the 5"-N-protected caprazene-1'''-ester derivative in methanol containing 80% TFA and stirring the resultant solution at room temperature. The resulting reaction solution is concentrated, and to the concentrate is added diethyl ether to deposit a precipitate, and the precipitate is filtered. The solid precipitate separated is washed with diethyl ether and then dried, thus to afford a 5"-N-unprotected caprazene-1'''-ester derivative of the general formula (IIIb) as a solid.

We have made further experiments on an alkaline hydrolysis of a caprazamycin at room temperature by adding an aqueous solution of an inorganic base, for example, aqueous ammonia solution or a dilute aqueous sodium hydroxide solution to an N,N-dimethylformamide solution of caprazamycin A, B or C. As a result, it has been found that the alkaline hydrolysis of caprazamycin A, B or C gives the compound represented by the following formula (IV)

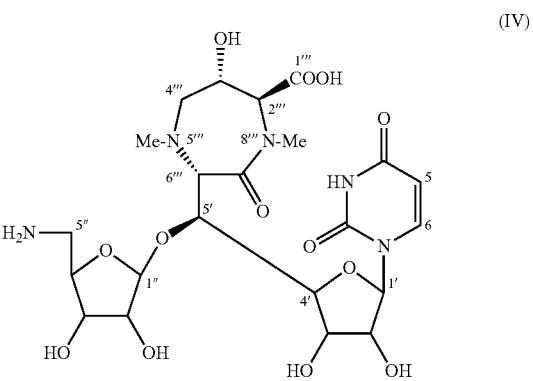

wherein Me is methyl group, and the compound is successfully isolated as a colorless solid. The crystallization of this solid from a mixture of water-methanol could give colorless crystals of the said compound [melting point 205-206° C. (with decomposition)].

We have now decided that the compound of the formula (IV) thus isolated has the steric chemical structure of the formula (IV) given above by measuring the physicochemical properties and NMR data of said compound of formula (IV) and by analyzing further this compound by X-ray powder diffractometry.

Further, by taking the physicochemical properties, $^1$H-NMR data and $^{13}$C-NMR data of said compound of formula (IV) together into consideration, we have judged it to be a novel compound and designated it as caprazol.

In addition, comparison has been made between caprazol of the formula (IV) of this invention and the aforesaid Compound II and Compound 12 both of which have sulfuric acid group —SO$_3$H and which are given by their planer structural formulae in the above literature "The Journal of Organic Chemistry", Vol. 57, No. 24, pp. 6397-6399 and 6402 and their steric structures are unknown yet. That is, when comparing the $^{13}$C-NMR data (Table III) and $^1$H-NMR data (Table IV) of Compounds II and 12 with the $^{13}$C-NMR data and $^1$H-NMR data (refer to Table 18 of Example 5 given later) of caprazol of this invention, it appears that the numerical data of the former are not necessarily consistent in part with those of the latter. Judging from this comparison, we have concluded that caprazol as prepared by us is different in some part of its steric structure and in the presence or absence of sulfuric acid group, from Compounds II and 12, and thus that caprazole is a novel compound.

According to a fifth aspect of this invention, therefore, there are provided caprazol which is the compound represented by the following formula (IV)

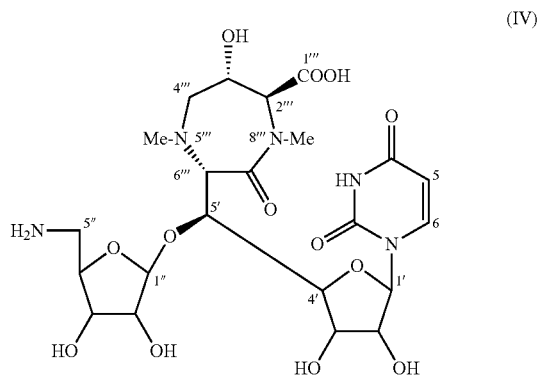

wherein Me is methyl group, and a 5″-N-alkoxycarbonyl and a 5″-N-aralkyloxycarbonyl derivative thereof.

Further, according to a sixth aspect of this invention, there is provided a process for the preparation of caprazol represented by the following formula (IV)

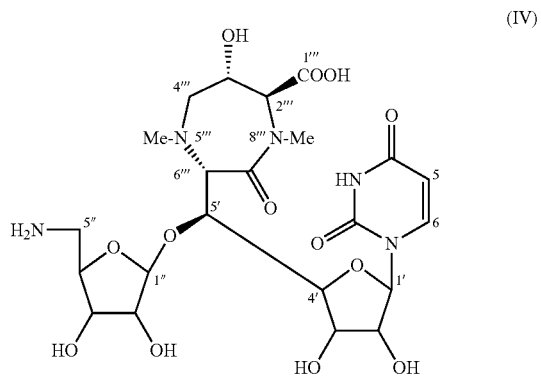

which comprises subjecting caprazamycin A, B, C, D, E, F or G or a mixture of at least two of caprazamycins A to G to a hydrolysis in an aqueous solution of an inorganic base at room temperature or under heating.

In the process according to the sixth aspect of this invention, it is preferred that at least one of caprazamycins A to G is hydrolyzed in an aqueous ammonia solution containing 15-30% by weight of ammonia ($NH_3$) at a temperature of about 40° C. or lower.

The alkaline hydrolysis reaction of caprazamycins using an aqueous dilute sodium hydroxide or potassium hydroxide solution may be carried out at room temperature or may also be carried out at an elevated temperature of 40-80° C.

After the finish of the alkaline hydrolysis reaction of caprazamycins, the resulting reaction solution is post-treated by filtering off the insolubles therefrom, concentrating the resulting filtrate, washing the resulting solid residue with acetone and drying the resulting residue, and thus there can be recovered caprazol of the formula (IV) as a colorless solid. The solid caprazol thus recovered may be dissolved in a water-methanol mixture and then crystallized to afford the desired substance as crystals. The physicochemical properties of caprazol are shown in Example 5 given hereinafter.

We have further proceeded our investigations. Thus, we have found that 5″-N-t-butoxycarbonylcaprazol or 5″-N-benzyloxy-carbonylcaprazol may be produced by a process comprising the steps of dissolving caprazol in a solution of dioxane in water and reacting caprazol in the resultant aqueous solution with triethylamine and di-t-butyl dicarbonate or N-(benzyloxycarbonyloxy)succinimide, so that the 5-amino group of the 5-amino-5-deoxy-D-ribose moiety of caprazol is t-butoxycarbonylated or benzyloxycarbonylated.

We have further succeeded in synthesizing a 5″-N-protected derivative of caprazol, generically, by introducing into the free amino group at the 5″-position of caprazol of the formula (IV) an alkoxycarbonyl group, for example, tert-butoxycarbonyl group (usually abbreviated as Boc), or an aralkyloxycarbonyl group, for example, benzyloxycarbonyl group, which is conventionally used as an amino-protecting group in the sugar chemistry.

There may be produced a 5″-N-protected caprazol-1‴-amide derivative represented by the following general formula (Va)

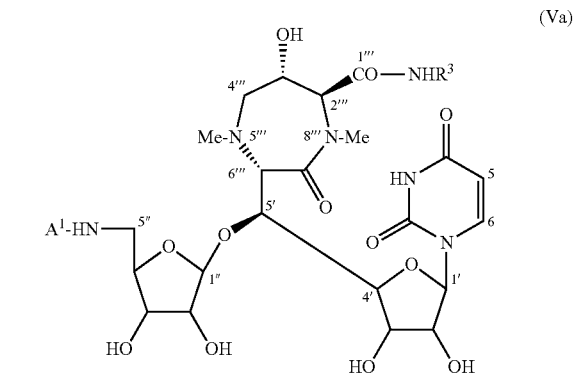

wherein Me stands for methyl group, $R^3$ is a straight chain or a substantially straight chain alkyl group of 5-21 carbon atoms, a straight chain or a substantially straight chain alkenyl group of 5-21 carbon atoms or a cycloalkyl group of 5-12 carbon atoms, and $A^1$ stands for t-butoxycarbonyl group (sometimes abbreviated as Boc) or benzyloxycarbonyl group (sometimes abbreviated as Z), by conducting a process comprising the steps of dissolving 5″-N-t-butoxycarbonyl- or benzyloxycarbonyl-caprazol in N,N-dimethylformamide, adding to the resulting solution triethylamine and N,N-bis(2-oxo-3-oxazolidinyl)phosphinic chloride, successively, and subjecting the resulting solution to a reaction with an amine compound of the following general formula (XIII)

$$R^3-NH_2 \quad (XIII)$$

wherein $R^3$ has the same meaning as defined in the formula (Va) above, in the presence of the said phosphinic chloride as added, so that there can occur the desired amidation reaction between the 2‴-carboxyl group of caprazol and the amine compound of the formula (XIII). We have further found that the protection of 5″-amino group of caprazol of the formula (IV) may also be made if the t-butoxycarbonyl group or benzyloxycarbonyl group used above is replaced by any other alkoxycarbonyl group or aralkyloxycarbonyl group which is conventionally employed as amino-protecting group in the sugar chemistry.

In cases where the 5″-N-protected caprazol-1‴-amide derivative of the formula (Va) above contains Boc group as amino-protecting group, the 5″-N-Boc group may be eliminated from the amide derivative of the formula (Va) by subjecting the said compound to a method for the elimination of the amino-protecting group conventionally employed in the sugar chemistry, for example, to a hydrolysis with trifluoroacetic acid in methanol, whereby there can be produced a caprazol-1'''-amide derivative represented by the following general formula (Vb)

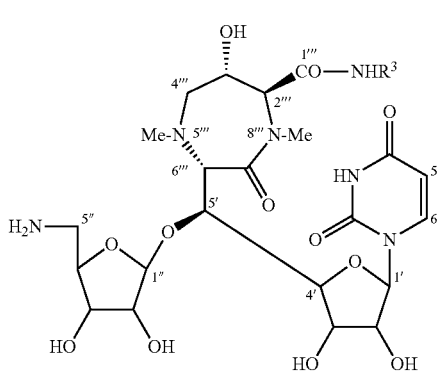

(Vb)

wherein Me and R³ have the same meanings as defined above. The caprazol-1'''-amide derivative of the general formula (Vb) thus obtained, if it be reacted with trifluoroacetic acid, hydrochloric acid, sulfuric acid or phosphoric acid, can afford the corresponding acid addition salt of the amide derivative of the formula (Vb), which is soluble in water.

Further, we have now found that the caprazol-1'''-amide derivative of the general formula (Vb) above and its 5"-N-Boc- or 5"-N—Z-protected derivative, namely 5"-N-protected caprazol-1'''-amide derivative of the general formula (Va), have antibacterial activities against a variety of bacteria, including tubercle *bacillus*.

According to a seventh aspect of this invention, therefore, there are provided a caprazol-1'''-amide derivative and its 5"-N-alkoxycarbonyl- or aralkyloxycarbonyl derivatives which are represented by the following general formula (V)

(V)

[Chemical structure of formula (V)]

wherein Me is methyl group, R³ is a straight chain or a substantially straight chain alkyl group of 5-21 carbon atoms, a straight chain or a substantially straight chain alkenyl group of 5-21 carbon atoms or a cycloalkyl group of 5-12 carbon atoms, and A is hydrogen atom or an alkoxycarbonyl group, particularly tert-butoxycarbonyl group, or an aralkyloxycarbonyl group, particularly benzyloxycarbonyl group as the amino-protecting group, or a pharmaceutically acceptable acid addition salt thereof.

In the 5"-N-unprotected or -protected caprazol-1'''-amide derivative of the general formula (V) according to the seventh aspect of this invention, an alkyl group, alkenyl group and cycloalkyl group for R³ may be the same as the alkyl group, alkenyl group and cycloalkyl group for R¹ present in the 5"-N-unprotected or -protected caprazene-1'''-amide derivative of the general formula (II) according to the third aspect of this invention, respectively.

Concrete examples of a caprazol-1'''-amide derivative of the following formula (Vb) which are included within the 5"-N-unprotected or -protected caprazol-1'''-amide derivative of the general formula (V) according to the seventh aspect of this invention are shown in the following Table 7 together with their Compound code names and specific rotation data.

TABLE 7

(Vb)

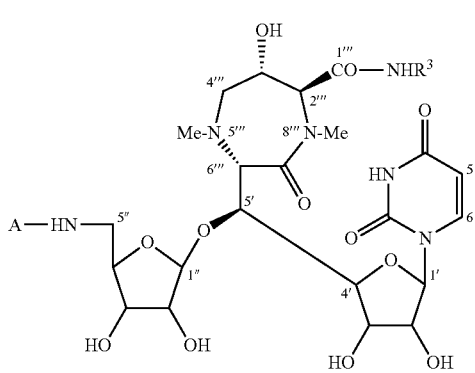

| Compound code name | R³ group in the formula (Vb) | Specific rotation [α]$_D^{19}$ (c 0.5, in methanol) |
|---|---|---|
| Compound V-A | —(CH₂)₅CH₃ | +15° |
| Compound V-B | —(CH₂)₆CH₃ | |
| Compound V-C | —(CH₂)₇CH₃ | +15° |
| Compound V-D | —(CH₂)₈CH₃ | |
| Compound V-E | —(CH₂)₉CH₃ | +12° |
| Compound V-F | —(CH₂)₁₀CH₃ | +12° |
| Compound V-G | —(CH₂)₁₁CH₃ | +12° |
| Compound V-Q | Cyclododecyl group | +35° |
| Compound V-R | Oleyl group —(CH₂)₈CH═CH(CH₂)₇CH₃ (cis-form) | +14° |

TEST EXAMPLE 3

Minimum growth inhibitory concentrations (mcg/ml) of some of the caprazol-1'''-amide derivative of the formula (V) against a variety of microorganisms were measured on an agar medium by a serial dilution method according to the standard method as provided by Japanese Society of Chemotherapy. The results obtained are shown in the following Table 8.

TABLE 8

| Compound code name of the test compound (see Table 7) | Minimum growth inhibitory concentration (mcg/ml) against bacteria | | |
|---|---|---|---|
| | *Staphylococcus aureus* FDA209P | *Micrococcus luteus* FDA16 | *Mycobacterium smegmatis* ATCC607 |
| Compound V-A | 50 | 50 | 12.5 |
| Compound V-B | | | |
| Compound V-C | 25 | 25 | 6.25 |
| Compound V-D | | | |
| Compound V-E | 25 | 25 | 6.25 |
| Compound V-F | 12.5 | 25 | 6.25 |
| Compound V-G | 12.5 | 25 | 6.25 |
| Compound V-Q | | | |
| Compound V-R | 12.5 | 25 | 6.25 |

The process for the preparation of a caprazol-1'''-amide derivative of the formula (V) is now explained.

Thus, caprazol of the formula (IV) is dissolved in water, and to the resulting aqueous solution of caprazol is added an alkoxycarbonylating reagent or an aralkyloxycarbonylating reagent conventionally used according to the amino-protecting technique well-known in organic chemistry, desirably in the form of its solution in an organic solvent such as dioxane, together with triethylamine. The reaction intended is then effected at room temperature. There is produced a 5"-N-alkoxycarbonyl- or 5"-N-aralkyloxycarbonyl-caprazol in the resulting reaction solution. An aqueous ammonia solution is added to the reaction solution and the resulting solution is concentrated under a reduced pressure. The resulting solid residue is dried under a reduced pressure, thus affording the desired 5"-N-alkoxycarbonyl- or 5"-N-aralkyloxycarbonyl-caprazol in the form of solid.

Subsequently, the 5"-N-alkoxycarbonyl- or 5"-N-aralkyl oxycarbonyl-caprazol is dissolved in N,N-dimethylformamide, and to the resultant solution is added triethylamine, thus to give a homogeneous solution of the 5"-N-protected caprazol. An amine compound $R^3$—$NH_2$ of the formula (XIII) given above is reacted with the 2'''-carboxyl group of the 5"-N-protected caprazol in the resulting solution in accordance with any conventional method for amidation of the carboxylic acid. For the amidation reaction intended, it is convenient to carry out the reaction in the presence of N,N-bis(2-oxo-3-oxazolidinyl)phosphinic chloride added, at room temperature.

The resulting amidation reaction solution is concentrated, and the syrupy concentrate obtained is extracted with chloroform and then the resulting chloroform extract is washed with water, dried and concentrated to dryness, thus affording a solid residue which contains a 5"-N-protected caprazol-1'''-amide derivative desired. The residue is dissolved in chloroform and the resultant solution is purified by subjecting it to a silica-gel column chromatography with development with a mixed solvent of chloroform-methanol-concentrated aqueous ammonia (4:1:0.1). Active fractions of the eluate from the silica-gel column are collected and concentrated, whereby there can be yielded the desired 5"-N-protected caprazol-1'''-amide derivative of the general formula (V) as a solid.

Further, the 5"-amino-protecting group can be eliminated by treating the resulting 5"-N-protected caprazol-1'''-amide derivative in accordance with the conventional technique for the elimination of amino-protecting group, thereby producing the 5"-N-unprotected caprazol-1'''-amide derivative of the general formula (V). As explained above, for the purpose of the elimination of the 5"-amino-protecting group, Boc, it is convenient to dissolve the 5"-N-protected caprazol-1'''-amide derivative in methanol containing 80% trifluoroacetic acid (TFA) and to stir the resulting solution at room temperature. The resulting reaction solution from the elimination of the amino-protecting group is concentrated, and to the resulting syrupy concentrate is added diethyl ether to deposit a precipitate which is recovered by filtration. The precipitate thus recovered is washed with diethyl ether and then dried, and thus there can be afforded the desired 5"-N-unprotected caprazol-1'''-amide derivative of the general formula (V) in the form of an addition salt of bis-trifluoroacetic acid as a solid.

We have further made a different study. It started with using the 5"-N-t-butoxycarbonylcaprazol which was prepared in the synthesis of the caprazol-1'''-amide derivatives of the general formula (V) according to the seventh aspect of this invention. Thus, the 5"-N-t-butoxycarbonylcaprazol was dissolved in N,N-dimethylformamide, and to the resultant solution were added, in order, anhydrous(±)10-camphorsulfonic acid (as acid catalyst) and dimethoxymethane, and the reaction was effected at room temperature. Thus, it has been found that by the reaction, the 2'- and 3'-hydroxyl groups and the 2"- and 3"-hydroxyl groups each of the 5"-N-t-butoxycarbonyl-caprazol are protected with isopropylidene group ($=C(CH_3)_2$; a known hydroxyl-protecting group), to produce 5"-N-t-butoxycarbonyl-2',3'; 2",3"-di-O-isopropylidene-caprazol represented by the following formula (XIV)

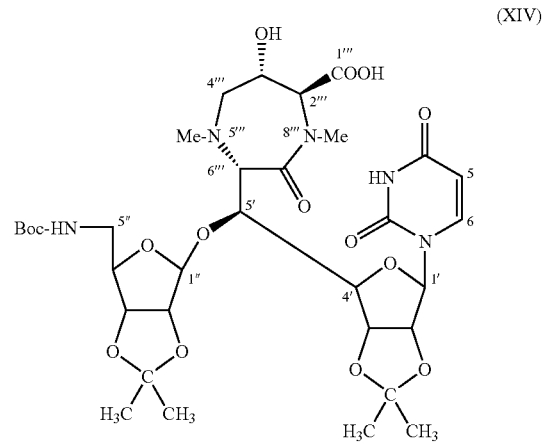

(XIV)

(see Example 9(a) given hereinafter). It has also been found that when the caprazol-N,O-protected derivative of the formula (XIV) is dissolved in N,N-dimethylformamide, and to the resultant solution are added, in order, triethylamine and an amine compound of the formula (XIII) above, and when the subsequent amidation reaction is conducted at room temperature in the same manner as that in the preparation of the caprazol-1'''-amide derivative of the general formula (V) according to the seventh aspect of this invention, there can be produced 5"-N-t-butoxycarbonyl-2',3'; 2",3"-di-O-isopropylidene-caprazol-1'''-amide derivative which is represented by the following general formula (XV)

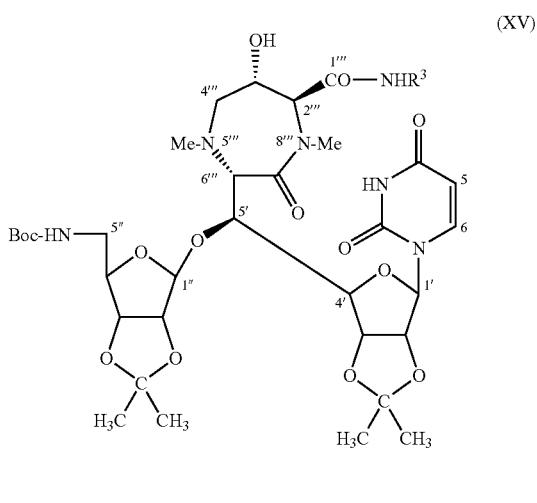

(XV)

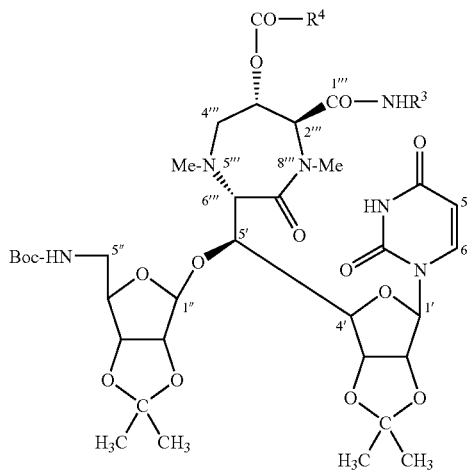

(XVII)

wherein $R^3$ is a straight chain or a substantially straight chain alkyl group of 5-21 carbon atoms or a straight chain or a substantially straight chain alkenyl group of 5-21 carbon atoms or a cycloalkyl group of 5-12 carbon atoms (see Example 9(b) hereinafter given). The resulting amidation reaction solution containing the N,O-protected caprazol-1'''-amide derivative of the formula (XV) is concentrated to dryness, and the residue obtained is extracted with chloroform and then the chloroform extract is washed with water, dried and concentrated to dryness. The resulting solid residue is dissolved in chloroform and the resulting solution is purified by subjecting it to a silica-gel column chromatography by development with a mixed solvent of chloroform-methanol (50:1). The eluate fractions containing the desired product from the silica-gel column are collected and concentrated, and thus there can be recovered the N,O-protected caprazol-1'''-amide derivative of the formula (XV).

Subsequently, the N,O-protected caprazol-1'''-amide derivative of the formula (XV) is dissolved in dichloromethane, and to the resultant solution are added 4-dimethylaminopyridine and an acid chloride of the following formula (XVI)

wherein $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms, and the reaction intended is conducted under ice-cooling. Thus, the 3'''-hydroxyl group of the N,O-protected caprazol-1'''-amide derivative of the formula (XV) is acylated with the acid chloride of the formula (XVI), whereby there can be produced a 5''-N-t-butoxycarbonyl-2',3'; 2'',3''-di-O-isopropylidene-caprazol-1'''-amide-3'''-ester derivative represented by the following general formula (XVII)

wherein $R^3$ and $R^4$ have the same meanings as defined above.

To the resulting acylation reaction solution containing the N,O-protected caprazol-1'''-amide-3'''-ester derivative of the formula (XVII) is added a small amount of methanol to decompose the residual reagent. Then the reaction solution is diluted with chloroform and the resulting solution is washed with an aqueous potassium hydrogen sulfate and water, and then the so washed solution is dried and concentrated to dryness. The resulting residue is dissolved in chloroform and the resultant solution is purified by subjecting it to a silica-gel column chromatography [at first, washing with chloroform, followed by developing with chloroform-methanol (150:1)]. There can thus be recovered the derivative of the formula (XVII) by concentrating the eluate fractions containing the derivative of the formula (XVII).

Thereafter, the elimination of the 5''-t-butoxycarbonyl group and the two isopropylidene groups ($=C(CH_3)_2$) can be effected by treating the derivative of the formula (XVII) with trifluoroacetic acid in methanol, thus to afford the caprazol-1'''-amide-3'''-ester derivative of the general formula (VI) given below. The resulting reaction solution from the treatment with trifluoroacetic acid for the deprotection of the protecting groups is then concentrated to dryness and the residue is washed with diethyl ether, whereby an addition salt of trifluoroacetatic acid of the caprazol-1'''-amide-3'''-ester derivative of the formula (VI) can be recovered. The caprazol-1'''-amide-3'''-ester derivative of the formula (VI) has been found also to possess antibacterial activities against bacteria.

According to an eighth aspect of this invention, therefore, there is provided a caprazol-1'''-amide-3'''-ester derivative represented by the following general formula (VI)

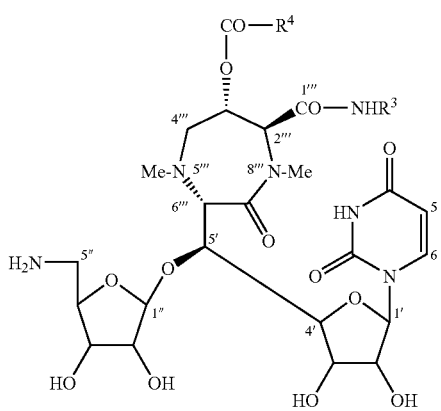

(VI)

wherein Me is methyl group, $R^3$ is a straight chain or a substantially straight chain alkyl group of 5-21 carbon atoms or a straight chain or a substantially straight chain alkenyl group of 5-21 carbon atoms or a cycloalkyl group of 5-12 carbon atoms, $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms, or a pharmaceutically acceptable acid addition salt thereof.

Some typical examples of a caprazol-1'''-amide-3'''-ester derivative of the general formula (VI) according to the eighth aspect of this invention are shown in the following Table 9 together with the Compound code names and their specific rotation data.

TEST EXAMPLE 4

Minimum growth inhibitory concentrations (mcg/ml) of some of the caprazol-1'''-amide-3'''-ester derivative of the formula (VI) against a variety of microorganisms were measured on an agar medium by a serial dilution method according to the standard method as provided by Japanese Society of Chemotherapy. The results obtained are shown in the following Table 10.

TABLE 10

| Compound code name of the test compound (see Table 9) | Minimum growth inhibitory concentration (mcg/ml) against bacteria | | |
|---|---|---|---|
| | *Staphylococcus aureus* FDA209P | *Micrococcus luteus* FDA16 | *Mycobacterium smegmatis* ATCC607 |
| Compound VI-A | 25 | 25 | 12.5 |
| Compound VI-B | | | |
| Compound VI-C | 12.5 | 6.25 | 6.25 |
| Compound VI-D | | | |
| Compound VI-E | 12.5 | 6.25 | 6.25 |
| Compound VI-F | 12.5 | 3.13 | 6.25 |
| Compound VI-G | 25 | 3.13 | 6.25 |
| Compound VI-Q | 12.5 | 3.13 | 6.25 |
| Compound VI-R | 25 | 3.13 | 6.25 |

We have further made a different investigation. Thus, the 5''-N-t-butoxycarbonyl-2',3'; 2'',3''-di-O-isopropylidene-caprazol of the formula (XIV) prepared as above is dissolved in

TABLE 9

(VI)

| Compound code name | $R^3$ group in the formula (VI) | $R^4$ group in the formula (VI) | Specific rotation $[\alpha]_D^{21}$ (c 0.5, in methanol) |
|---|---|---|---|
| Compound VI-A | —(CH$_2$)$_5$CH$_3$ | —(CH$_2$)$_5$CH$_3$ | +6° |
| Compound VI-B | —(CH$_2$)$_6$CH$_3$ | —(CH$_2$)$_6$CH$_3$ | |
| Compound VI-C | —(CH$_2$)$_7$CH$_3$ | —(CH$_2$)$_7$CH$_3$ | +6° |
| Compound VI-D | —(CH$_2$)$_8$CH$_3$ | —(CH$_2$)$_8$CH$_3$ | |
| Compound VI-E | —(CH$_2$)$_9$CH$_3$ | —(CH$_2$)$_9$CH$_3$ | +5° |
| Compound VI-F | —(CH$_2$)$_{10}$CH$_3$ | —(CH$_2$)$_{10}$CH$_3$ | +6° |
| Compound VI-G | —(CH$_2$)$_{11}$CH$_3$ | —(CH$_2$)$_{10}$—CH$_3$ | +6° |
| Compound VI-Q | Cyclododecyl group | —(CH$_2$)$_{10}$—CH$_3$ | +24° |
| Compound VI-R | —(CH$_2$)$_8$CH═CH(CH$_2$)$_7$CH$_3$ (cis-form) | —(CH$_2$)$_{10}$—CH$_3$ | +5° | dichloromethane, and to the resultant solution are added 4-dimethylamino-pyridine and an acid chloride of the following formula (XVI)

 (XVI)

wherein $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms, and the reaction intended is effected under ice-cooling. So, The 3'''-hydroxyl group of the N,O-protected caprazol of the formula (XIV) is acylated with the acid chloride of the formula (XVI), and thus there can be yielded a 5''-N-t-butoxycarbonyl-2',3'; 2'',3''-di-O-isopropylidene-caprazol-3'''-ester derivative represented by the following general formula (XVIII)

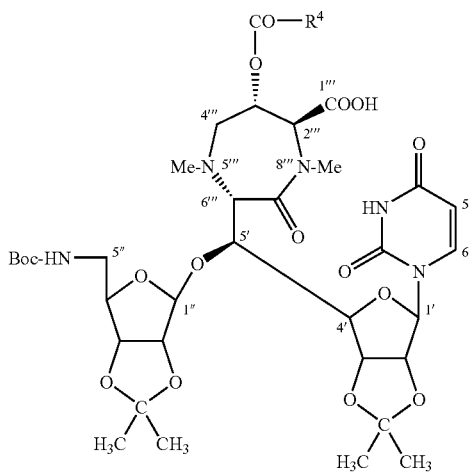

(XVIII)

wherein $R^4$ has the same meaning as defined above.

To the resulting acylation reaction solution containing the N,O-protected caprazol-3'''-ester derivative of the formula (XVIII) is added a small amount of methanol to decompose the residual reagent. Then, the resulting solution is diluted with chloroform and the resulting solution is washed with an aqueous potassium hydrogen sulfate solution and water, in order, and the so washed solution is dried and concentrated to dryness. Thus, there can be recovered the N,O-protected-3'''-ester derivative of the formula (XVIII) as a solid.

Subsequently, the N,O-protected-3'''-ester derivative of the formula (XVIII) is treated with trifluoroacetic acid in methanol, thereby to eliminate the 5''-t-butoxycarbonyl group (Boc) and the two isopropylidene groups, and thus there can be produced a caprazol-3'''-ester derivative represented by the following general formula (XIX)

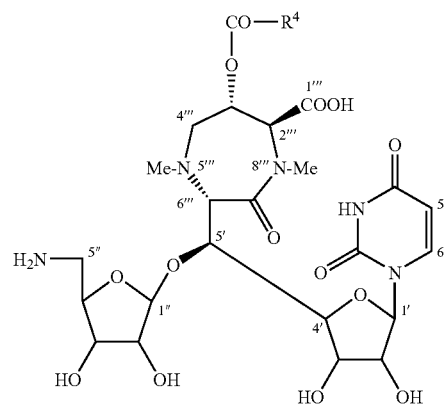

(XIX)

wherein $R^4$ has the same meaning as defined above. The resulting reaction solution containing the caprazol-3'''-ester derivative of the formula (XIX) from the deprotecting treatment with trifluoroacetic acid is concentrated to dryness and the resulting residue is washed with diethyl ether, and thus there can be recovered an addition salt of trifluoroacetic acid of a caprazol-3'''-ester derivative of the formula (XIX). The caprazol-3'''-ester derivative of the formula (XIX) has been found also to have antibacterial activities against bacteria.

In an another study, the N,O-protected caprazol of the formula (XIV) above is dissolved in N,N-dimethylformamide, and to the resultant solution are added successively triethylamine and N,N-bis(2-oxo-3-oxazolidinyl)phosphinic chloride, and further added as an esterifying reagent an alkanol of the following formula (XX)

 (XX)

wherein $R^7$ is an alkyl group of 1-21 carbon atoms, and the reaction intended is conducted at room temperature. Thus, the 2'''-carboxyl group of the N,O-protected caprazol of the formula (XIV) can be esterified to produce a 5''-N-t-butoxycarbonyl-2',3'; 2'',3''-di-O-isopropylidene-caprazol-1'''-ester derivative represented by the following general formula (XXI)

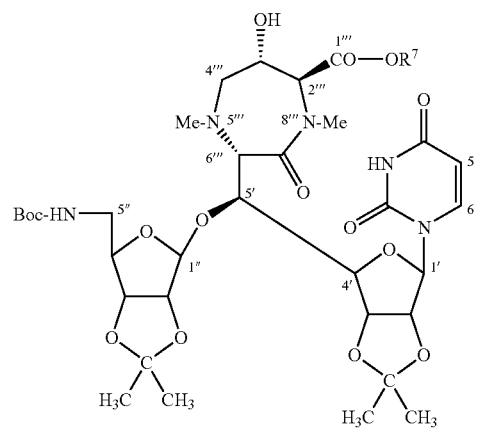

(XXI)

The resulting esterifying reaction solution is concentrated to dryness and the resulting residue is extracted with chloroform. The chloroform extract is washed with water, dried and concentrated to dryness, and the resulting residue is dissolved in chloroform. The chloroform solution is purified by subjecting it to a silica-gel column chromatography with development with chloroform-methanol (50:1). The desired eluate fractions are collected and concentrated to dryness, and thus there can be recovered the desired N,O-protected caprazol-1'''-ester derivative of the formula (XXI).

The N,O-protected caprazol-1'''-ester derivative of the formula (XXI) is then dissolved in dichloromethane, and to the resulting solution are added 4-dimethylaminopyridine and an acid chloride of the following formula (XVI)

$$Cl—CO—R^4 \quad (XVI)$$

wherein $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms. The reaction intended is effected wherein $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms. The reaction intended is effected under ice-cooling. Thus, the 3'''-hydroxyl group of the N,O-protected caprazol-1'''-ester derivative of the formula (XXI) can be acylated with the acid chloride to produce a 5"-N-t-butoxycarbonyl-2',3'; 2",3"-di-O-isopropylidene-caprazol-1'''-ester-3'''-ester derivative represented by the following general formula (XXII)

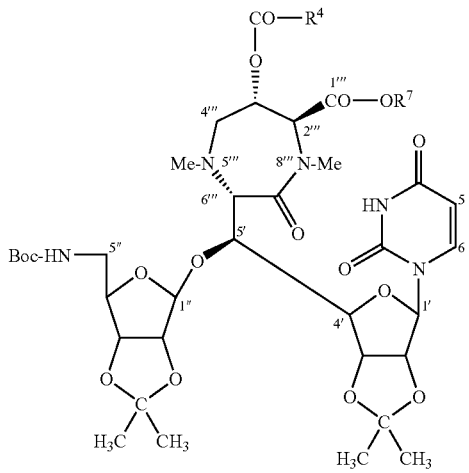

(XXII)

wherein $R^4$ and $R^7$ have the same meanings as defined above.

To the resulting acylation reaction solution containing the N,O-protected caprazol-1'''-ester-3'''-ester derivative of formula (XXII) is added a small amount of methanol to decompose the residual reagent. Then, the solution is diluted with chloroform and the resulting diluted solution is washed with an aqueous potassium hydrogen sulfate solution and water, and the solution thus washed is dried and concentrated to dryness. The resulting residue is dissolved in chloroform and the resulting solution is purified by subjecting it to a silica-gel column chromatography in the same manner as above. There can be recovered a 1'''-ester-3'''-ester derivative of the formula (XXII) by concentrating the eluate fractions containing the 1'''-ester-3'''-ester derivative of the formula (XXII).

Subsequently, for the purpose of deprotection of the 1'''-ester-3'''-ester derivative of the formula (XXII), the treatment of this derivative with trifluoroacetic acid is carried out in methanol in the same manner as that above-mentioned. Thus, the 5"-t-butoxycarbonyl group and the two isopropylidene groups can be eliminated to produce a caprazol-1'''-ester-3'''-ester derivative of the following general formula (XXIII)

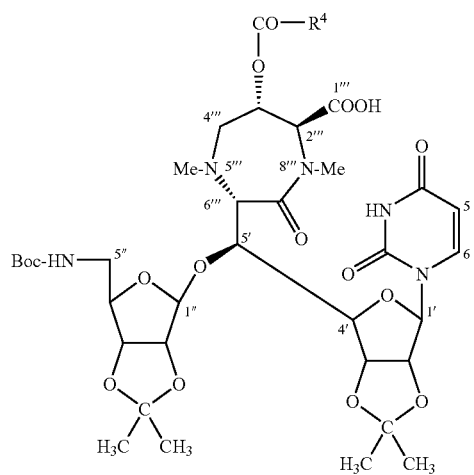

(XVIII)

wherein $R^4$ and $R^7$ have the same meanings as defined above. The resulting reaction solution from the deprotection treatment with trifluoroacetic acid is concentrated to dryness, and the resulting residue is washed with diethyl ether, and thus there can be recovered an addition salt of trifluoroacetatic acid of the caprazol-1'''-ester-3'''-ester derivative of the formula (XXIII). The caprazol-1'''-ester-3'''-ester derivative of the formula (XXIII) as well as the caprazol-3'''-ester derivative of the formula (XIX) has been found also to have antibacterial activities against bacteria.

According to a ninth aspect of this invention, therefore, there is provided a caprazol-3'''-ester derivative or a caprazol-1'''-ester-3'''-alkyl ester derivative which is represented by the following general formula (VII)

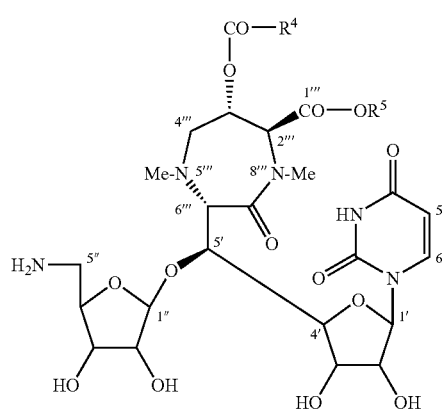

(VII)

wherein Me is methyl group, $R^4$ is a straight chain or a substantially straight chain alkyl group of 5-21 carbon atoms or a straight chain or a substantially straight chain alkenyl group of 5-21 carbon atoms or an alkynyl group of 5-21 carbon atoms and $R^5$ is hydrogen atom or an alkyl group of 1-21 carbon atoms, or a pharmaceutically acceptable acid addition salt thereof.

Some concrete examples of a caprazol-3'''-ester derivative or a caprazol-1'''-ester-3'''-ester derivative of the general formula (VII) according to the ninth aspect of this invention are shown in the following Table 11 together with their compound code names and specific rotation data.

TABLE 11

(VII)

[Structure of compound VII showing uridine derivative with diazepine ring system bearing CO—R⁴ and CO—OR⁵ ester groups]

| Compound code name | R⁴ group in the formula (VII) | R⁵ group in the formula (VII) | Specific rotation $[\alpha]_D^{20}$ |
|---|---|---|---|
| Compound VII-A | —(CH$_2$)$_5$CH$_3$ | —H | +16° (c 0.5, in DMSO) |
| Compound VII-B | —(CH$_2$)$_6$CH$_3$ | —H | +16° (c 0.5, in DMSO) |
| Compound VII-C | —(CH$_2$)$_7$CH$_3$ | —H | +16° (c 0.5, in DMSO) |
| Compound VII-D | —(CH$_2$)$_8$CH$_3$ | —H | +17° (c 0.5, in DMSO) |
| Compound VII-E | —(CH$_2$)$_9$CH$_3$ | —H | +17° (c 0.5, in DMSO) |
| Compound VII-F | —(CH$_2$)$_{10}$CH$_3$ | —H | +17° (c 0.5, in DMSO) |
| Compound VII-G | —(CH$_2$)$_{10}$CH$_3$ | —CH$_3$ | +6° (c 1, in methanol) |
| Compound VII-Q | Cyclododecyl group | —H |  |
| Compound VII-R | —(CH$_2$)$_7$CH=CH(CH$_2$)$_7$CH$_3$ (cis-form) | —H | +14° (c 0.5, in DMSO) |

TEST EXAMPLE 5

Minimum growth inhibitory concentrations (mcg/ml) of some of the caprazol-3′″-ester derivative or caprazol-1′″-ester-3′″-ester derivative of the formula (VII) against a variety of microorganisms were measured on an agar medium by a serial dilution method according to the standard method as provided by Japanese Society of Chemotherapy. The results obtained are shown in the following Table 12.

TABLE 12

| Compound code name of the test compound (see Table 11) | Minimum growth inhibitory concentration (mcg/ml) against bacteria | | |
|---|---|---|---|
| | *Staphylococcus aureus* FDA209P | *Micrococcus luteus* FDA16 | *Mycobacterium smegmatis* ATCC607 |
| Compound VII-A | 25 | >50 | 1.56 |
| Compound VII-B | 12.5 | >50 | 1.56 |
| Compound VII-C | 12.5 | >50 | 0.78 |
| Compound VII-D | 3.13 | 3.13 | 0.78 |
| Compound VII-E | 1.56 | 1.56 | 0.39 |
| Compound VII-F | 0.78 | 3.13 | 0.78 |
| Compound VII-G | >100 | >100 | 50 |
| Compound VII-Q | | | |
| Compound VII-R | 1.56 | 3.13 | 6.25 |

We have further proceeded with a different investigation. Thus, caprazol is treated with methylamine in an aqueous solution of caprazol of the formula (IV) at room temperature for a long period of time. It has been found that by this treatment reaction, the diazepinone ring moiety of caprazol can be opened to produce an uridine derivative of the following formula (IX)

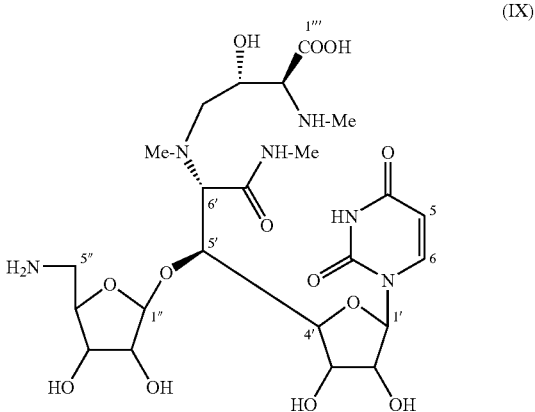

(IX)

The resulting reaction solution from the reaction of caprazol with methylamine is concentrated under a reduced pressure and dried, and the resulting residue is washed with a mixed solvent of chloroform-diethyl ether and dried. The solid thus obtained is dissolved in water. The resulting aqueous solution is purified by subjecting it to a chromatography through a column packed with Amberlite CG-50 (NH$_4$⁺ form) with the development with water. The eluate fractions containing the desired compound are collected, concentrated under a reduced pressure and dried, to afford the uridine derivative of the formula (IX) in a pure state.

Further, when 5"-N-t-butoxycarbonyl-caprazol as mentioned above is treated in an aqueous solution thereof with methylamine at room temperature for a long period of time, it has been found that there can be produced in its aqueous solution, as a 5"-N-t-butoxycarbonylated product of the uridine derivative of the formula (IX), the compound of the following formula (IXa)

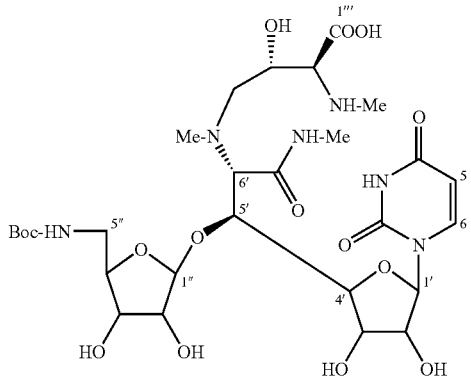

(IXa)

The said reaction solution is concentrated under a reduced pressure and dried, to recover the compound of the formula (IXa).

The compound of the formula (IXa) is then dissolved in N,N-dimethylformamide, and to the resulting solution is added an excess amount of an alkylisocyanate of the following general formula (XXIV)

$R^6$—NCO  (XXIV)

wherein $R^6$ is a straight chain or a substantially straight chain alkyl group of 1-21 carbon atoms. The reaction intended is then effected at room temperature. It was thought that by this reaction, there was produced a compound which is to be assumed to have the structure of the following general formula (XXV)

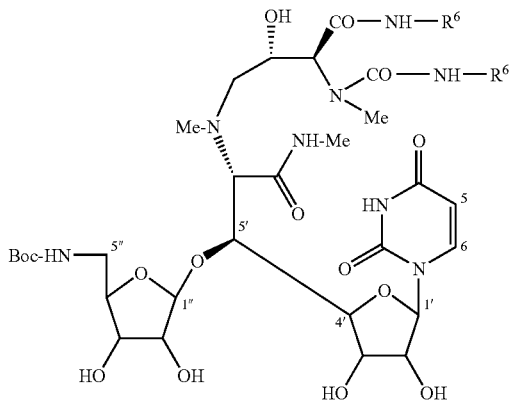

(XXV)

wherein $R^6$ is the same alkyl group as stated above.

After the reaction between the compound of the formula (IXa) and an alkylisocyanate of the formula (XXIV) was effected at room temperature for a long period of time, there was deposited a precipitate from the resulting reaction solution. The precipitate was filtered off and the filtrate was concentrated under a reduced pressure. The resulting concentrated solution was extracted with chloroform, and the chloroform extract was washed with an aqueous saturated sodium sulfate solution, dried and further concentrated and dried under a reduced pressure. The resulting solid residue was washed with hexane and dried, to obtain a colorless solid. The colorless solid so obtained was purified by a silica-gel column chromatography (developing with chloroform-water-methanol=9:1:0.1) and then chemically analyzed. The solid was recognized to be an imidazolidinone derivative which is a product derived from the compound of the estimated formula (XXV) by a partial cyclization thereof, and which is represented by the following general formula (VIIIa)

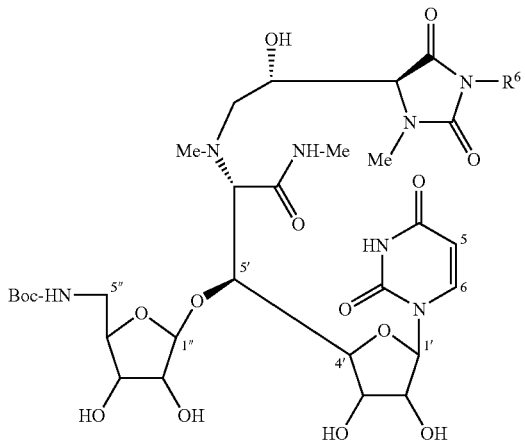

(VIIIa)

wherein $R^6$ has the same meaning as defined above.

In order to eliminate the amino-protecting group (Boc) from the imidazolidinone derivative of the formula (VIIIa), the derivative of the formula (VIIIa) was treated with trifluoroacetic acid in methanol. The resulting reaction solution of the elimination reaction was concentrated to dryness under a reduced pressure, and the resulting residue was washed with diethyl ether and then dried, to afford an addition salt of trifluoroacetatic acid of an imidazolidinone derivative of the undermentioned general formula (VIII). This derivative of the formula (VIII) was given CP-IM as code name. The imidazolidinone derivative of the formula (VIII) is also found to have antibacterial activities against bacteria.

According to a tenth aspect of this invention, therefore, there is provided an imidazolidinone derivative, CP-IM, which is represented by the following general formula (VIII)

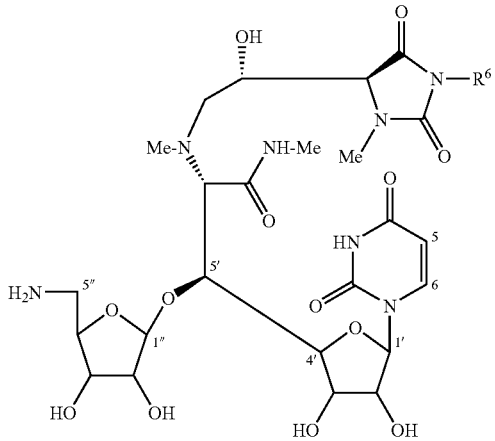

(VIII)

wherein Me is methyl group and $R^6$ is a straight chain or a substantially straight chain alkyl group of 1-21 carbon atoms, or a pharmaceutically acceptable acid addition salt thereof.

Some concrete examples of the derivative of the general formula (VIII) according to the tenth aspect of this invention are shown in the following Table 13 together with their Compound code names and specific rotation data.

TABLE 13

(VIII)

[Chemical structure of formula (VIII)]

| Compound code name | $R^6$ group of the formula (VIII) | Specific rotation $[\alpha]_D^{20}$ (c 2, in methanol) |
|---|---|---|
| Compound VIII-A | —(CH$_2$)$_5$CH$_3$ | |
| Compound VIII-B | —(CH$_2$)$_6$CH$_3$ | |
| Compound VIII-C | —(CH$_2$)$_7$CH$_3$ | |
| Compound VIII-D | —(CH$_2$)$_8$CH$_3$ | |
| Compound VIII-E | —(CH$_2$)$_9$CH$_3$ | +12° |
| Compound VIII-F | —(CH$_2$)$_{10}$CH$_3$ | +12° |
| Compound VIII-G | —(CH$_2$)$_{11}$CH$_3$ | +13° |

TEST EXAMPLE 6

Minimum growth inhibitory concentrations (mcg/ml) of some of the derivative of the formula (VIII) against a variety of microorganisms were measured on an agar medium by a serial dilution method according to the standard method as provided by Japanese Society of Chemotherapy. The results obtained are shown in the following Table 14.

TABLE 14

| Compound code name of the test compound (see Table 13) | Minimum growth inhibitory concentration (mcg/ml) against bacteria | | |
|---|---|---|---|
| | *Staphylococcus aureus* FDA209P | *Micrococcus luteus* FDA16 | *Staphylococcus aureus* ATCC607 |
| Compound VIII-A | | | |
| Compound VIII-B | | | |
| Compound VIII-C | | | |
| Compound VIII-D | | | |
| Compound VIII-E | 25 | 6.25 | 6.25 |
| Compound VIII-F | 25 | 6.25 | 6.25 |
| Compound VIII-G | 25 | 6.25 | 12.5 |

It is to be added that the uridine derivative of the formula (IX) and the 5"-N-t-butoxycarbonyl-uridine derivative of the formula (IXa) above do not have a significant antibacterial activity, but both the derivatives are novel compounds useful as intermediate compounds for use in the synthesis of the derivative of the formula (VIII).

According to an eleventh aspect of this invention, therefore, there is provided an uridine derivative represented by the following formula (IX)

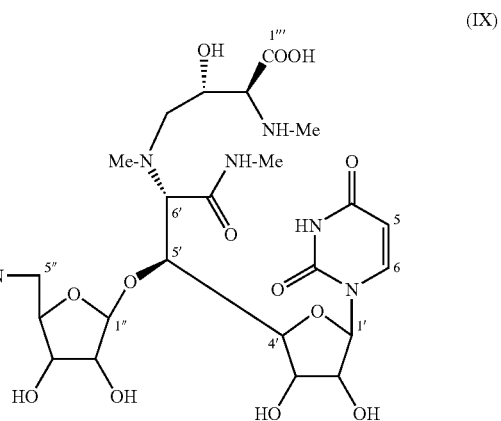

(IX)

wherein Me is methyl group, or its 5"-N-t-butoxycarbonyl derivative.

As described hereinbefore, the caprazene-1'''-amide derivative of the formula (II) according to the third aspect of this invention, the caprazene-1'''-ester derivative of the formula (III) according to the fourth aspect of this invention, the caprazol-1'''-amide derivative of the formula (V) according to the seventh aspect of this invention, the caprazol-1'''-amide-3'''-ester derivative of the formula (VI) according to the eighth aspect of this invention, the caprazol-3'''-ester derivative or the caprazol-1'''-ester-3'''-ester derivative of the formula (VII) according to the ninth aspect of this invention or the imidazolidinone derivative, CP-IM, of the formula (VIII) according to the tenth aspect of this invention, or acid addition salts of these derivatives have antibacterial activities against a variety of bacteria, so that at least one of these derivatives or their acid addition salts can be used as active ingredient and can be associated with a pharmaceutically acceptable carrier or carriers to form a pharmaceutical or medicinal composition, which may be particularly an antibacterial composition. Pharmaceutically acceptable liquid carriers conventionally used may, for example, include ethanol, aqueous ethanol, water, physiological salt solution and the like, and solid carriers may, for example, be crystalline cellulose, starch and the like.

The caprazene derivative of the formula (II) or the formula (III), the caprazol derivative of the formula (V) or the formula (VI) or the formula (VII) or the imidazolidinone derivatives of the formula (VIII) or acid addition salts of these derivatives may be administered, either by itself or in the form of a pharmaceutical composition containing it as active ingredient, through any appropriate route.

According to a further aspect of this invention, therefore, there is provided a pharmaceutical composition comprising as active ingredient at least one of a caprazene-1'''-amide derivative of the formula (II) or a caprazene-1'''-ester derivative of the formula (III) or a caprazol-1'''-amide derivative of the formula (V) or a caprazol-1'''-amide-3'''-ester derivative of the formula (VI) or a caprazol-3'''-ester derivative or a caprazol-1'''-ester-3'''-ester derivative of the formula (VII) or an imidazolidinone derivative, CP-IM, of the formula (VIII), or an acid addition salt of these derivative, and a pharmaceutically acceptable liquid or solid carrier or carriers, in combination with the active ingredient.

BEST MODE FOR CARRYING OUT THE INVENTION

Now, an illustrative experiment of the preparation of caprazene of the formula (I) according to the first aspect of this invention by the process according to the second aspect of this invention is concretely explained with reference to the following Example 1

Synthesis of Caprazene from Caprazamycin B

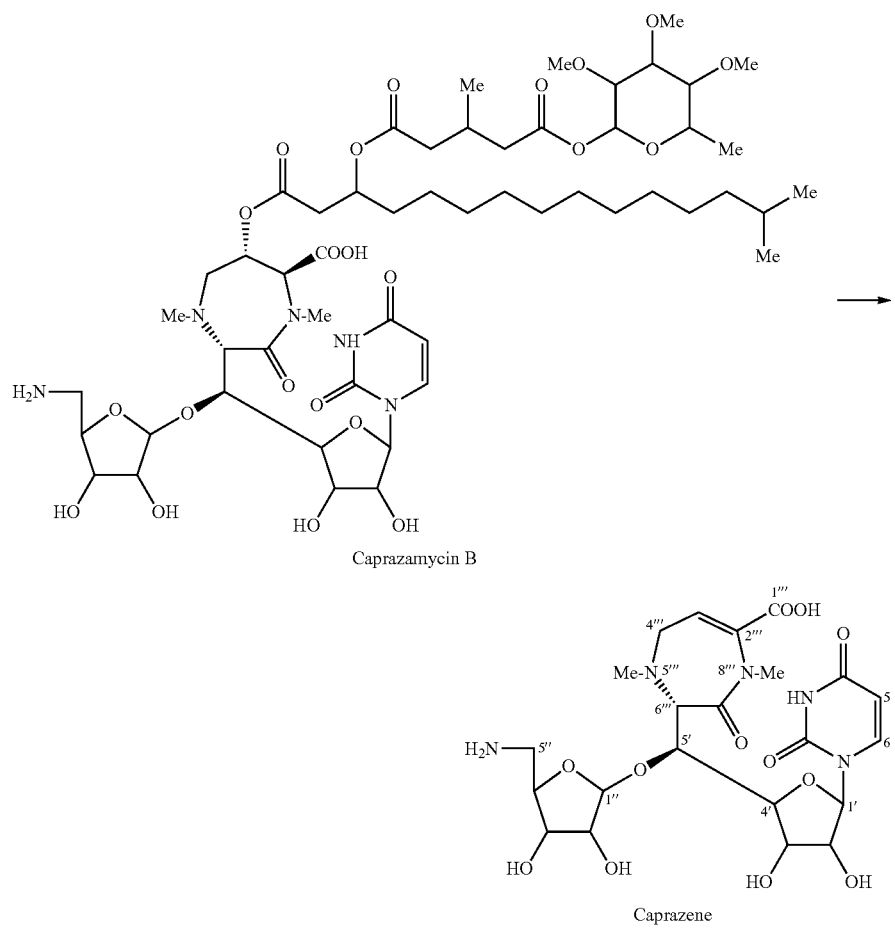

Caprazamycin B (200 mg) was dissolved in 80% aqueous acetic acid solution (6 ml) and the resulting solution was heated at 70° C. for 2 hours. The resulting reaction solution was concentrated, and to the resulting syrupy concentrate was added an amount of acetone. The precipitate so deposited was recovered by filtration, washed with acetone and dried. Thus, there was afforded caprazene (96.3 mg) as a colorless solid. Yield; 99%.

Melting point: 210-211° C. (with decomposition) (after the crystallization from water-acetone)

Specific rotation: $[\alpha]^{19} +85°$ (c 0.5, $H_2O$)

$^1$H-NMR spectrum and $^{13}$C-NMR spectrum of caprazene are shown in the following Table 15.

TABLE 15

| Position | $^1$H-NMR data of caprazene (δ, ppm in $D_2O$) | Position | $^{13}$C-NMR data of caprazene (δ, ppm in $D_2O$) |
|---|---|---|---|
| 5 | 5.82, d, J = 8 Hz | 2 | 151.7 |
| 6 | 7.69, d, J = 8 Hz | 4 | 166.8 |
|   |   | 5 | 102.0 |
|   |   | 6 | 142.4 |
| 1' | 5.62, d, J = 2.5 Hz |   |   |
| 2' | 4.28, dd, J = 2.5, 5 Hz | 1' | 91.4 |
| 3' | 4.12, dd, J = 5, 8 Hz | 2' | 73.9 |
| 4' | 4.24, br. d, J = 8 Hz | 3' | 69.4 |
| 5' | 4.34, dd, J = 2, 9.5 Hz | 4' | 82.7 |
|   |   | 5' | 77.0 |
| 1" | 5.22, slightly br. s |   |   |
| 2" | 4.13, br. d, J = 5 Hz |   |   |

TABLE 15-continued

| Position | $^1$H-NMR data of caprazene (δ, ppm in $D_2O$) | Position | $^{13}$C-NMR data of caprazene (δ, ppm in $D_2O$) |
|---|---|---|---|
| 3" | 4.26, dd, J = 5, 8 Hz | 1" | 110.0 |
| 4" | 4.20, m | 2" | 75.3 |
| 5"a | 3.18, dd, J = 5, 14 Hz | 3" | 70.7 |
| 5"b | 3.35, dd, J = 4, 14 Hz | 4" | 79.0 |
|   |   | 5" | 40.5 |
| 2''' |   |   |   |
| 3''' | 6.49, t, J = 7 Hz | 1''' | 169.2 |
| 4'''a | 2.94, dd, J = 7, 12.5 Hz | 2''' | 144.7 |

TABLE 15-continued

| Position | $^1$H-NMR data of caprazene (δ, ppm in $D_2O$) | Position | $^{13}$C-NMR data of caprazene (δ, ppm in $D_2O$) |
|---|---|---|---|
| 4'''b | 3.34, dd, J = 7, 12.5 Hz | 3''' | 123.5 |
| 6''' | 3.92, d, J = 9.5 Hz | 4''' | 51.5 |
| MeN-5''' | 2.42, s | 6''' | 63.6 (broad) |
| MeN-8''' | 2.99, s | 7''' | 171.3 |
|  |  | MeN-5''' | 40.5 |
|  |  | MeN-8''' | 33.2 |

Example 2

Synthesis of Caprazene from a Mixture of Caprazamycins B, C, D, E and F

A mixture (10.1 g) of caprazamycins B-F (see the general formulae (A) and (B) shown hereinbefore) was dissolved in 80% aqueous acetic acid solution (250 ml) and the resulting solution was heated at 70° C. for 2 hours. The reaction solution obtained was concentrated, and to the resulting syrupy concentrate was added an amount of acetone, and the deposited precipitate was recovered by filtration. The solid so precipitated and recovered was washed with acetone and dried, to afford caprazene (5.1 g).

Now, an illustrative experiment of the preparation of a caprazene-1'''-amide derivative of the formula (II) according to the third aspect of this invention is concretely described with reference to Example 3.

Example 3

(a) Synthesis of 5''-N-Boc-caprazene from Caprazene

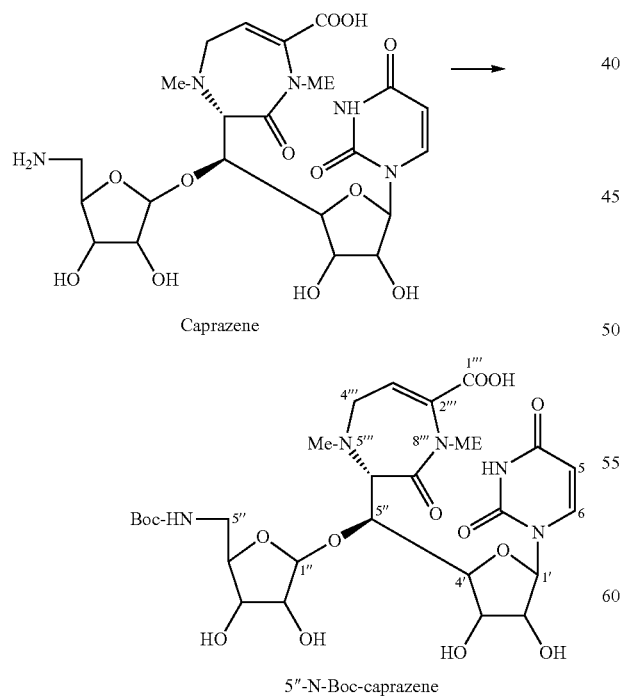

Caprazene of the formula (I) (8.14 g) was suspended in a mixed solvent (120 ml) of water-dioxane (2:1). To the resultant suspension was added triethylamine (3.7 ml) to give a homogeneous solution of caprazene. To the resulting solution was added a solution of di-t-butyl dicarbonate (3.2 g) dissolved in dioxane (5 ml), and the reaction intended was conducted at room temperature for 1 hour (for the reaction for introducing t-butoxycarbonyl group (Boc) as amino-protecting group). The reaction solution obtained was concentrated and the resulting residue was washed with ethyl acetate and dried, to afford 5''-N-Boc-caprazene (9.50 g) as a pale yellow solid. Crude yield; 99%.

$^1$H-NMR spectrum (in heavy water ($D_2O$), TMS internal standard)

δ 1.31 (3H, s, $Me_3CO$—)

2.39 (3H, slightly br. s, MeN-5''')

2.98 (3H, s, MeN-8''')

5.13 (1H, slightly br. s, H-1'')

5.62 (1H, slightly br. s, H-1')

5.77 (1H, d, H-5, $J_{5,6}$=8 Hz)

6.44 (1H, t, H-3''', J=7 Hz)

5.77 (1H, d, H-6).

(b) Synthesis of caprazene-1'''-amide Derivative from 5''-N-Boc-caprazene

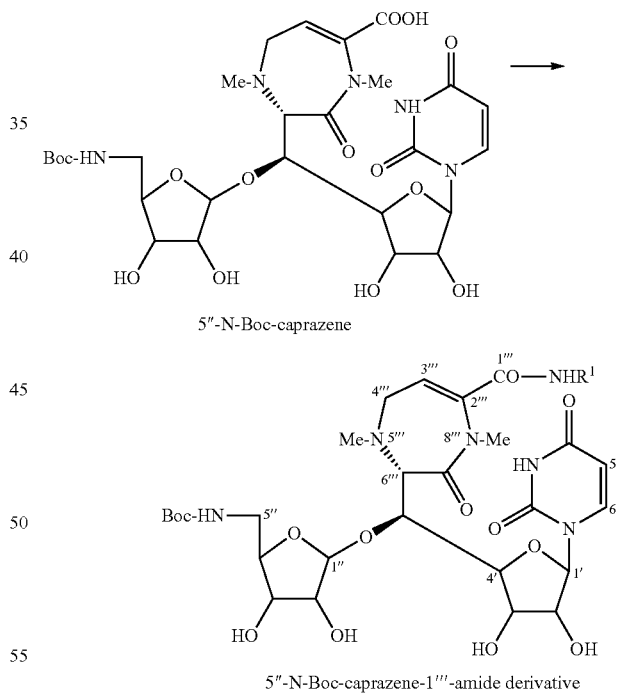

The 5''-N-Boc-caprazene obtained in Example 3(a) (150 mg) was suspended in tetrahydrofuran (6 ml). To the resulting suspension were added triethylamine (80 µl), N,N-bis(2-oxo-3-oxazolidinyl)phosphinic chloride (80 mg) and one of the various amine compounds $R^1$—$NH_2$ shown in the following Table 16 or one of various para-substituted aniline (1.1 to 1.3 molar equivalents each). The resulting mixture was stirred at room temperature for 1 hour to cause the reaction intended (for the amidation reaction).

TABLE 16

| Chemical formula | Name |
| --- | --- |
| $C_6H_{13}$—$NH_2$ | Hexylamine |
| $C_7H_{15}$—$NH_2$ | Heptylamine |
| $C_8H_{17}$—$NH_2$ | Octylamine |
| $C_9H_{19}$—$NH_2$ | Nonylamine |
| $C_{10}H_{21}$—$NH_2$ | Decylamine |
| $C_{11}H_{23}$—$NH_2$ | Undecylamine |
| $C_{12}H_{25}$—$NH_2$ | Dodecylamine |
| $C_{13}H_{27}$—$NH_2$ | Tridecylamine |
| $C_{14}H_{29}$—$NH_2$ | Tetradecylamine |
| $C_{15}H_{31}$—$NH_2$ | Pentadecylamine |
| $C_{16}H_{33}$—$NH_2$ | Hexadecylamine |
| $C_{17}H_{35}$—$NH_2$ | Heptadecylamine |
| $C_{18}H_{37}$—$NH_2$ | Octadecylamine |
| $C_{19}H_{39}$—$NH_2$ | Nonadecylamine |
| $C_{20}H_{41}$—$NH_2$ | Icocylamine |
| $C_{21}H_{43}$—$NH_2$ | Henicocylamine |
| Cyclo$(CH_2)_{12}$—$NH_2$ | Cyclododecylamine |
| $CH_3(CH_2)_7C$=$C(CH_2)_8$—$NH_2$ | Oleylamine |

Amine compound $R^1$—$NH_2$

The resulting reaction solution was concentrated and the resulting syrupy concentrate was extracted with chloroform. The chloroform extract was washed with water and then concentrated. The resulting residue was dissolved in chloroform and the chloroform solution was purified by a silica-gel column chromatography (developing solvent system: chloroform-methanol=10:1). The desired eluate fractions were collected and concentrated to dryness. Thus, there was afforded 5"-N-Boc protected derivative of each of the caprazene-1'''-amide derivatives of the formula (II) which has Compound code name shown in Table 2 given hereinbefore, as a colorless solid. Yield; 86-128 mg (the yield in the two steps from caprazene; 50-60%).

(c) Synthesis of caprazene-1'''-amide Derivative

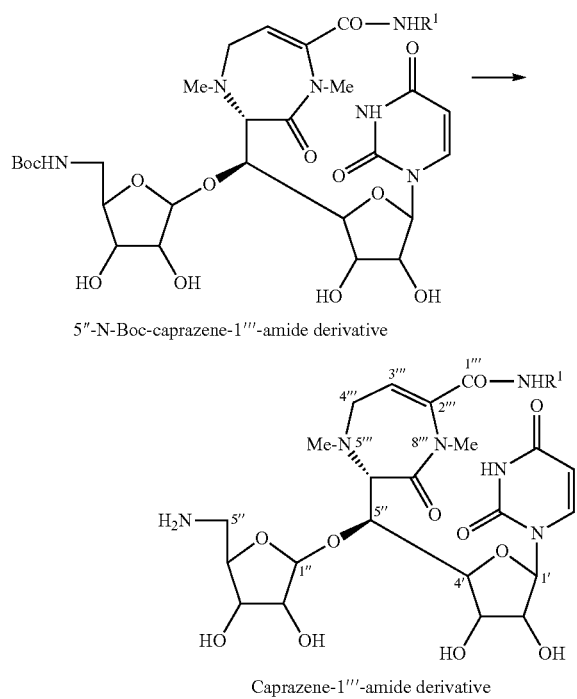

5"-N-Boc-caprazene-1'''-amide derivative

Caprazene-1'''-amide derivative

Each of the 5"-N-Boc protected derivatives of a caprazene-1'''-amide derivative obtained in Example 3 (b) (50 mg) was dissolved in methanol solution of 80% trifluoroacetic acid (1 ml). The resulting solution was subjected to the reaction at room temperature for 1 hour to eliminate the amino-protecting group (Boc). The resulting deprotection reaction solution was concentrated, and to the resulting syrupy concentrate was added an amount of diethyl ether, and the precipitate deposited was washed with diethyl ether and then dried. Thus, there were afforded caprazene-1'''-amide derivatives of the formula (II) which are Compound II-A to Compound II-R shown in Table 2-1 above, or Compound II-1 to Compound II-24 shown in Table 2-2 above, respectively, as a colorless solid. Yield; 54.5-58.0 mg (Yield as an addition salt of bis-trifluoroacetic acid; 96-99%).

$^1$H-NMR spectrum (500 MHz, in deutero-dimethylsulfoxide, TMS internal standard) of each of the Compound II-A to Compound II-R (see Table 2-1) or Compound II-1 to Compound II-24 (see Table 2-2) obtained as caprazene-1'''-amide derivatives of the formula (II) in Example 3(c) is shown below.

Compound II-A

δ 0.84 (3H, t, $CH_3(CH_2)_5NH$, J=7 Hz), 1.18~1.25 (6H, slightly br. s, $CH_3\overline{(CH_2)}_3CH_2CH_2NH$), 2.36 (3H, br. s, NMe-5'''), 2.91 (3H, s, $\overline{NMe-8'''}$), 5.10 (1H, br. s, H-1"), 5.55 (1H, d, H-1', J=1.5 Hz), 5.63 (1H, d, H-5, J=~8 Hz), 6.31 (1H, br. t, H-3''', J=~6 Hz), 7.67 (1H, br. s, H-6), 11.33 (1H, s, NH-3).

Compound II-B

δ 0.84 (3H, t, $CH_3(CH_2)_6NH$, J=7 Hz), 1.16~1.28 (8H, br. s, $CH_3(CH_2)_4\overline{CH_2CH_2}NH$), 2.36 (3H, br. s, NMe-5'''), 2.91 (3H, s, $\overline{NMe-8'''}$), 5.10 (1H, br. s, H-1"), 5.55 (1H, d, H-1', J=~1 Hz), 5.63 (1H, d, H-5, J=~8 Hz), 6.30 (1H, br. t, H-3''', J=~6 Hz), 7.67 (1H, br. d, H-6, J=~8 Hz), 11.33 (1H, s, NH-3).

Compound II-C

δ 0.85 (3H, t, $CH_3(CH_2)_7NH$, J=7 Hz), 1.18~1.28 (10H, br. s, $CH_3\overline{(CH_2)}_5\overline{CH_2CH_2}NH$), 2.36 (3H, br. s, NMe-5'''), 2.90 (3H, s, $\overline{NMe-8'''}$), 5.09 (1H br. s, H-1"), 5.55 (1H, d, H-1', J=~1.5 Hz), 5.63 (1H, d, H-5, J=~8 Hz), 6.29 (1H, br. t, H-3''', J=6 Hz), 7.67 (1H, br. s, H-6), 11.32 (1H, s, NH-3).

Compound II-D

δ 0.85 (3H, t, $CH_3(CH_2)_8NH$, J=7 Hz), 1.18~1.29 (12H, br. s, $CH_3(CH_2)_6\overline{CH_2CH_2}NH$), 2.34 (3H, br. s, NMe-5'''), 2.90 (3H, s, $\overline{NMe-8'''}$), 5.08 (1H, br. s, H-1"), 5.55 (1H, d, H-1', J=~1 Hz), 5.63 (1H, d, H-5, J=~8 Hz), 6.29 (1H, br. t, H-3''', J=~6 Hz), 7.68 (1H, br. d, H-6, J=~8 Hz), 11.32 (1H, s, NH-3).

Compound II-E

δ 0.85 (3H, t, $CH_3(CH_2)_9NH$, J=7 Hz), 1.18~1.28 (14H, br. s, $CH_3(CH_2)_7\overline{CH_2CH_2}NH$), 2.34 (3H, br. s, NMe-5'''), 2.90 (3H, s, $\overline{NMe-8'''}$), 5.09 (1H, br. s, H-1"), 5.55 (1H, d, H-1', J=~1 Hz), 5.63 (1H, d, H-5, J=~8 Hz), 6.28 (1H, br. t, H-3''', J=~6 Hz), 7.68 (1H, br. d, H-6, J=~8 Hz), 11.32 (1H, s, NH-3).

Compound II-F

δ 0.85 (3H, t, $CH_3(CH_2)_{10}NH$, J=7 Hz), 1.18~1.30 (16H, br. s, $CH_3(CH_2)_8\overline{CH_2CH_2}NH$), 2.36 (3H, br. s, NMe-5'''), 2.91 (3H, s, $\overline{NMe-8'''}$), 5.09 (1H, br. s, H-1"), 5.55 (1H, d, H-1', J=~1 Hz), 5.63 (1H, d, H-5, J=8 Hz), 6.29 (1H, br. t, H-3''', J=~6 Hz), 7.67 (1H, br. d, H-6, J=8 Hz), 11.32 (1H, s, NH-3).

Compound II-G

δ 0.85 (3H, t, $CH_3(CH_2)_{11}NH$, J=7 Hz), 1.18~1.29 (18H, br. s, $CH_3(CH_2)_9\overline{CH_2CH_2}NH$), 2.34 (3H, br. s, NMe-5'''), 2.90 (3H, s, $\overline{NMe-8'''}$), 5.08 (1H, br. s, H-1"), 5.55 (1H, d, H-1', J=2 Hz), 5.63 (1H, d, H-5, J=8 Hz), 6.29 (1H, br. t, H-3''', J=~6 Hz), 7.68 (1H, br. d, H-6, J=~8 Hz), 11.32 (1H, s, NH-3).

Compound II-H

δ 0.86 (3H, t, $CH_3(CH_2)_{12}NH$, J=7 Hz), 1.18~1.30 (20H, br. s, $CH_3(CH_2)_{10}\overline{CH_2CH_2}NH$), 2.35 (3H, br. s, NMe-5'''), 2.90 (3H, s, NMe-8'''), 5.09 (1H, br. s, H-1''), 5.55 (1H, d, H-1', J=~1 Hz), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

Compound II-I

δ 0.86 (3H, t, $\underline{CH_3}(CH_2)_{13}NH$, J=7 Hz), 1.18~1.30 (22H, br. s, $CH_3\underline{(CH_2)_{11}}CH_2CH_2NH$), 2.35 (3H, br. s, NMe-5'''), 2.90 (3H, s, NMe-8'''), 5.09 (1H, br. s, H-1''), 5.55 (1H, s, H-1'), 5.63 (1H, d, H-5, J=~8 Hz), 6.29 (1H, br. t, H-3''', J=~6 Hz), 7.68 (1H, br. d, H-6, J=~8 Hz), 11.32 (1H, s, NH-3).

Compound II-J

δ 0.86 (3H, t, $\underline{CH_3}(CH_2)_{14}NH$, J=7 Hz), 1.18~1.30 (24H, br. s, $CH_3\underline{(CH_2)_{12}}CH_2CH_2NH$), 2.35 (3H, br. s, NMe-5'''), 2.90 (3H, s, NMe-8'''), 5.09 (1H, br. s, H-1''), 5.55 (1H, s, H-1'), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

Compound II-K

δ 0.85 (3H, t, $\underline{CH_3}(CH_2)_{15}NH$, J=7 Hz), 1.18~1.30 (26H, br. s, $CH_3\underline{(CH_2)_{13}}CH_2CH_2NH$), 2.36 (3H, br. s, NMe-5'''), 2.91 (3H, s, NMe-8'''), 5.09 (1H, br. s, H-1''), 5.55 (1H, d, H-1', J=~2 Hz), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

Compound II-L

δ 0.85 (3H, t, $\underline{CH_3}(CH_2)_{16}NH$, J=7 Hz), 1.18~1.30 (28H, br. s, $CH_3\underline{(CH_2)_{13}}CH_2CH_2NH$), 2.35 (3H, br. s, NMe-5'''), 2.90 (3H, s, NMe-8'''), 5.09 (1H, br. s, H-1''), 5.55 (1H, s, H-1'), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

Compound II-M

δ 0.86 (3H, t, $\underline{CH_3}(CH_2)_{17}NH$, J=7 Hz), 1.18~1.30 (30H, br. s, $CH_3\underline{(CH_2)_{15}}CH_2CH_2NH$), 2.35 (3H, br. s, NMe-5'''), 2.90 (3H, s, NMe-8'''), 5.09 (1H, br. s, H-1''), 5.55 (1H, s, H-1'), 5.63 (1H, d, H-5, J=~8 Hz), 6.29 (1H, br. t, H-3''', J=~6 Hz), 7.67 (1H, br. d, H-6, J=~8 Hz), 11.32 (1H, s, NH-3).

Compound II-N

δ 0.85 (3H, t, $\underline{CH_3}(CH_2)_{18}NH$, J=7 Hz), 1.18~1.30 (32H, br. s, $CH_3\underline{(CH_2)_{16}}CH_2CH_2NH$), 2.34 (3H, br. s, NMe-5'''), 2.90 (3H, s, NMe-8'''), 5.08 (1H, br. s, H-1''), 5.55 (1H, d, H-1', J=~2 Hz), 5.63 (1H, d, H-5, J=~8 Hz), 6.29 (1H, br. t, H-3''', J=~6 Hz), 7.68 (1H, br. d, H-6, J=~8 Hz), 11.32 (1H, s, NH-3).

Compound II-O

δ 0.85 (3H, t, $\underline{CH_3}(CH_2)_{19}NH$, J=7 Hz), 1.18~1.30 (34H, br. s, $CH_3\underline{(CH_2)_{17}}CH_2CH_2NH$), 2.34 (3H, br. s, NMe-5'''), 2.90 (3H, s, NMe-8'''), 5.08 (1H, br. s, H-1''), 5.55 (1H, slightly br. d, H-1', J=~1 Hz), 5.63 (1H, d, H-5, J=~8 Hz), 6.28 (1H, br. t, H-3''', J=~6 Hz), 7.67 (1H, br. d, H-6, J=~8 Hz), 11.32 (1H, s, NH-3).

Compound II-P

δ 0.86 (3H, t, $\underline{CH_3}(CH_2)_{20}NH$, J=7 Hz), 1.18~1.30 (36H, br. s, $CH_3\underline{(CH_2)_{18}}CH_2CH_2NH$), 2.34 (3H, br. s, NMe-5'''), 2.90 (3H, s, NMe-8'''), 5.08 (1H, br. s, H-1''), 5.55 (1H, slightly br. d, H-1', J=~1 Hz), 5.63 (1H, d, H-5, J=~8 Hz), 6.28 (1H, br. t, H-3''', J=~6 Hz), 7.68 (1H, br. d, H-6, J=~8 Hz), 11.31 (1H, s, NH-3).

Compound II-Q

δ 1.14~1.45 (22H, m, $—\underline{(CH_2)_{11}}—$), 2.35 (3H, br. s, NMe-5'''), 2.91 (3H, s, NMe-8'''), 5.09 (1H, br. s, H-1''), 5.58 (1H, d, H-1', J=~2 Hz), 5.64 (1H, d, H-5, J=8 Hz), 6.31 (1H, br. t, H-3''', J=6 Hz), 7.66 (1H, br. d, H-6, J=8 Hz), 11.33 (1H, s, NH-3).

Compound II-R

δ 0.85 (3H, t, $\underline{CH_3}CH_2—$, J=7 Hz), 2.35 (3H, br. s, NMe-5'''), 2.90 (3H, s, NMe-8'''), 5.09 (1H, br. s, H-1''), 5.55 (1H, d, H-1', J=~2 Hz), 5.63 (1H, d, H-5, J=~8 Hz), 6.28 (1H, br. t, H-3''', J=~6 Hz), 7.67 (1H, br. d, H-6, J=~8 Hz), 11.32 (1H, s, NH-3).

Compound II-1

δ 2.26 (3H, s, $\underline{CH_3}C_6H_4NH$), 2.38 (3H, br. s, NMe-5'''), 2.96 (3H, s, NMe-8'''), 5.11 (1H, br. s, H-1''), 5.60 (1H, d, H-1', J=2 Hz), 5.62 (1H, d, H-5, J=~8 Hz), 6.40 (1H, br. t, H-3''', J=~6 Hz), 7.13 and 7.50 (each 2H, d, $CH_3C_6H_4NH$, J=8 Hz), 7.68 (1H, d, H-6, J=~8 Hz), 10.14 (1H, s, $\overline{CH_3C_6H_4\underline{NH}}$), 11.32 (1H, s, NH-3).

Compound II-2

δ 1.16 (3H, t, $\underline{CH_3}CH_2C_6H_4NH$, J=8 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, dd, H-5, J=2, 8 Hz), 6.39 (1H, br. t, H-3''', J=~6 Hz), 7.15 and 7.52 (each 2H, d, $CH_3CH_2C_6H_4NH$, J=8 Hz), 7.69 (1H, d, H-6, J=8 Hz), 10.14 (1H, s, $\overline{CH_3CH_2C_6H_4\underline{NH}}$), 11.32 (1H, d, NH-3, J=2 Hz).

Compound II-3

δ0.87 (3H, t, $\underline{CH_3}(CH_2)_2C_6H_4NH$, J=8 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, dd, H-5, J=2, 8 Hz), 6.39 (1H, br. t, H-3''', J=~6 Hz), 7.14 and 7.52 (each 2H, d, $CH_3(CH_2)_2C_6H_4NH$, J=8 Hz), 7.69 (1H, d, H-6, J=8 Hz), 10.14 (1H, s, $\overline{CH_3(CH_2)_2C_6H_4\underline{NH}}$), 11.32 (1H, d, NH-3, J=2 Hz).

Compound II-4

δ 0.89 (3H, t, $\underline{CH_3}(CH_2)_3C_6H_4NH$, J=7.5 Hz), 2.38 (3H, br. s, NMe-5'''), 2.96 (3H, s, NMe-8'''), 5.12 (1H, br. s, H-1''), 5.60 (1H, d, H-1', J=2 Hz), 5.62 (1H, d, H-5, J=~8 Hz), 6.40 (1H, br. t, H-3''', J=~6 Hz), 7.14 and 7.52 (each 2H, d, $CH_3(CH_2)_3C_6H_4NH$, J=8 Hz), 7.68 (1H, d, H-6, J=8 Hz), 10.15 (1H, s, $\overline{CH_3(CH_2)_3C_6H_4\underline{NH}}$), 11.32 (1H, s, NH-3).

Compound II-5

δ 0.85 (3H, t, $\underline{CH_3}(CH_2)_4C_6H_4NH$, J=7 Hz), 2.38 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 7.13 and 7.51 (each 2H, d, $CH_3(CH_2)_4C_6H_4NH$, J=8 Hz), 7.68 (1H, d, H-6, J=8 Hz), 10.14 (1H, s, $\overline{CH_3(CH_2)_4C_6H_4\underline{NH}}$), 11.32 (1H, s, NH-3).

Compound II-6

δ 0.85 (3H, t, $\underline{CH_3}(CH_2)_5C_6H_4NH$, J=7 Hz), 2.38 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 7.13 and 7.51 (each 2H, d, $CH_3(CH_2)_5C_6H_4NH$, J=8 Hz), 7.68 (1H, d, H-6, J=8 Hz), 10.14 (1H, s, $\overline{CH_3(CH_2)_5C_6H_4\underline{NH}}$), 11.32 (1H, s, NH-3).

Compound II-7

δ 0.85 (3H, t, $\underline{CH_3}(CH_2)_6C_6H_4NH$, J=7 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 7.13 and 7.51 (each 2H, d, $CH_3(CH_2)_6C_6H_4NH$, J=8 Hz), 7.68 (1H, d, H-6, J=8 Hz), 10.14 (1H, s, $\overline{CH_3(CH_2)_6C_6H_4\underline{NH}}$), 11.32 (1H, s, NH-3).

Compound II-8

δ 0.85 (3H, t, $\underline{CH_3}(CH_2)_7C_6H_4NH$, J=7 Hz), 2.37 (3H, br. s, NMe-5'''), 2.95 (3H, s, NMe-8'''), 5.12 (1H, br. s, H-1''), 5.60 (1H, d, H-1', J=2 Hz), 5.62 (1H, d, H-5, J=~8 Hz), 6.39 (1H, br. t, H-3''', J=~6 Hz), 7.13 and 7.51 (each 2H, d, CH$_3$(CH$_2$)$_7$C$_6$H$_4$NH, J=8 Hz), 7.68 (1H, d, H-6, J=8 Hz), 10.14 (1H, s, CH$_3$(CH$_2$)$_7$C$_6$H$_4$NH), 11.32 (1H, s, NH-3).

Compound II-10

δ 0.85 (3H, t, CH$_3$(CH$_2$)$_9$C$_6$H$_4$NH, J=7 Hz), 2.38 (3H, br. s, NMe-5'''), 2.96 (3H, s, NMe-8'''), 5.12 (1H, br. s, H-1''), 5.60 (1H, d, H-1', J=2 Hz), 5.62 (1H, d, H-5, J=~8 Hz), 6.39 (1H, br. t, H-3''', J=~6 Hz), 7.13 and 7.51 (each 2H, d, CH$_3$(CH$_2$)$_9$C$_6$H$_4$NH, J=8 Hz), 7.68 (1H, d, H-6, J=8 Hz), 10.14 (1H, s, CH$_3$(CH$_2$)$_9$C$_6$H$_4$NH), 11.32 (1H, s, NH-3).

Compound II-12

δ 0.85 (3H, t, CH$_3$(CH$_2$)$_{11}$C$_6$H$_4$NH, J=8 Hz), 2.38 (3H, br. s, NMe-5'''), 2.95 (3H, s, NMe-8'''), 5.11 (1H, br. s, H-1''), 5.60 (1H, d, H-1', J=~2 Hz), 5.62 (1H, d, H-5, J=~8 Hz), 6.39 (1H, br. t, H-3''', J=~6 Hz), 7.13 and 7.51 (each 2H, d, CH$_3$(CH$_2$)$_{11}$C$_6$H$_4$NH, J=8 Hz), 7.68 (1H, d, H-6, J=8 Hz), 10.15 (1H, s, CH$_3$(CH$_2$)$_{11}$C$_6$H$_4$NH), 11.32 (1H, s, NH-3).

Compound II-14

δ 0.85 (3H, t, CH$_3$(CH$_2$)$_{13}$C$_6$H$_4$NH, J=7 Hz), 2.37 (3H, br. s, NMe-5'''), 2.95 (3H, s, NMe-8'''), 5.12 (1H, br. s, H-1''), 5.60 (1H, d, H-1', J=2 Hz), 5.62 (1H, dd, H-5, J=2, ~8 Hz), 6.38 (1H, br. t, H-3''', J=~6 Hz), 7.13 and 7.51 (each 2H, d, CH$_3$(CH$_2$)$_{13}$C$_6$H$_4$NH, J=8.5 Hz), 7.69 (1H, d, H-6, J=8 Hz), 10.14 (1H, s, CH$_3$(CH$_2$)$_{13}$C$_6$H$_4$NH), 11.31 (1H, d, NH-3, J=~2 Hz).

Compound II-15

δ 2.37 (3H, br. s, NMe-5'''), 2.95 (3H, s, NMe-8'''), 3.73 (3H, s, OCH$_3$), 5.11 (1H, br. s, H-1''), 5.60 (1H, d, H-1', J=2 Hz), 5.63 (1H, dd, H-5, J=~2, 8 Hz), 6.39 (1H, br. t, H-3''', J=~6 Hz), 6.89 and 7.52 (each 2H, d, CH$_3$OC$_6$H$_4$NH, J=9 Hz), 7.68 (1H, d, H-6, J=8 Hz), 10.08 (1H, s, CH$_3$OC$_6$H$_4$NH), 11.32 (1H, d, NH-3, J=2 Hz).

Compound II-16

δ 1.31 (3H, t, CH$_3$CH$_2$OC$_6$H$_4$NH, J=7 Hz), 2.38 (3H, br. s, NMe-5'''), 2.96 (3H, s, NMe-8'''), 5.11 (1H, br. s, H-1''), 5.60 (1H, d, H-1', J=2 Hz), 5.63 (1H, d, H-5, J=~8 Hz), 6.39 (1H, br. t, H-3''', J=~6 Hz), 6.87 and 7.51 (each 2H, d, CH$_3$CH$_2$OC$_6$H$_4$NH, J=9 Hz), 7.68 (1H, d, H-6, J=8 Hz), 10.08 (1H, s, CH$_3$CH$_2$OC$_6$H$_4$NH), 11.33 (1H, s, NH-3).

Compound II-18

δ 0.93 (3H, t, CH$_3$(CH$_2$)$_3$OC$_6$H$_4$NH, J=7.5 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 6.88 and 7.51 (each 2H, d, CH$_3$(CH$_2$)$_3$OC$_6$H$_4$NH, J=9 Hz), 7.68 (1H, d, H-6, J=8 Hz), 10.07 (1H, s, CH$_3$(CH$_2$)$_3$OC$_6$H$_4$NH), 11.33 (1H, s, NH-3).

Compound II-19

δ 0.89 (3H, t, CH$_3$(CH$_2$)$_4$OC$_6$H$_4$NH, J=7 Hz), 2.37 (3H, br. s, NMe-5'''), 2.96 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=6 Hz), 6.88 and 7.50 (each 2H, d, CH$_3$(CH$_2$)$_4$OC$_6$H$_4$NH, J=9 Hz), 7.68 (1H, d, H-6, J=8 Hz), 10.07 (1H, s, CH$_3$(CH$_2$)$_4$OC$_6$H$_4$NH), 11.33 (1H, s, NH-3).

Compound II-20

δ 0.88 (3H, t, CH$_3$(CH$_2$)$_5$OC$_6$H$_4$NH, J=7 Hz), 2.38 (3H, br. s, NMe-5'''), 2.96 (3H, s, NMe-8'''), 5.12 (1H, br. s, H-1''), 5.60 (1H, d, H-1', J=2 Hz), 5.62 (1H, d, H-5, J=~8 Hz), 6.39 (1H, br. t, H-3''', J=6 Hz), 6.88 and 7.50 (each 2H, d, CH$_3$(CH$_2$)$_5$OC$_6$H$_4$NH, J=9 Hz), 7.67 (1H, d, H-6, J=8 Hz), 10.08 (1H, s, CH$_3$(CH$_2$)$_5$OC$_6$H$_4$NH), 11.33 (1H, s, NH-3).

Compound II-21

δ 0.87 (3H, t, CH$_3$(CH$_2$)$_6$OC$_6$H$_4$NH, J=7 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.39 (1H, br. t, H-3''', J=~6 Hz), 6.88 and 7.50 (each 2H, d, CH$_3$(CH$_2$)$_6$OC$_6$H$_4$NH, J=9 Hz), 7.68 (1H, d, H-6, J=8 Hz), 10.07 (1H, s, CH$_3$(CH$_2$)$_6$OC$_6$H$_4$NH), 11.32 (1H, s, NH-3).

Compound II-23

δ 0.86 (3H, t, CH$_3$(CH$_2$)$_8$OC$_6$H$_4$NH, J=7 Hz), 2.37 (3H, br. s, NMe-5'''), 2.95 (3H, s, NMe-8'''), 5.11 (1H, br. s, H-1''), 5.60 (1H, d, H-1', J=2 Hz), 5.62 (1H, d, H-5, J=~8 Hz), 6.38 (1H, br. t, H-3''', J=~6 Hz), 6.88 and 7.50 (each 2H, d, CH$_3$(CH$_2$)$_8$OC$_6$H$_4$NH, J=9 Hz), 7.68 (1H, d, H-6, J=8 Hz), 10.07 (1H, s, CH$_3$(CH$_2$)$_8$OC$_6$H$_4$NH), 11.32 (1H, d, NH-3, J=~2 Hz).

Compound II-24

δ 2.37 (3H, br. s, NMe-5'''), 2.95 (3H, s, NMe-8'''), 5.11 (1H, br. s, H-1''), 5.59 (1H, d, H-1', J=2 Hz), 5.62 (1H, d, H-5, J=~8 Hz), 6.38 (1H, br. t, H-3''', J=~6 Hz), 7.16 and 7.52 (each 2H, d, —C$_6$H$_4$NH, J=9 Hz), 7.68 (1H, d, H-6, J=8 Hz), 10.14 (1H, s, —C$_6$H$_4$NH), 11.32 (1H, s, NH-3).

Now, an illustrative experiment of the preparation of a caprazene-1'''-ester derivative of the formula (III) according to the fourth aspect of this invention is concretely described with reference to the following Example 4.

Example 4

(a) Preparation of 5''-N-Boc-caprazene-1'''-ester Derivative from 5''-N-Boc-caprazene

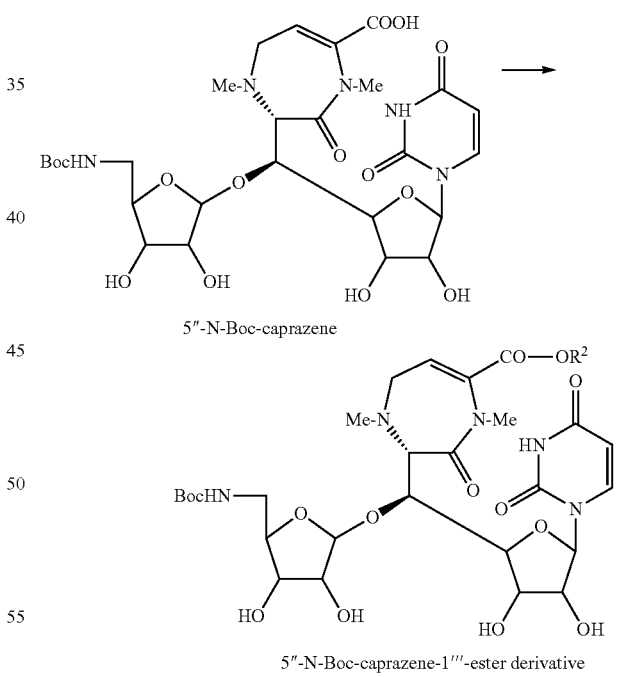

5''-N-Boc-caprazene

5''-N-Boc-caprazene-1'''-ester derivative

The 5''-N-Boc-caprazene obtained in Example 3(a) (150 mg) was dissolved in pyridine (5 ml). To the resultant solution were added N,N-bis(2-oxo-3-oxazolidinyl) phosphinic chloride (120 mg) as well as each one of a variety of alcohol compounds R$^2$—OH shown in Table 17 below (2 molar equivalents in each case). The resulting reaction mixture was stirred at room temperature overnight to cause the reaction intended (for the esterification reaction).

TABLE 17

| Alcohol compound R²—OH | |
|---|---|
| Chemical formula | Name |
| H₃C(CH₂)₉—OH | Decyl alcohol |
| H₃C(CH₂)₁₂—OH | Tridecyl alcohol |
| H₃C(CH₂)₁₇—OH | Octadecyl alcohol |
| H₃C—CH₂—CH=CH—(CH₂)₁₀—OH | Cis-11-tetradecene-1-ol |
| H₃C—(CH₂)₈—CH=CH—CH₂—OH | Trans-2-dodecenol |
| H₂C=CH—(CH₂)₉—OH | 10-Undecene-1-ol |
| H₃C—(CH₂)₅—C≡C—(CH₂)₂—OH | 3-Decyne-1-ol |

The resulting esterification reaction solution was concentrated and the resulting syrupy concentrate was extracted with chloroform. The chloroform extract was washed with water and then concentrated. The resulting residue was purified by a silica-gel column chromatography (developing solvent system: chloroform-methanol=10:1). Thus, there was yielded each of 5″-N-Boc-protected derivatives of caprazene-1′″-ester derivatives having Compound code name shown in Table 5 given hereinbefore, as a colorless solid. Yield; 96-108 mg (Yield at the end of the two steps from caprazene; 45-52%).

(b) Synthesis of caprazene-1′″-ester Derivative

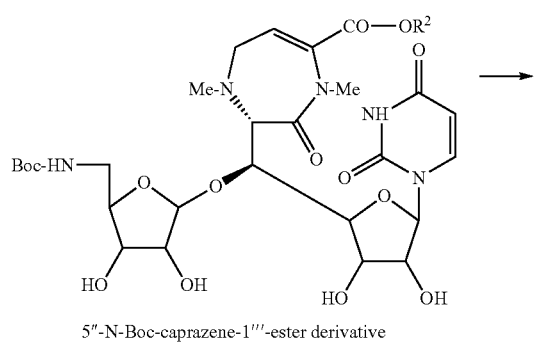

5″-N-Boc-caprazene-1′″-ester derivative

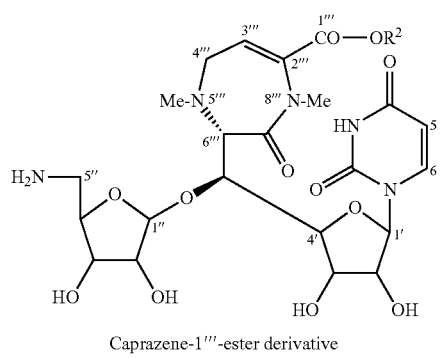

Caprazene-1′″-ester derivative

Each of the 5″-N-Boc-caprazene-1′″-ester derivatives obtained in Example 4 (a) (50 mg) was dissolved in methanolic solution of 80% trifluoroacetic acid (1 ml). The resultant solution was kept at room temperature for 1 hour to cause the reaction for the elimination of the amino-protecting group (Boc). The resulting reaction solution was concentrated, and to the resulting syrupy concentrate was added an amount of diethyl ether to deposit a precipitate which was then washed with diethyl ether and dried. Thus, there was yielded each of Compound III-AA to Compound III-GG shown as code name in Table 5 given hereinbefore, a as colorless solid. Yield; 55.9-57.4 mg (Yield as addition salt of bis-trifluoroacetic acid; 98-99%).

¹H-NMR spectrum (500 MHz, in deutero-dimethylsulfoxide, TMS internal standard) of each of the Compound III-AA to Compound III-GG (see Table 5) obtained as the caprazene-1′″-ester derivatives of the formula (III) in Example 4(c) is shown below.

Compound III-AA

δ 0.86 (3H, t, $CH_3(CH_2)_9O$, J=7 Hz), 1.18~1.35 (14H, slightly br. s, $CH_3\overline{(CH_2)_7}CH_2CH_2O$), 2.35 (3H, br. s, NMe-5′″), 2.96 (3H, s, $\overline{NMe-8′″}$), 5.09 (1H, s, H-1″), 5.53 (1H, d, H-1′, J=2.5 Hz), 5.64 (1H, dd, H-5, J=~1.5, 8 Hz), 6.73 (1H, t, H-3′″, J=7 Hz), 7.63 (1H, br. d, H-6, J=8 Hz), 11.33 (1H, d, NH-3, J=~1.5 Hz).

Compound III-BB

δ 0.86 (3H, t, $CH_3(CH_2)_{12}O$, J=7 Hz), 1.2~1.3 (20H, slightly br. s, $CH_3\overline{(CH_2)_{10}}CH_2CH_2O$), 2.36 (3H, br. s, NMe-5′″), 2.96 (3H, s, $\overline{NMe-8′″}$), 5.09 (1H, s, H-1″), 5.53 (1H, d, H-1′, J=2 Hz), 5.64 (1H, d, H-5, J=8 Hz), 6.73 (1H, t, H-3′″, J=7 Hz), 7.63 (1H, d, H-6, J=8 Hz), 11.33 (1H, s, NH-3).

Compound III-CC

δ 0.86 (3H, t, $CH_3(CH_2)_{17}O$, J=7 Hz), 1.2~1.3 (30H, slightly br. s, $CH_3\overline{(CH_2)_{15}}CH_2CH_2O$), 2.37 (3H, br. s, NMe-5′″), 2.97 (3H, s, $\overline{NMe-8′″}$), 5.10 (1H, slightly br. s, H-1″), 5.53 (1H, d, H-1′, J=2.5 Hz), 5.64 (1H, slightly br. d, H-5, J=8 Hz), 6.74 (1H, t, H-3′″, J=7 Hz), 7.62 (1H, d, H-6, J=8 Hz), 11.33 (1H, slightly br. s, NH-3).

Compound III-DD

δ 0.91 (3H, t, $CH_3CH_2CH=CH—$, J=7.5 Hz), 2.36 (3H, br. s, NMe-5′″), $\overline{2.96}$ (3H, s, NMe-8′″), 5.09 (1H, s, H-1″), 5.53 (1H, d, H-1′, J=2 Hz), 5.64 (1H, d, H-5, J=8 Hz), 6.73 (1H, t, H-3′″, J=7 Hz), 7.63 (1H, d, H-6, J=8 Hz), 11.33 (1H, s, NH-3).

Compound III-EE

δ 0.86 (3H, t, $CH_3CH_2—$, J=7 Hz), 2.36 (3H, slightly br. s, NMe-5′″), $\overline{2.96}$ (3H, s, NMe-8′″), 4.60 (2H, m, $—CH_2CH=CHCH_2O—$), 5.09 (1H, s, H-1″), 5.53 (1H, s, H-1′), 5.55 (1H, $\overline{m}$, $—CH_2CH=CHCH_2O—$), 5.65 (1H, d, H-5, J=8 Hz), 5.80 (1H, dt, $—CH_2\overline{CH}=CHCH_2O—$, J=~0.7, ~7, ~15 Hz), 6.75 (1H, t, H-3′″, J=$\overline{7 Hz}$), 7.64 (1H, d, H-6, J=8 Hz), 11.34 (1H, s, NH-3).

Compound III-FF

δ 2.36 (3H, br. s, NMe-5′″), 2.96 (3H, s, NMe-8′″), 5.09 (1H, br. s, H-1″), 5.53 (1H, slightly br. s, H-1′), 5.65 (1H, d, H-5, J=8 Hz), 5.75 (1H, m, $CH_2=CH—$), 6.73 (1H, t, H-3′″, J=7 Hz), 7.63 (1H, d, H-6, J=8 $\overline{Hz)}$, 11.34 (1H, s, NH-3).

Compound III-GG

δ 0.85 (3H, t, $CH_3CH_2—$, J=7 Hz), 2.35 (3H, slightly br. s, NMe-5′″), 2.99 $\overline{(3H}$, s, NMe-8′″), 5.10 (1H, s, H-1″), 5.55 (1H, d, H-1′, J=~2 Hz), 5.65 (1H, dd, H-5, J=~1.5, 8 Hz), 6.76 (1H, t, H-3′″, J=7 Hz), 7.65 (1H, d, H-6, J=8 Hz), 11.34 (1H, slightly br. s, NH-3).

Further, an illustrative experiment of the preparation of caprazol of the formula (IV) according to the fifth aspect of this invention by the process according to the sixth aspect of this invention is concretely explained with reference to the following Examples 5-6.

Example 5

Synthesis of Caprazol from Caprazamycin B

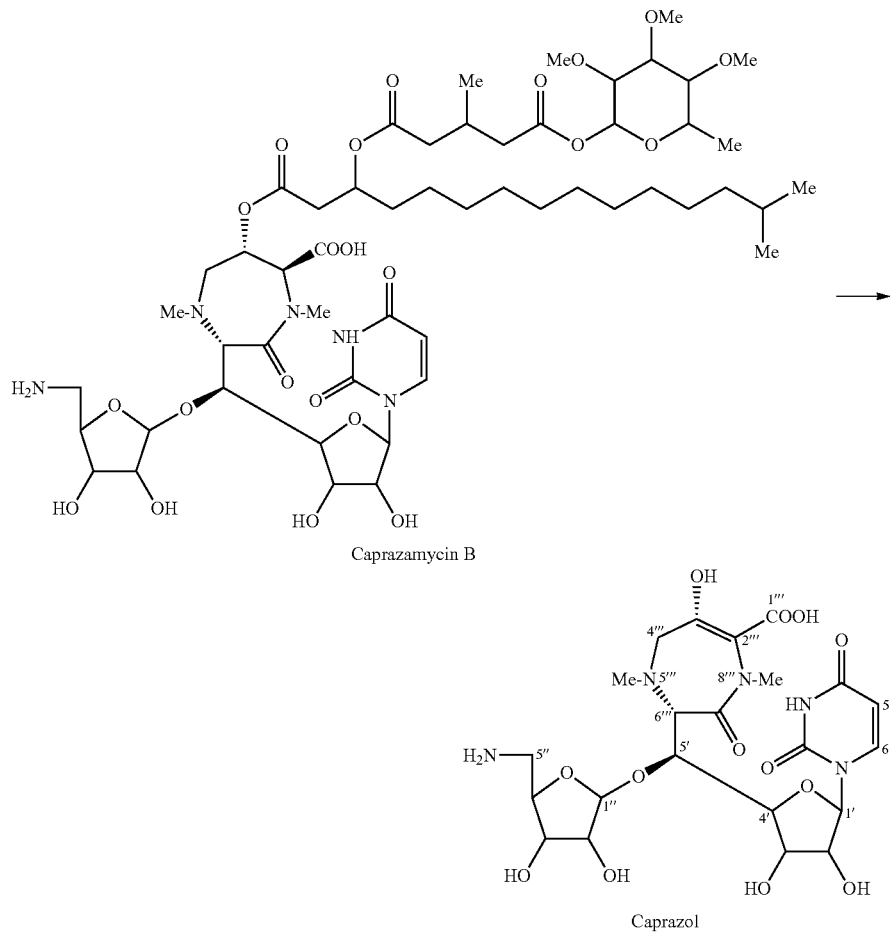

Caprazamycin B (150 mg) was dissolved in N,N-dimethylformamide (1.5 ml), and to the resultant solution was then added 28% aqueous ammonia solution (1.5 ml). The resulting mixture was stirred at room temperature for 4 days to effect the intended hydrolysis. Insolubles formed in the reaction solution were filtered off, and thereafter the reaction solution was concentrated and the resulting residue was washed with acetone and dried. Thus, there was afforded caprazol (74.7 mg) as a colorless solid.

Yield; 99%.

Melting point: 205-206° C. (with decomposition) (after the crystallization from water-methanol)

$^1$H-NMR spectrum and $^{13}$C-NMR spectrum of caprazol are shown in the following Table 18.

TABLE 18

| Position | $^1$H-NMR data of caprazol ($\delta$, ppm in D$_2$O) | Position | $^{13}$C-NMR data of caprazol ($\delta$, ppm in D$_2$O) |
|---|---|---|---|
| 5 | 5.82, d, J = 8 Hz | 2 | 151.8 |
| 6 | 7.77, d, J = 8 Hz | 4 | 167.1 |
|  |  | 5 | 101.7 |
|  |  | 6 | 142.9 |

TABLE 18-continued

| Position | $^1$H-NMR data of caprazol ($\delta$, ppm in D$_2$O) | Position | $^{13}$C-NMR data of caprazol ($\delta$, ppm in D$_2$O) |
|---|---|---|---|
| 1' | 5.60, slightly br. s |  |  |
| 2' | 4.31, br. d, J = 5 Hz | 1' | 91.8 |
| 3' | 4.08, dd, J = 5, 8 Hz | 2' | 74.0 |
| 4' | 4.13, d, J = 8 Hz | 3' | 69.3 |
| 5' | 4.39, d, J = 9 Hz | 4' | 82.4 |
|  |  | 5' | 77.6 |
| 1" | 5.17, slightly br. s |  |  |
| 2" | 4.14, d, J = 3 Hz |  |  |
| 3" | 4.25, m | 1" | 111.2 |
| 4" | ~4.21, m | 2" | 75.4 |
| 5"a | 3.20, dd, J = 4, 13.5 Hz | 3" | 70.6 |
| 5"b | 3.32, dd, J = 3.5, 13.5 Hz | 4" | 79.0 |
|  |  | 5" | 40.2 |
| 2''' | 4.20, d, J = 5 Hz |  |  |
| 3''' | 4.44, br. s | 1''' | 174.1 |
| 4'''a | 3.01, br. d, J = 15 Hz | 2''' | 70.0 |
| 4'''b | 3.13, br. d, J = 15 Hz | 3''' | 69.3 |
| 6''' | 3.85, d, J = 9 Hz | 4''' | 59.1 |
| MeN-5''' | 2.43, s | 6''' | 63.5 |
| MeN-8''' | 3.07, s | 7''' | 172.7 |
|  |  | MeN-5''' | 37.0 |
|  |  | MeN-8''' | 39.2 |

Example 6

Synthesis of Caprazol from a Mixture of Caprazamycins C—F

A mixture of caprazamycins C, D, E and F (2.1 g) was dissolved in N,N-dimethylformamide (20 ml). To the resulting solution was added 28% aqueous ammonia solution (20 ml), and then the intended hydrolysis reaction was effected at room temperature for 110 hours. Insolubles formed in the reaction solution was filtered off. Thereafter, the reaction solution was concentrated and the resulting residue was washed with acetone and then dried. Thus, there was yielded caprazol (1.08 g).

Example 7

Preparation of Caprazene from Caprazol

An amount of caprazol was dissolved in an amount of 1N aqueous hydrochloric acid and the resultant solution was heated at 100° C. for 3 hours, thereby to produce caprazene in the yield of 20%. About 20% of caprazol was left unreacted. Respective chemical structure of each compound was confirmed by NMR analysis. The resulting reaction solution was concentrated under a reduced pressure and the resulting residue was subjected to a silica-gel column chromatography. Thus, there can be separated caprazene and caprazol, from each other.

Further, an illustrative experiment of the preparation of a caprazol-1'''-amide derivative of the formula (V) according to the seventh aspect of this invention is concretely described with reference to Example 8 given below.

Example 8

(a) Synthesis of 5''-N-Boc-caprazol

Caprazol of the formula (IV) (2.80 g) was dissolved in a mixed solvent of water-dioxane (1:2), and to the resultant solution were added triethylamine (1.7 ml) and a dioxane solution (5 ml) of di-t-butyl dicarbonate (1.27 g). The intended reaction for the resulting mixture was effected at room temperature for 1 hour. The resulting reaction solution was concentrated and the residue obtained was washed with ethyl acetate and then dried. Thus, there was afforded 5''-N-Boc-caprazol (3.19 g) as a pale yellow solid. Crude yield; 97%.

$^1$H-NMR spectrum (500 MHz, in $D_2O$): δ 1.40 (9H, s, methyl in the t-butoxycarbonyl group), 2.47 (3H, s, NMe-5'''), 3.13 (3H, s, NMe-8'''), 5.16 (1H, s, H-1''), 5.74 (1H, br. s, H-1').

(b) Synthesis of 1'''-dodecylamide Derivative of 5''-N-Boc-caprazol

The 5''-N-Boc-caprazol (97.8 mg) obtained in Example 8(a) was dissolved in N,N-dimethylformamide (3 ml), and to the resultant solution were added triethylamine (0.21 ml), n-dodecylamine (137 mg) and N,N-bis(2-oxo-3-oxazolidinyl) phosphinic chloride (188 mg). The resulting mixture was heated at 40° C. to effect the reaction intended (for the amidation reaction). At the end of 2 hours and 4 hours after the start of the reaction, respectively, there were added triethylamine (0.21 ml), n-dodecylamine (137 mg) and N,N-bis(2-oxo-3-oxazolidinyl) phosphinic chloride (189 mg) to the reaction mixture.

At the six hours after the start of the reaction, the reaction solution was concentrated to dryness. The residue was extracted with chloroform, and the chloroform extract was washed once with water, then twice with aqueous saturated sodium sulfate solution and then dried over anhydrous sodium sulfate. The resulting solution was concentrated to dryness to yield a solid. The solid was purified by a silica-gel column chromatography (developing system: chloroform-methanol-concentrated aqueous ammonia; 4:1:0.1). Thus there was afforded 5''-N-Boc-caprazol-1'''-dodecylamide derivative (45.4 mg) (Yield from caprazol; 32%).

(c) Synthesis of caprazol-1'''-dodecylamide Derivative

The 5''-N-Boc-caprazol-1'''-dodecylamide derivative above was dissolved in a mixture of trifluoroacetic acid-methanol (8:2) (0.45 ml), and the reaction intended was effected at room temperature for 2 hours (for the elimination of Boc). The reaction solution so obtained was concentrated to dryness, and to the resulting residue was added diethyl ether and the insoluble matters were washed with diethyl ether. Thus, there was afforded caprazol-1'''-dodecyl-amide derivative (corresponding to Compound V-G in Table 7) in the form of an addition salt of bis-trifluoroacetic acid (46 mg) (Yield; 33%).

$[α]_D^{19}$ +12° (c 1, methanol)

$^1$H-NMR spectrum (500 MHz, in deutero-methanol):

δ 0.89 (3H, t, N(CH$_2$)$_{11}$Me, J=7 Hz), 2.51 (3H, s, NMe-5'''), 3.18 (3H, s, NMe-8'''), 5.17 (1H, s, H-1''), 5.76 (1H, s, H-1'), 5.77 (1H, d, H-5, J$_{5,6}$=8 Hz), 8.08 (1H, d, H-6).

Now, an illustrative experiment of the preparation of a caprazol-1'''-amide-1'''-ester derivative of the formula (VI) according to the eighth aspect of this invention is explained with reference to Example 9

Example 9

(a) Synthesis of 5''-N-Boc-2',3'; 2'',3''-di-O-isopropylidene-caprazol (the Compound of the Formula (XIV) Above)

The 5''-N-Boc-caprazol obtained in Example 8(a) (1.097 g) was dissolved in N,N-dimethylformamide (33 ml), and the resultant solution were added (±)10-camphor-sulfonic acid (1.06 g) and dimethoxymethane (6 ml) and the reaction intend was effected at room temperature. One day later, there were further added (±)10-camphor-sulfonic acid (151 mg) and dimethoxymethane (2 ml). Two days later, there were added (±)10-camphor-sulfonic acid (113 mg) (as acid catalyst) and dimethoxymethane (2 ml). Three days later, there was added dimethoxymethane (2 ml) to the resulting mixture (for the reaction of introducing O-isopropylidene groups).

The 5''-N-Boc-caprazol (3.19 g) obtained in Example 8(a) was dissolved in N,N-dimethylformamide (60 ml), and to the resultant solution were added (±)camphor-10-sulfonic acid (3.29 g) and 2,2-dimethoxypropane (17 ml). The reaction intended was effected at room temperature overnight (for the reaction of introducing O-isopropylidene groups).

The reaction solution so obtained was neutralized with the addition of concentrated aqueous ammonia (0.5 ml) and the neutralized solution was concentrated. The resulting residue was dissolved in n-butanol, and the organic layer was washed with water, then concentrated under a reduced pressure and dried, affording the compound of the formula (XIV) above (3.55 g).

Yield; 99%.

$[\alpha]_D^{19}$ −30° (c 2, chloroform)

$^1$H-NMR spectrum (500 MHz, in deutero-methanol):

δ 1.25, 1.36, 1.40, 1.53 (each 3H, s, methyl in isopropylidene group), 1.45 (9H, s, methyl in t-butoxycarbonyl group), 2.50 (3H, s, NMe-5'''), 3.09 (3H, s, NMe-8'''), 5.24 (1H, s, H-1''), 5.83 (1H, d, H-1', $J_{1',2'}$=2.7 Hz).

(b) Preparation of 5''-N-Boc-2',3'; 2'',3''-di-O— isopropylidene-caprazol-1'''-dodecylamide Derivative (a Compound Included within the Derivative of the Formula (XV) Above)

The 5''-N-Boc-2',3'; 2'',3''-di-O-isopropylidene-caprazol (69.6 mg) obtained in Example 9(a) was dissolved in N,N-dimethylformamide (1.78 ml), and to the resultant solution were added triethylamine (0.052 ml), n-dodecylamine (34.2 mg) and N,N-bis(2-oxo-3-oxazolidinyl)phosphinic chloride (47 mg). Then, reaction intended was effected at room temperature (for the 1'''-amidation reaction). At the end of two hours after and four hours after the start of the reaction, respectively, there were further added triethylamine (0.052 ml), n-dodecylamine (34.2 mg) and N,N-bis(2-oxo-3-oxazolidinyl)phosphinic chloride (47 mg).

After the reaction was effected for 8 hours, the reaction solution obtained was concentrated to dryness and the residue was extracted with chloroform. The chloroform extract was washed with water, dried over anhydrous sodium sulfate and concentrated to dryness. The resulting residue was purified by a silica-gel column chromatography (developing system: chloroform-methanol, 50:1). Thus, there was afforded 5''-N-Boc-2',3'; 2'',3''-di-O-isopropylidene-caprazol-1'''-dodecylamide derivative (45.8 mg) (Yield; 54%).

$[\alpha]_D^{19}$ −31° (c 2, methanol)

$^1$H-NMR spectrum (500 MHz, in deutero-methanol):

δ 0.89 (3H, t, N(CH$_2$)$_{11}$Me, J=7 Hz), 1.44 (9H, s, methyl in t-butoxycarbonyl group), 2.50 (3H, s, NMe-5'''), 3.16 (3H, s, NMe-8'''), 5.27 (1H, s, H-1''), 5.73 (1H, d, H-5, $J_{5,6}$=8 Hz), 5.94 (1H, d, H-1', $J_{1',2'}$=2.7 Hz), 7.72 (1H, d, H-6).

(c) Synthesis of 5''-N-Boc-2',3'; 2'',3''-di-O-isopropylidene-caprazol-1'''-dodecylamide-3'''-dodecanoyl-ester Derivative (a Compound Included within the Derivative of the Formula (XVII) Above)

The 5''-N-Boc-2',3'; 2'',3''-di-O-isopropylidene-caprazol-1'''-dodecylamide derivative (45.5 mg) obtained in Example 9(b) was dissolved in dichloromethane. To the resulting solution, under ice-cooling, were added 4-dimethylaminopyridine (24.5 mg) and dodecanoyl chloride (0.035 ml) (trivial name: lauroyl chloride, Cl—CO—(CH$_2$)$_{10}$—CH$_3$) as acylating reagent. And the resulting mixture was subjected to the reaction intended under ice-cooling for 3 hours (for the 3'''-O-esterification). Methanol (0.027 ml) was added to the resulting reaction solution, and then the resulting solution was diluted with chloroform. The resulting mixed solution was washed with aqueous 10% potassium hydrogen sulfate solution and then with water, dried over anhydrous sodium sulfate and then concentrated to dryness. The residue so obtained was purified by a silica-gel column chromatography (developing solvent system: chloroform-methanol, 150:0→150:1), thus affording the titled compound (39.2 mg; yield; 72%).

(d) Synthesis of caprazol-1'''-dodecylamide-3'''-dodecanoyl-ester Derivative (Compound Corresponding to Compound VI-G in Table 9 Included within the Eighth Aspect of this Invention)

The compound as obtained in the above step (c) was dissolved in a mixture of trifluoroacetic acid-methanol (8:2) (0.35 ml), and the resulting solution was subjected to the reaction intended at room temperature for 4 hours (for the deprotecting reaction). The reaction solution obtained was concentrated to dryness, and to the resultant residue was added diethyl ether. The resulting insolubles were washed with diethyl ether. Thus, there was afforded the titled compound, i.e. caprazol-1'''-dodecylamide-3'''-dodecanoylester derivative (Compound VI-G) in the form of an addition salt of bis-trifluoroacetic acid (35.8 mg; yield from the compound of the step (c) above; 63%).

$[\alpha]_D^{21}$ +6° (c, 0.5 methanol)

$^1$H-NMR spectrum (500 MHz, in deutero-methanol):

δ 0.90 (6H, t, N(CH$_2$)$_{11}$Me and (CH$_2$)$_{10}$Me, J=7 Hz), 2.37 (2H, t, CH$_2$(CH$_2$)$_9$Me, J=7 Hz), 2.45 (3H, s, NMe-5'''), 3.16 (3H, s, NMe-8'''), 5.18 (1H, s, H-1''), δ 53 (1H, br. s, H-3'''), 7.73 (1H, d, H-6, $J_{5,6}$=8 Hz).

Further, an illustrative experiment of the preparation of caprazol-3'''-ester derivative of the formula (VII) according to the ninth aspect of this invention is explained with reference to the following Example 10.

Example 10

(a) Synthesis of 5''-N-Boc-2',3'; 2'',3''-di-O-isopropylidene-caprazol-3'''-dodecanoyl-ester Derivative (a Compound Included within the Derivatives of the Formula (XVIII) Above)

5''-N-Boc-2',3'; 2'' 3''-di-O-isopropylidene-caprazol, i.e. the compound of the formula (XIV) above, as obtained in Example 9(a) (42 mg) was dissolved in dichloromethane (0.84 ml). To the resultant solution, under ice-cooling, were added 4-dimethylaminopyridine (13.6 mg) and dodecanoyl chloride (0.019 ml) [Cl—CO—(CH$_2$)$_{10}$—CH$_3$; one of acid chlorides of the formula (XVI)]. The resulting mixture was subjected to the reaction intended under ice-cooling (for the 3'''-O-esterification). After the end of 7 hours of the reaction, there were further added 4-dimethylaminopyridine (13.6 mg) and dodecanoyl chloride (0.019 ml). After the 24 hours of the reaction, there were added 4-dimethylaminopyridine (11.2 mg) and dodecanoyl chloride (0.019 ml), and after the 36 hours of the reaction, there were further added 4-dimethylaminopyridine (11.9 mg) and dodecanoyl chloride (0.019 ml) and the reaction was proceeded further.

After the 48 hours of the reaction, the resulting esterifying reaction solution, after the addition of methanol (0.017 ml) thereto, was diluted with chloroform. The resulting mixture was washed with 10% aqueous potassium hydrogen sulfate solution and then with water and then dried over anhydrous sodium sulfate. The resulting dried solution was concentrated to dryness, to afford a solid containing the titled compound (82.7 mg).

(b) Synthesis of caprazol-3'''-dodecanoyl Ester Derivative of the Following Formula (VII-1) (which is the Compound Included within the Derivatives of the Formula (XIX) or the Formula (VII) Above and which Corresponds to Compound VII-T in Table 11)

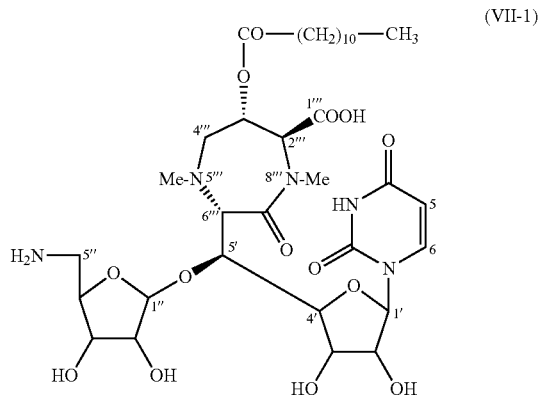

(VII-1)

The solid containing the N,O-protected caprazol-3'''-dodecanoyl-ester derivative as obtained in the step (a) above (82.7 mg) was dissolved in a mixture of trifluoroacetic acid-methanol (8:2)(0.85 ml). The resultant solution was subjected to the reaction intended at room temperature for 2.5 hours (for the deprotecting reaction). The resulting reaction solution was concentrated to dryness, and to the resultant residue was added diethyl ether. The resulting insolubles were washed with diethyl ether to give a solid (28.8 mg). The resulting solid was suspended in water and the suspension was passed through a column packed with Diaion (Registered Trade Mark) HP-20. After the column was washed with water, the column was eluted with 50% aqueous methanol, 80% aqueous methanol, and methanol, in order. The eluate fractions containing the desired substance were concentrated to dryness, thus affording the titled compound (10.4 mg) (yield from the compound obtained in the step (a) above; 25%).

$[\alpha]_D^{20}$ +17° (c 0.5, D dimethylsulfoxide)

$^1$H-NMR spectrum (500 MHz, in deutero-dimethylsulfoxide):

δ 0.86 (3H, t, $(CH_2)_{10}$Me, J=7 Hz), 2.26 (3H, s, NMe-5'''), 2.93 (3H, s, NMe-8'''), 5.00 (1H, s, H-1''), 5.40 (1H, br. s, H-3'''), 5.56 (1H, s, H-1'), 5.64 (1H, d, H-5, $J_{5,6}$=8 Hz), 7.81 (1H, d, H-6)

Furthermore, an illustrative experiment of the preparation of a caprazol-1'''-ester-3'''-ester derivative of the formula (VII) according to the ninth aspect of this invention is explained with reference to the following Example 11.

Example 11

(a) Synthesis of 5''-N-Boc-2',3'; 2'',3''-di-O-isopropylidene-caprazol-1'''-methyl-ester Derivative (the Compound Corresponding to the Derivative of the Formula (XXI) where $R^7$ is Methyl Group)

The 5''-N-Boc-2',3'; 2'',3''-di-O-isipropylidene-caprazol [the compound of the formula (XIV)] (60.7 mg) as obtained in Example 9(a) was dissolved in N,N-dimethylformamide (1.8 ml). To the solution obtained were added triethylamine (0.034 ml) and as the esterifying reagent, methanol (0.0065 ml) and N,N-bis(2-oxo-3-oxazolidinyl)phosphinic chloride (31.5 mg), and the resulting mixture was subjected to the reaction intended at room temperature for 2 hours (for the methyl-esterification reaction).

The resulting reaction solution was concentrated to dryness and the residue was extracted with chloroform. The chloroform extract was washed with water, dried over anhydrous sodium sulfate and concentrated to dryness. The residue obtained was purified by a silica-gel column chromatography (developing solvent system: chloroform-methanol; 50:1). Thus, there was afforded the titled compound represented by the following formula (XXI-1).

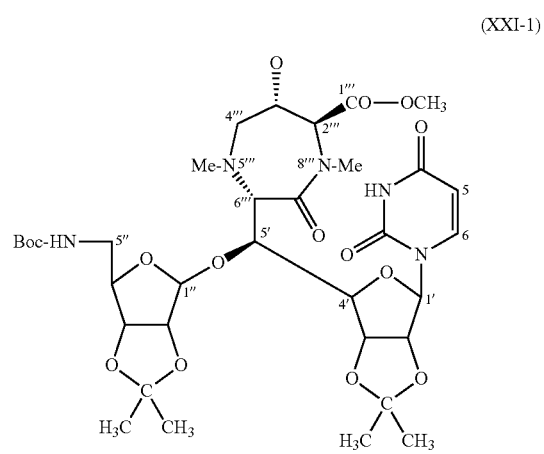

(XXI-1)

The yield was 30.9 mg (% yield; 50%).

$[\alpha]_D^{19}$ −33° (c 0.3, methanol)

$^1$H-NMR spectrum (500 MHz, in deutero-methanol):

δ 1.27, 1.37, 1.42, 1.56 (each 3H, s, methyl in the isopropylidene group), 1.43 (9H, s, methyl in the t-butoxycarbonyl group), 2.50 (3H, s, NMe-5'''), 3.15 (3H, s, NMe-8'''), 3.36 (3H, s, COOMe), 5.27 (1H, s, H-1''), 5.71 (1H, d, H-5, $J_{5,6}$=8 Hz), 5.86 (1H, s, H-1'), 7.68 (1H, d, H-6).

(b) Synthesis of 5''-N-Boc-2',3'; 2'',3''-di-O-isopropylidene-caprazol-1'''-methyl-ester-3'''-dodecanoyl-ester Derivative (the Compound Included within the Derivative of the Formula (XXII) Above)

The compound of the formula (XXI-1) (30.7 mg) as obtained in the step (a) above was dissolved in dichloromethane (0.56 ml), and to the resultant solution, under ice-cooling, were added 4-dimethylaminopyridine (10.1 mg) and as the acylating reagent, dodecanoyl chloride (0.014 ml). The mixture so obtained was subjected to the reaction intended under ice-cooling. After the reaction of 5 hours, there were further added 4-dimethylaminopyridine (6.5 mg) and dodecanoyl chloride (0.0094 ml), and the acylation reaction was proceeded further.

After the reaction of 7 hours, methanol (0.02 ml) was added to the reaction solution, and then the resulting solution was diluted with chloroform. The so diluted solution was washed with 10% aqueous potassium hydrogen sulfate solution and then with water, and dried over anhydrous sodium sulfate and then concentrated to dryness. The residue obtained was purified by a silica-gel column chromatography (developing solvent system: chloroform-methanol, 100:0, 100:1). Thus, there was afforded the titled compound (26.5 mg; yield: 70%).

(c) Synthesis of caprazol-1'''-methyl-ester-3'''-dodecanoyl-ester Derivative (Corresponding to Compound VII-G in Table 11) of the Following Formula (VII-2)

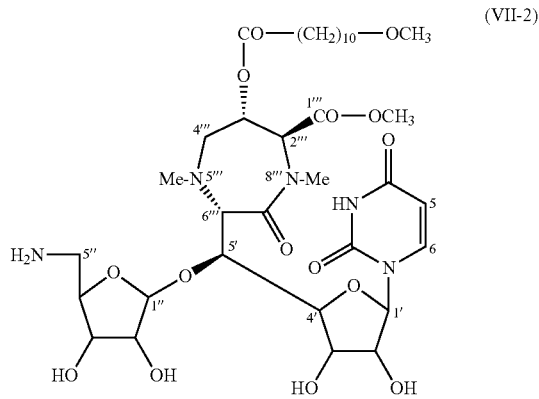

The compound obtained in the step (b) above (26.5 mg) was dissolved in a mixture of trifluoroacetic acid-methanol (8:2) (0.25 ml), and the resulting solution was subjected to the reaction intended at room temperature for 4 hours (for the deprotection reaction). The resulting reaction solution was concentrated to dryness, and to the resultant residue was added diethyl ether, and the insolubles formed were washed with diethyl ether. Thus, there was yielded the titled compound in the form of an addition salt of bis-trifluoroacetic acid (23.8 mg; yield from the compound of the formula (XXI-1) of the step (a) above; 60%).

$[\alpha]_D^{20}$ +6° (c 1, methanol)

$^1$H-NMR spectrum (500 MHz, in deutero-methanol):

δ 0.90 (6H, t, N(CH$_2$)$_{11}$Me and (CH$_2$)$_{10}$Me, J=7 Hz), 2.38 (2H, t, CH$_2$(CH$_2$)$_9$Me, J=7 Hz), 2.46 (3H, s, NMe-5'''), 3.13 (3H, s, NMe-8'''), 3.68 (3H, s, COOMe), 5.20 (1H, s, H-1''), 5.42 (1H, br. s, H-3'''), 5.71 (1H, d, H-1', J$_{1',2'}$=2 Hz), 5.75 (1H, d, H-5, J$_{5,6}$=8 Hz), 7.71 (1H, d, H-6).

Further, there are given in the following $^1$H-NMR spectrum data (in deutero-dimethylsulfoxide, TMS internal standard) of Compound VII-A, Compound VII-C, Compound VII-E and Compound VII-R which are included within the general formula (VII) above and shown in Table 11 above as concrete examples of these compounds.

Compound VII-A

δ 0.86 (3H, t, CH$_3$(CH$_2$)$_5$CO$_3$ J=7 Hz), 2.29 (3H, s, NMe-5'''), 3.02 (3H, s, NMe-8'''), 5.02 (1H, s, H-1''), 5.52 (1H, s, H-1'), 5.66 (1H, d, H-5, J=8 Hz), 7.72 (1H, d, H-6, J=8 Hz), 11.33 (1H, s, NH-3).

Compound VII-C

δ 0.86 (3H, t, CH$_3$(CH$_2$)$_7$CO, J=7 Hz), 2.29 (3H, s, NMe-5'''), 3.02 (3H, s, NMe-8'''), 5.02 (1H, s, H-1''), 5.52 (1H, d, H-1', J=~2 Hz), 5.66 (1H, dd, H-5, J=2, 8 Hz), 7.72 (1H, d, H-6, J=8 Hz), 11.33 (1H, d, NH-3, J=2 Hz).

Compound VII-E

δ 0.86 (3H, t, CH$_3$(CH$_2$)$_9$CO$_3$ J=7 Hz), 2.28 (3H, s, NMe-5'''), 3.01 (3H, s, NMe-8'''), 5.02 (1H, s, H-1''), 5.52 (1H, s, H-1'), 5.66 (1H, d, H-5, J=8 Hz), 7.73 (1H, d, H-6, J=8 Hz), 11.33 (1H, s, NH-3).

Compound VII-R

δ 0.85 (3H, t, CH$_3$(CH$_2$)$_7$CH=, J=7 Hz), 2.28 (3H, s, NMe-5'''), 3.01 (3H, s, NMe-8'''), 5.02 (1H, s, H-1''), 5.52 (1H, s, H-1'), 5.66 (1H, d, H-5, J=8 Hz), 7.72 (1H, d, H-6, J=8 Hz), 11.33 (1H, s, NH-3).

Next, there are given an experimental example of the preparation of a uridine derivative of the formula (IX) above from caprazol according to the eleventh aspect of this invention as well as an experimental example of the preparation of an imidazolidinone derivative of the formula (VIII) above from the 5''-N-Boc-protected derivative of the said uridine derivative according to the tenth aspect of this invention with reference to Example 12 given below.

Example 12

(a) Preparation of the Uridine Derivative of the Following Formula (IX)

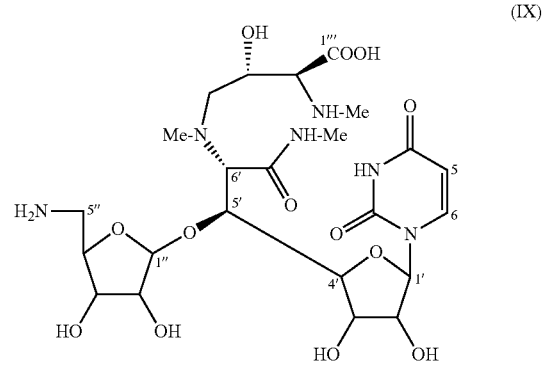

Caprazol (100.9 mg) was dissolved in 40% aqueous methylamine solution (3.0 ml) and the resulting mixture was subjected to the reaction intended at room temperature for 19 hours. The resulting reaction solution was concentrated under a reduced pressure and then dried under a reduced pressure. The resulting residue was washed with a mixed solvent of chloroform-diethyl ether (1:1). The residue thus washed was dried under a reduced pressure to give a solid (93.8 mg). The solid was chromatographed for the purification by passing through a column packed with Amberlite (Registered Trade Mark) CG-50 (NH$_4^+$ form), followed by developing the column with water. The resulting eluate fractions containing the desired compound are concentrated under a reduced pressure and then the concentrated was dried under a reduced pressure, thus affording the titled compound (72.5 mg; yield: 680).

$[\alpha]_D^{20}$ +30° (c 1, H$_2$O)

$^1$H-NMR spectrum (500 MHz, in D$_2$O)

δ 2.30 (3H, s, NMe-6'), 2.50 (3H, s, NMe-2'''), 2.61 (3H, s, NMe-7'), 3.39 (1H, d, H-2''', J$_{2''',3'''}$=4 Hz), 3.47 (1H, d, H-6', J$_{5',6'}$=9 Hz), 5.06 (1H, d, H-1'', J$_{1'',2''}$=2 Hz), 5.54 (1H, d, H-1', J$_{1',2'}$=2.5 Hz), 5.67 (1H, d, H-5, J$_{5,6}$=8 Hz), 7.61 (1H, d, H-6).

(b) Synthesis of 5"-N-Boc-uridine Derivative Represented by the Following Formula (IXa)

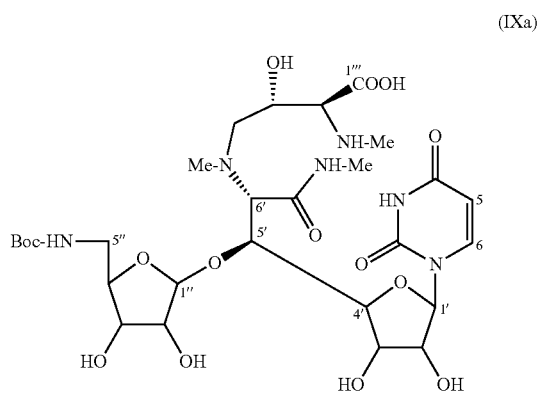

(IXa)

5"-N-Boc-caprazol (14.6 mg) as obtained in Example 8(a) was dissolved in aqueous 40% methylamine solution (0.73 ml) and the resulting mixture was subjected to the reaction intended at room temperature for 2 days. The resulting reaction solution was concentrated under a reduced pressure and then dried under a reduced pressure, thus affording the titled compound (13.7 mg; yield: 90%).

$[\alpha]_D^{21}$ −13° (c 1.5, methanol)

$^1$H-NMR spectrum (500 MHz, in deutero-methanol)

δ 1.49 (9H, s, methyl in t-butoxycarbonyl group), 2.46 (3H, s, NMe-6'), 2.73 (3H, s, NMe-7'), 2.75 (3H, s, NMe-2'''), 5.09 (1H, br. s, H-1"), 5.77 (1H, d, H-5, $J_{5, 6}$=8 Hz), 5.88 (1H, d, H-1', $J_{1', 2'}$=4 Hz), 7.95 (1H, d, H-6).

(c) Synthesis of N-Protected-Imidazolidinone Derivative Represented by the Following Formula (VIIIa-1) (Corresponding to a Compound Included within the Derivative of the Formula (VIIIa) Above)

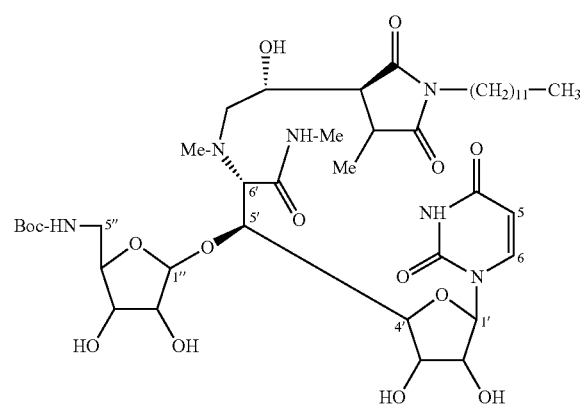

(VIIIa-1)

The N-protected-uridine derivative of the formula (IXa) as obtained in the step (b) above (167.6 mg) was dissolved in N,N-dimethylformamide (2.5 ml), and to the resultant solution was added dodecyl isocyanate (0.63 ml) as an alkyl isocyanate of the formula (XXIV) above. The resulting mixture was subjected to the reaction intended at room temperature. After 1 hour from the start of the reaction, a further amount (0.63 ml) of dodecyl isocyanate was added and the reaction was proceeded for further 3 hours. The insolubles so deposited were filtered off and the remaining reaction solution was concentrated under a reduced pressure. The resulting concentrate was extracted with chloroform, and the chloroform extract was washed with an aqueous saturated sodium sulfate solution, dried over anhydrous sodium sulfate and then concentrated under a reduced pressure. The resulting residue was washed with hexane and dried under a reduced pressure, to give a solid (261 mg). This solid was purified by a silica-gel column chromatography (developing system: chloroform-methanol-water, 9:1:0.1), thus affording the titled compound of the formula (VIIIa-1) (32.5 mg) (yield: 15%).

$^1$H-NMR spectrum (500 MHz, in deutero-methanol)

δ 0.89 (3H, t, N(CH$_2$)$_{11}$Me, J=7 Hz), 2.47 (3H, s, NMe-6'), 2.75 (3H, s, NMe-7'), 2.99 (3H, s, NMe-2'''), 5.09 (1H, d, H-1").

(d) Synthesis of the Imidazolidinone Derivative of the Following Formula (VIII-1) (Corresponding to Compound VIII-G Shown in Table 13 Above)

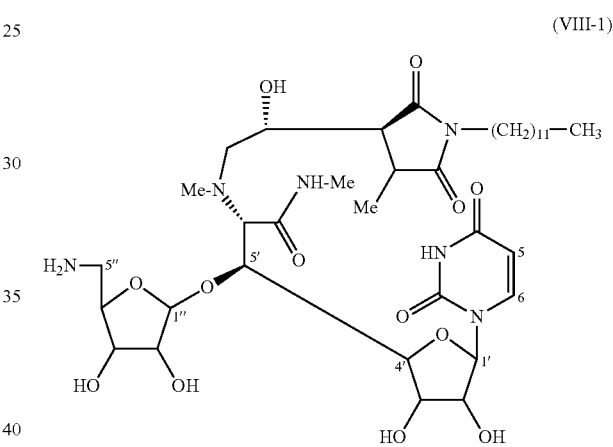

(VIII-1)

The N-protected imidazolidinone derivative of the formula (VIIIa-1) (32.5 mg) obtained in the step (c) above was dissolved in a mixed solution of trifluoroacetic acid-methanol (8:2) (0.33 ml). The resulting mixture was subjected to the reaction intended at room temperature for 2 hours (for the deprotection reaction). The resulting reaction solution was concentrated under a reduced pressure and the resulting residue was washed with diethyl ether and then dried under a reduced pressure, thus affording the titled compound of the formula (VIII-1) in the form of an addition salt of bis-trifluoroacetic acid (32.5 mg; yield: 88%).

$[\alpha]_D^{20}$ +13° (c 2, methanol)

$^1$H-NMR spectrum (500 MHz, in deutero-methanol)

δ 0.89 (3H, t, N(CH$_2$)$_{11}$Me, J=7 Hz), 5.16 (1H, d, H-1"), 7.74 (1H, d, H-6, $J_{5,6}$=8 Hz).

Furthermore, the preparation of antibiotics, caprazamycins A-F which are used as starting materials in the preparation of caprazene and caprazol is now illustrated with reference to the following Reference Example 1.

Reference Example 1

Preparation of Antibiotics, Caprazamycins A-F

*Streptomyces* sp. MK730-62F2 (deposited under the depository number of FERM BP-7218), which had been cultured on an agar slant culture medium, was inoculated in a culture medium which had been prepared by placing into Erlenmeyer flasks (500 ml-capacity) 110 ml portions of a liquid culture medium comprising 2% galactose, 2% dextrin, 1% glycerine, 1% Bacto-Soyton (a product of Difco Co.), 0.5% corn steep liquor, 0.2% ammonium sulfate and 0.2% calcium carbonate (adjusted to a pH of 7.4) and sterilizing the culture medium in the flasks at 120° C. for 20 minutes in a usual manner, before the inoculation of the strain MK730-62F2 was done. The liquid culture medium so inoculated was then subjected to shaking cultivation with rotation at 30° C. for 2 days, whereby giving a seed culture broth as intended.

In a tank fermenter (30 L-capacity), there was prepared a culture medium (15 L) comprising 2.4% tomato paste (a product of Kagome Co.), 2.4% dextrin, 1.2% yeast extract (a product of Oriental Co.) and 0.0006% cobalt chloride (adjusted to a pH of 7.4), which was then sterilized to give a productive culture medium. To this productive culture medium was inoculated a 2% proportion of the above-mentioned seed culture broth. The cultivation of the said strain was conducted in the tank fermenter at 27° C., with aeration of 15 L of air per minute and stirring speed of 200 rpm for 6 days.

The resulting culture broth was centrifuged to separate the culture broth filtrate (12 L) from the cultured microbial cells. Subsequently, methanol (6 L) was added to the microbial cells and the resulting mixture was well stirred to extract from the microbial cells the already known antibiotics, caprazamycins A, B, C, E and F, and the novel antibiotics, caprazamycins D, G, D1 and G1 into methanol (hereinafter, sometimes, these antibiotics, caprazamycins A, B, C, D, E, F, G, D1 and G1, are generically described as caprazamycins).

The culture broth filtrate and the methanolic extract of the cells obtained as above were combined together, and the resulting mixture (18 L) was passed through a column packed with 750 ml of a synthetic adsorbent resin made of aromatic polymer, namely Diaion HP-20 (a product of Mitsubishi Chemical Co., Japan) to adsorb caprazamycins therein.

Through this Diaion HP-20 column containing the caprazamycins so adsorbed, were passed 2.25 L each of deionized water, 50% aqueous methanol, 80% aqueous methanol, 80% aqueous acetone and acetone, in order. The caprazamycins were eluted from the column, mainly in the eluate fractions as eluted with 80% aqueous acetone. In addition, the eluate fractions as eluted with the 50% aqueous methanol and with the 80% aqueous methanol also contained caprazamycins. These eluate fractions as eluted with the two aqueous methanolic solvents were combined together and the mixture was again passed through a column of Diaion HP-20 (750 ml), whereby caprazamycins were adsorbed in the adsorbent of this column. Then, elution of this column was effected by passing 80% aqueous methanol (2.25 L) therethrough. Subsequently, the column was eluted with 80% aqueous acetone (2.25 L). The resulting eluate as eluted with 80% aqueous acetone was combined with the first eluate as eluted with 80% aqueous acetone in the first stage column and the resulting mixture was concentrated to dryness under a reduced pressure, thus affording a partially purified product comprising caprazamycins (10.1 g).

The partially purified product (10.1 g) containing caprazamycins was dissolved in a mixed solvent (50 ml) of chloroform-methanol (1:2), to which solution was added Kieselgur (Art. 10601, a product of Merck & Co.) (50 ml) and the solvent was removed by concentration to dryness under a reduced pressure. The resulting solid residue obtained by adsorbing the caprazamycins in the Kieselgur was placed on the top of a silica-gel column (54 mm inner diameter and 200 mm long) to be subjected to a chromatography. The development treatment was made, in order, with chloroform-methanol-water (4:1:0.1), chloroform-methanol-water (2:1:0.2) and chloroform-methanol-water (1:1:0.2) (1.35 L in each time).

The eluates from the silica-gel column were collected each in fractions by means of fraction collector, so that fractions Nos. 1 to 53 were collected each in 20 g portions and fractions Nos. 54 to 117 were collected each in 19 g portions. In this way, the active fractions containing caprazamycins A, B, C, D, E, F and G were eluted in fractions Nos. 66 to 83 and the active fractions containing caprazamycins D1 and G1 were eluted in fractions Nos. 84 to 144. The fractions Nos. 66 to 83 containing caprazamycins A, B, C, D, E, F and G were combined together and concentrated to dryness under a reduced pressure to yield a partially purified product comprising caprazamycins A, B, C, D, E, F and G (625.3 mg). The fractions Nos. 54 to 117 were also combined together and concentrated to dryness under a reduced pressure to yield a partially purified product comprising caprazamycins D1 and G1 (1.28 g).

Subsequently, the partially purified product containing caprazamycins A, B, C, D, E, F and G was subjected to treatments for the isolation and purification of the respective compounds from one another. Thus, methanol (5 ml) was added to the said partially purified product above (625.3 mg) and the resulting solution was allowed to stand at 5° C. under cold and dark conditions, whereby a fraction of precipitate as deposited (537.3 mg) was obtained as a product which contains caprazamycins A, B, C, D, E, F and G. Then, the fraction of the deposited precipitate containing caprazamycins A, B, C, D, E, F and G was purified by subjecting it to HPLC (CAPCELLPAKC18, φ20×250 mm, a product of Shiseido, Co.). In this HPLC, the development was effected by 50% aqueous acetonitrile-0.05% formic acid as the development solvent (at a flow rate of 12.0 ml/min), whereby caprazamycin A was eluted after 61-68 minutes, caprazamycin B was eluted after 52-60 minutes, caprazamycin C was eluted after 39-41 minutes, a mixture of caprazamycin D and caprazamycin G was eluted after 30-38 minutes, caprazamycin E was eluted after 25-28 minutes, and caprazamycin F was eluted after 22-25 minutes of the development. The respective active fractions were collected, separately and concentrated to dryness under a reduced pressure, thus to afford caprazamycin A (56.9 mg), caprazamycin B (90.3 mg), caprazamycin C (19.7 mg), a mixture comprising caprazamycin D and caprazamycin G (162.9 mg), caprazamycin E (30.3 mg) and caprazamycin F (25.5 mg), respectively.

Further, the mixture comprising caprazamycin D and caprazamycin G obtained as above (162.9 mg) was purified by HPLC (CAPCELLPAK C18, φ20×250 mm, a product of Shiseido, Co.). In this HPLC, the development was effected with the solvent system of 50% aqueous acetonitrile-0.025% trifluoroacetic acid (at a flow rate of 9.0 ml/min), whereby caprazamycin D was eluted after 55-69 minutes and caprazamycin G was eluted after 48-53 minutes of the development. The respective active fractions were collected separately and then concentrated to dryness under a reduced pressure, thus to afford caprazamycin D (69.7 mg) and caprazamycin G (39.0 mg), respectively.

Further, the partially purified product (1.28 g) containing caprazamycins D1 and C1 obtained as above was subjected to the treatments for the isolation and purification of the respective compounds from each other by HPLC (CAPCELL- PAKC18, φ20×250 mm, a product of Shiseido, Co.). In this HPLC, the development was effected with the solvent system of 45% aqueous acetonitrile-0.05% trifluoroacetic acid (at a flow rate of 12.0 ml/min), whereby caprazamycins G1 and D1 were eluted after 36-49 minutes of the development. These eluate fractions were collected and concentrated to dryness under a reduced pressure, thus to afford a mixture of caprazamycin D1 and caprazamycin G1 (187 mg). The said mixture was further subjected to HPLC (CAPCELLPAK C18, φ20×250 mm, a product of Shiseido, Co.) wherein the development was effected with the solvent system of 44% aqueous acetonitrile-0.025% trifluoroacetic acid (at a flow rate of 9.0 ml/min), whereby caprazamycin D1 was eluted after 46-52 minutes and caprazamycin G1 was eluted after 41-44 minutes of the development. These eluate fractions were collected and concentrated to dryness under a reduced pressure, respectively, thus to afford each of caprazamycin D1 (54.1 mg) and caprazamycin G1 (57.6 mg).

INDUSTRIAL APPLICABILITY

As described hereinbefore, caprazene and caprazol are now produced by hydrolysis of caprazamycins according to this invention. Caprazene and caprazol are useful compounds for the production of semi-synthesized derivatives having excellent antibacterial activities. According to this invention, further, there are synthesized novel compounds which are a caprazene-1'''-amide derivative of the formula (II), a caprazene-1'''-ester derivative of the formula (III), a caprazol-1'''-amide derivative of the formula (V), a caprazol-1'''-amide-3'''-ester derivative of the formula (VI), a caprazol-3'''-ester derivative and a caprazol-1'''-ester-3'''-ester derivative of the formula (VII) or an imidazolidinone derivative CP-IM of the formula (VIII). These derivatives of caprazene and caprazol have excellent antibacterial activities against a variety of bacteria and are useful as antibacterial agents. Further, the uridine derivative of the formula (IX) as obtained according to this invention is useful as novel intermediate compound utilizable in the syntheses of a variety of novel compounds.

The invention claimed is:
1. A 5''-N-alkoxycarbonyl derivative of caprazene, which is the compound represented by the following formula (Ia):

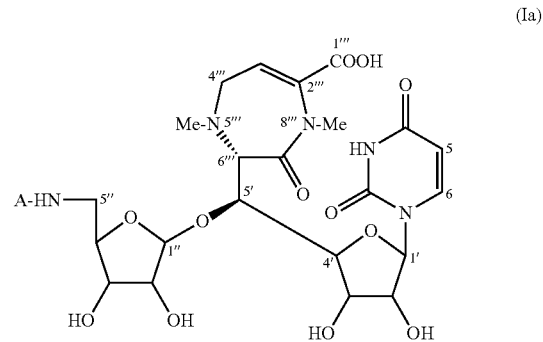

(Ia)

wherein Me stands for methyl group, and A is an N-alkoxycarbonyl group.

2. A 5''-N-aralkyloxycarbonyl derivative of caprazene, which is the compound represented by the following formula (Ia):

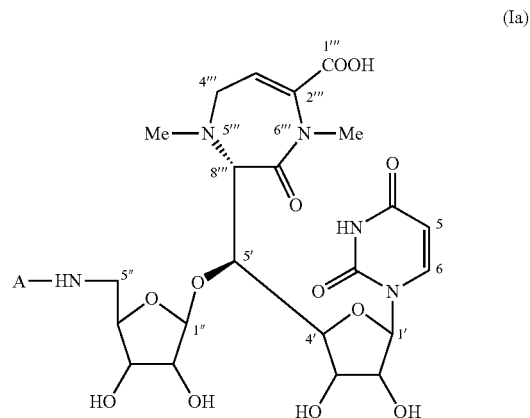

(Ia)

wherein Me stands for methyl group, and A is an N-aralkyloxycarbonyl group.

* * * * *